United States Patent
Kozubal et al.

(10) Patent No.: US 11,912,979 B2
(45) Date of Patent: *Feb. 27, 2024

(54) FILAMENTOUS FUNGAL BIOMATS, METHODS OF THEIR PRODUCTION AND METHODS OF THEIR USE

(71) Applicant: The Fynder Group, Inc., Chicago, IL (US)

(72) Inventors: Mark A. Kozubal, Bozeman, MT (US); Richard E. Macur, Manhattan, MT (US); Yuval C. Avniel, Missoula, MT (US)

(73) Assignee: The Fynder Group, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,314

(22) Filed: Jul. 28, 2022

(65) Prior Publication Data

US 2023/0014203 A1 Jan. 19, 2023

Related U.S. Application Data

(60) Division of application No. 17/539,186, filed on Nov. 30, 2021, now Pat. No. 11,505,779, which is a continuation of application No. 17/167,976, filed on Feb. 4, 2021, now Pat. No. 11,261,420, which is a continuation of application No. 16/990,857, filed on Aug. 11, 2020, which is a continuation of application No. 16/705,036, filed on Dec. 5, 2019, now Pat. No. 10,787,638, which is a continuation of application No. 16/118,370, filed on Aug. 30, 2018, now Pat. No. 10,533,155, which is a continuation of application No. PCT/US2017/020050, filed on Feb. 28, 2017.

(60) Provisional application No. 62/345,973, filed on Jun. 6, 2016, provisional application No. 62/340,381, filed on May 23, 2016, provisional application No. 62/302,123, filed on Mar. 1, 2016.

(51) Int. Cl.

| | | |
|---|---|---|
| *C12N 1/14* | (2006.01) | |
| *C12N 1/02* | (2006.01) | |
| *C02F 3/34* | (2023.01) | |
| *C12R 1/77* | (2006.01) | |
| *C12R 1/645* | (2006.01) | |
| *C12R 1/845* | (2006.01) | |
| *C12R 1/785* | (2006.01) | |
| *C12R 1/66* | (2006.01) | |
| *C12R 1/84* | (2006.01) | |
| *C12R 1/885* | (2006.01) | |
| *C12R 1/80* | (2006.01) | |

(52) U.S. Cl.
CPC ............. *C12N 1/14* (2013.01); *C02F 3/347* (2013.01); *C12N 1/02* (2013.01); *C12N 1/145* (2021.05); *C12R 2001/645* (2021.05); *C12R 2001/66* (2021.05); *C12R 2001/77* (2021.05); *C12R 2001/785* (2021.05); *C12R 2001/80* (2021.05); *C12R 2001/84* (2021.05); *C12R 2001/845* (2021.05); *C12R 2001/885* (2021.05)

(58) Field of Classification Search
None
See application file for complete search history.

(56) References Cited

U.S. PATENT DOCUMENTS

| | | |
|---|---|---|
| 5,362,634 A | 11/1994 | Boeck et al. |
| 11,505,779 B2 | 11/2022 | Kozubal et al. |
| 2003/0134120 A1 | 7/2003 | Kim et al. |
| 2004/0092014 A1 | 5/2004 | Hiromoto |
| 2012/0227899 A1* | 9/2012 | McIntyre ............... C12N 1/14 156/242 |
| 2015/0038326 A1 | 2/2015 | Araldi et al. |

FOREIGN PATENT DOCUMENTS

| | | |
|---|---|---|
| CN | 101327006 | 12/2008 |
| JP | 2003-520576 | 7/2003 |
| JP | 2005-533118 | 11/2005 |
| JP | 2008-029251 | 2/2008 |
| JP | 2012-520682 | 9/2012 |
| JP | 7022072 | 2/2022 |
| SA | 518392300 | 11/2021 |
| WO | WO 2014/145265 | 9/2014 |
| WO | WO 2016/004380 | 1/2016 |

OTHER PUBLICATIONS

Oostra et al., "Intra-Particle Oxygen Diffusion Limitation in Solid-State Fermentation", Biotechnology and Bioengineering, vol. 75, pp. 13-24 (Year: 2001).*
Mahapatra et al., "Fungal Exopolysaccharide: Production, Composition and Applications", Microbiology Insights, vol. 6, pp. 1-16 (Year: 2013).*
Ma et al., "Preparation and characteristics of biodegradable mulching films based on fermentation industry wastes," International Biodeterioration and Biodegradation, vol. 111, Apr. 28, 2016, pp. 54-61.
Notice of Allowance for U.S. Appl. No. 17/167,976, dated Oct. 18, 2021, 8 pages.
Official Action for U.S. Appl. No. 17/539,186, dated Feb. 17, 2022, 7 pages. Restriction Requirement.
Official Action for U.S. Appl. No. 17/539,186, dated Mar. 17, 2022, 18 pages.
Official Action for U.S. Appl. No. 17/539,186, dated May 23, 2022, 15 pages.

(Continued)

*Primary Examiner* — Michelle F. Paguio Frising
(74) *Attorney, Agent, or Firm* — Sheridan Ross P.C.

(57) ABSTRACT

A novel method of growing fungi is disclosed which uses an engineered artificial media and produces high density filamentous fungi biomats that can be harvested with a minimum of processing and from which fungal products such as antibiotics, proteins, and lipids can be isolated, the method resulting in lowered fungus cultivation costs for energy usage, oxygenation, water usage and waste stream production.

12 Claims, 14 Drawing Sheets

Specification includes a Sequence Listing.

(56) References Cited

OTHER PUBLICATIONS

Notice of Allowance for U.S. Appl. No. 17/539,186, dated Jul. 20, 2022, 9 pages.
Galbe et al., "Pretreatment of Lignocellulosic Materials for Efficient Bioethanol Production," Advances in Biochemical Engineering/Biotechnology: Biofuels, vol. 108, Jul. 24, 2007, pp. 41-65.
Official Action for U.S. Appl. No. 17/937,853, dated Mar. 10, 2023, 26 pages.
Official Action for U.S. Appl. No. 16/990,857, dated Apr. 6, 2023, 10 pages. Restriction Requirement.
Pasarell et al., "Viability of Fungal Cultures Maintained at −70C," Journal of Clinical Microbiology, vol. 30, No. 4, Apr. 1992, pp. 1000-1004.
Schubert et al., "Development of total and viable extraradical mycelium in the vesicular-arbuscular mycorrhizal fungus Glomus clarum Nicol. & Schenck," The New Phytologist., vol. 107, 1987, pp. 183-190.
Official Action for U.S. Appl. No. 16/990,857, dated Jun. 23, 2023, 12 pages.
Official Action for U.S. Appl. No. 17/937,853, dated Jul. 5, 2023, 26 pages.

* cited by examiner

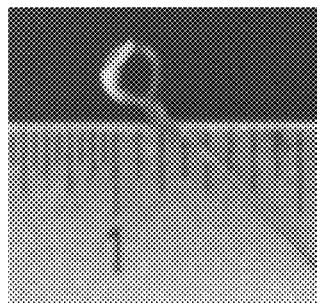
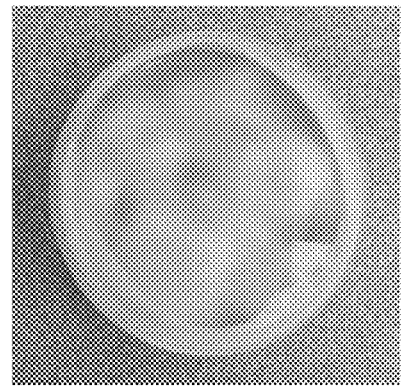
FIG. 3A                    FIG. 3B
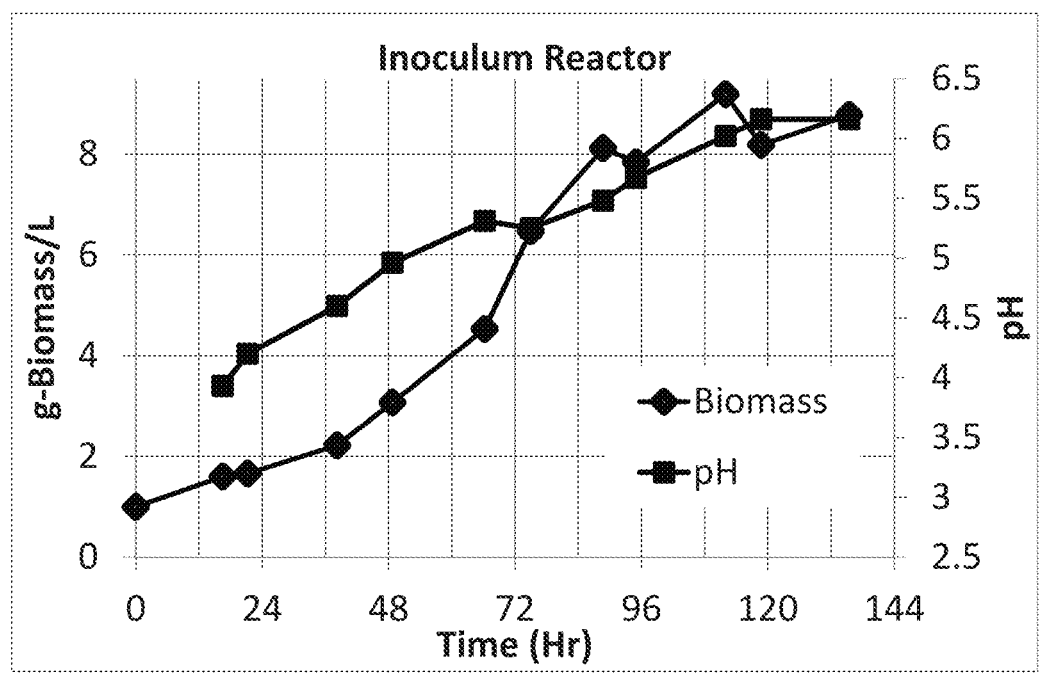
FIG. 4

SEQUENCE LISTING

```
Sequence total quantity: 3
SEQ ID NO: 1            moltype = DNA  length = 1077
FEATURE                 Location/Qualifiers
source                  1..1077
                        mol_type = genomic DNA
                        note = Organism is a fungus of the genus Fusarium
                        organism = unidentified
SEQUENCE: 1
atgatcactg gtacttccca ggccgattgc gccattctca tcattgccgc cggtactggt   60
gagttcgagg ctggtatctc caaggatggc cagaccgtg agcacgctct tcttgcctac   120
accttggtg tcaagaacct catcgtcgcc atcaacaaga tggacaccac caagtggtct   180
gaggcccgtt accaggagat catcaaggag acctcctcct tcatcaagaa ggtcggctac   240
aaccccaagg ctgtcgcttt cgtccccatc tccggtttca acggtgacaa catgcttacc   300
ccctccacca actgcccctg gtacaagggt tgggagcgtg agatcaagtc cggcaagctc   360
accggcaaga ccctcctcga ggccattgac tccatcgagc ctcccaagcg tcccgttgac   420
aagcccctcc gtcttcccct ccaggatgtc tacaagatcg gtggtattgg aacggttccc   480
gtcggccgta ttgagactgg tgtcatcaag cccggtatgg tcgttacctt cgctccctcc   540
aacgtcacca ctgaagtcaa gtccgtcgag atgcaccacg agcagctcag tgagggccag   600
cccggtgaca acgttggttt caacgtgaag aacgtctccg tcaaggacat ccgacgtggt   660
aacgtcgctg gtgactccaa gaacgacccc cccaggggtg ccgcttcttt caccgcccag   720
gtcatcgtcc tcaaccaccc cggccaggtc ggtgctggtt acgctcccgt cctcgattgc   780
cacactgccc acattgcctg caagttcgcc gagatccagg agaagatcga ccgccgaacc   840
ggtaaggcta ctgaggccgc tcccaagttc atcaagtctg gtgactccgc catcgtcaag   900
atggttccct ccaagcccat gtgtgtcgag gctttcactg actaccctcc tctgggtcgt   960
ttcgccgtcc gtgacatgcg acagactgtc gccgtcggtg tcatcaaggc cgtcgagaag   1020
tccaccggtg ctgctggcaa ggtcaccaag tccgctgcca aggccgccaa gaaataa     1077

SEQ ID NO: 2            moltype = DNA  length = 480
FEATURE                 Location/Qualifiers
source                  1..480
                        mol_type = genomic DNA
                        note = organism is a fungus of the genus Fusarium
                        organism = unidentified
```

```
SEQUENCE: 2
gtggatcttg agcccggtcc tcaggatgcc atccgcgccg ggcccctagg ccagcttttc    60
cgccccgaca acttcgtcgc cggaaatgcc agcgccggta acaactgggc caagggtcat   120
tacaccgaag gtgctgagct cgttgaggag gccatcgatg ttgtgcgaca cgaggttgag   180
aactgtgacc atcttcaggg tttccagctc acccactctc tcggcggtgg taccggttct   240
ggtatgggaa cgcttcttct gtcgaaaatc cgtgaggagt ttcccgatcg catgatggct   300
acttttccg ttatgccttc gcctaaggtt tctgataccg ttgtcgaacc ttacaacgcc    360
actttgtcat tgaaccagct tgtcgagaac tccgatgaga ccttctgtat cgataacgag   420
gctttgtacg acatttacga gaagaccctg aagattgctg atccttctta cgccgatctc   480

SEQ ID NO: 3         moltype = DNA  length = 962
FEATURE              Location/Qualifiers
source               1..962
                     mol_type = genomic DNA
                     note = organism is a fungus of the genus Fusarium
                     organism = unidentified
SEQUENCE: 3
ccgcgggaa tactacctga tccgaggtca cattcagagt tggggttta cggcttggcc     60
gcgccgcgta ccagttgcga gggtttact actacgcaat ggaagctgca gcgagaccgc   120
cactagattt cggggccggc ttgccgcaag ggctcgccga tccccaacac caaacccggg   180
ggcttgaggg ttgaaatgac gctcgaacag gcatgcccgc cagaatactg gcgggcgcaa   240
tgtgcgttca aagattcgat gattcactga attctgcaat tcacattact tatcgcattt   300
tgctgcgttc ttcatcgatg ccagaaccaa gagatccgtt gttgaaagtt ttgatttatt   360
tatggtttta ctcagaagtt acatatagaa acagagttta ggggtcctct ggcgggccgt   420
cccgttttac cgggagcggg ctgatccgcc gaggcaacaa ttggtatgtt cacaggggtt   480
tgggagttgt aaactcggta atgatccctc cgcagttcct acctacggat aggatcatta   540
ccgagtttac aactcccaaa cccctgtgaa catacccatt gttgcctcgg ccggatcagc   600
ccgctccgg ttaaaacggg acggcccgcc agagtaccc taaactctgt ttctatatgt     660
aacttctgag taaaaccata aataaatcaa aactttcaac acgcatctct tgcttctgtc   720
atcgatgaag aacgcagcaa aatgcgatag tcatgtgatt gcacattcag tgaatcatcg   780
atcttgacgc acattgcgcc tgcagtattc tggcggtcat gcctgttcga gcgtcattca   840
gccctcagcc ctcggttgtg ttcgggatcg gcgagtcctg cgccagcgac cggatcagtg   900
gcgtctgcct gcgcctccat tgcggttaga gttaagccct cgcccacttg ttttacgcta   960
ac                                                                  962
```

FILAMENTOUS FUNGAL BIOMATS, METHODS OF THEIR PRODUCTION AND METHODS OF THEIR USE

CROSS-REFERENCE TO RELATED APPLICATIONS

This application is a divisional application of U.S. patent application Ser. No. 17/539,186, filed 30 Nov. 2021, which is a continuation application of U.S. patent application Ser. No. 17/167,976, filed 4 Feb. 2021, which is a continuation application of continuation application of U.S. patent application Ser. No. 16/990,857, filed 11 Aug. 2020, which is a continuation application of U.S. patent application Ser. No. 16/705,036, filed 5 Dec. 2019 and now issued as U.S. Pat. No. 10,787,638, which is a continuation application of U.S. patent application Ser. No. 16/118,370, filed 30 Aug. 2018 and now issued as U.S. Pat. No. 10,533,155, which is a continuation application of PCT Application PCT/US2017/020050, filed 28 Feb. 2017, which claims priority under 35 U.S.C. § 119(e) to U.S. Provisional Patent Applications 62/345,973, filed 6 Jun. 2016, 62/340,381, filed 23 May 2016, and 62/302,123, filed 1 Mar. 2016. The entirety of each of the above-referenced applications is hereby incorporated by reference for all purposes.

REFERENCE TO SEQUENCE LISTING

This application contains a sequence listing submitted electronically in XML format named "10087-2-PCT-C5-D1.xml" having a size of 7000 bytes and created on 31 Aug. 2022. The information contained in the XML file is hereby incorporated by reference in its entirety pursuant to 37 C.F.R. § 1.52(e)(5).

TECHNICAL FIELD

This application relates to isolated filamentous fungal strains within the *Ascomycota, Zygomycota, Basidiomycota, Glomermycota*, and *Chytridiomycota phyla*, such as *Fusarium* species, *Aspergillus* species, *Tricoderma* species, *Penicillium* species, species within the *Mucorales*, including *Rhizopus* species, the acidophilic filamentous fungal strain designated as MK7 and their progeny as well as methods of conducting surface fermentation to produce filamentous fungi biomats from such fungal strains which produce a large variety of useful products.

BACKGROUND

The cells of most fungi grow as tubular, elongated and thread like structures called hyphae which may contain multiple nuclei and which extend by growing at their tips. This is in contrast to similar-looking organisms, such as filamentous green algae, which grow by repeated cell division with a chain of cells.

The collective body of hyphae that constitutes the vegetative stage of a fungus is called a mycelium (plural mycelia). The mycelium can be considered the main body or form of the fungus and is often described as being filamentous. Growth occurs by the asexual reproduction of hypha, which grow into branching chains. Mycelium is important to the fungus because it can navigate through soil or wood and use that substrate as food, which the fungus will need if it is to produce fruit bodies (e.g., basidoiocarps) such as mushrooms, brackets, truffles, cups, or morels.

Mycelia excrete exoenzymes which can kill living tissue (necrotrophic) and then absorb that dead material (saprotrophic), simply absorbing material that was already dead (again, saprotrophic), or by feeding off of living tissue (biotrophic).

While it is believed that all of the *phyla* of the Fungi kingdom contain filamentous species, the *Ascomycota* and *Zygomycota phyla*, in particular have a large number of filamentous species. The members of these *phyla* make a large variety of products such as proteins, amino acids, oils, medicinals (e.g., penicillin), food (e.g., tempeh), food additives, food preservatives (e.g., citric acid), and industrial enzymes as well as being used in baking, and the production of chees, beer, and wine.

State of the art solid-substrate fermentation (SSF) suffers from a number of distinct disadvantages. For example, the final product, i.e. the produced biomass, is intimately mixed with the solid substrate which is fundamentally difficult to separate one from the other. Typically, SSF produces fungal biomass in low concentrations, has very low conversion rates and ultimately results in low yields. SSF requires specific water activities for effective fermentation. Delivering and maintaining the right amount of water activity is difficult and expensive to implement. Aerating SSF systems is also difficult to accomplish, further exacerbating conversion efficiencies and limiting system yields. Improper water activity as well as poor aeration pose limitations to mass and heat transfer, which result in overheating and deficiencies in oxygen supply. The resulting biomass is characterized as having randomly oriented filaments, which greatly limit utility in certain applications; i.e. food and/or animal feed.

Quorn™, a product comprised primarily of the biomass of *Fusarium venenatum* filamentous fungi offers a relatively nutritional mycoprotein. Quorn™ is produced by a state of the art submerged fermentation system, capable of producing large volumes in a batch based continuous process. Although commercially viable, the production methodology suffers from a number of distinct disadvantages. In order to meet commercial demands, Quorn™ uses bioreactors that cost between \$35-40 million each. The Quorn™ system is run continuously in a single reactor until the fungal system matures beyond key metrics or is contaminated by another species. At this point, production comes to a standstill, the reactor and all associated plumbing is emptied and sterilized, a process that can take weeks to complete and introduces a number of serious issues for a supplier of commercial product. Such issues are, for example, (1) difficult to predict production cycles, (2) costs incurred for cleaning and stopping production, (3) difficulties in controlling inventory, etc. Further, submerged fermentation in large bioreactors requires tremendous amounts of energy to aerate and mix. Separation of the biomass from the liquid in which it ferments requires centrifugation, which is also known to be a capital intensive and energy demanding process. The process is further water intensive, necessitating the handling of large amounts of waste water. The biomass produced is characterized as having short filament lengths, which limits its ability to directly convert to food/feed products without introducing bind agents and subsequent process steps which incur further costs, difficulties and effort to effectively manage.

The present filamentous mycelia growth methodologies suffer from a number of disadvantages. For example, facilities having the proper aeration and equipment needed for fungal growth and subsequent separation of the fungal mycelia from the growth media (e.g., centrifuges) require significant capital expenses, especially for conducting fungal growth on an industrial scale. Not only do the current processes require substantial energy and water inputs, but they also result in the generation of a large waste stream.

Consequently, there is a need in the industry for a streamlined approach to filamentous mycelia filamentous fungi biomat formation.

SUMMARY OF THE INVENTION

The current disclosure overcomes the limitation of the processes currently used. Here, filamentous fungi biomats are generated via surface fermentation after inoculation of the desired fungal strain into a novel growth media where no aeration is required. This method of surface fermentation is applicable to a large variety of fungal species which are able to produce a wide assortment of products across a spectrum of different industries. The media developed generates rapid cell growth, creates high density filamentous fungi biomats with long filaments, produces small waste streams, and allows engineering of the filamentous fungi biomat produced as a function of carbon source, carbon to nitrogen ratio (C:N), and process parameters. The overall effect is one in which high production rates occur with minimal environmental impact as measured by water usage, energy usage, equipment requirements, and carbon footprint.

Therefore, the current disclosure provides an artificial media suitable for culturing filamentous fungi and enabling their production of a filamentous fungal biomat. The artificial media comprises at least the following macronutrients: nitrogen (N), phosphorus (P), calcium (Ca), magnesium (Mg), carbon (C), potassium (K), sulfur (S), oxygen (O), hydrogen (H) and the following trace nutrients: iron (Fe), boron (B), copper (Cu), Manganese (Mn), molybdenum (Mo), and zinc (Zn). In some instances, the trace nutrients are augmented with the following additional trace nutrients: chromium (Cr), selenium (Se), and vanadium (V). The artificial media has varying C:N ratios which favor production of filamentous fungi biomats having either a high protein:lipid ratio or a high lipid:protein ratio.

Also provided are conditions culturing various filamentous fungi for filamentous fungi biomat production, some of which are acidophilic, such as species and/or strains of *Fusarium, Fusisporium, Pseudofusarium, Gibberella, Sporotrichella, Aspergillus. Penicillium, Triocoderma*, species within the *Mucorales* sp. (e.g., *Rhizopus* sp.) and the filamentous fungal strain designated as MK7. Depending on the species and/or strain, the pH of the culturing media ranges from about 0.68 to about 8.5 and in some cases up to 10.5. One embodiment of the method includes inoculating one or more of the fungal species and/or strain(s) into artificial media and growing the fungal species and/or strain(s) to produce filamentous biomass which contains one or more useful products.

The filamentous fungi biomats produced arise from anaerobic, microaerobic, aerobic conditions of a combination thereof via surface fermentation. The filamentous fungi biomats comprise the fungal species and/or strain and/or progeny thereof in the form of conidia, microconidia, macroconidia, pycnidia, chlamydospores, hyphae, fragments of hyphae, or any and all combination thereof.

Also provided are methods for harvesting the filamentous fungi biomats, isolation and/or purification of useful proteins, amino acids, and/or lipids produced by the filamentous fungi. These proteins, amino acids, and/or lipids can be used in food, fish feed, animal feed, oils, fatty acids, medicinals, nutraceuticals, fungicides, herbicides, yeasticides, insecticides, biolubricants, and as a feedstock for conversion to other value added products.

BRIEF DESCRIPTION OF THE DRAWINGS

FIG. 3A: Loop showing white mycelial mat collected from $2^{nd}$ generation archive culture; FIG. 3B: Petri plate with strain MK7 mycelial mat.

FIG. 4. Growth and pH of strain MK7 culture in 10 L bioreactor to be used for inoculation of tray reactors. MK7-1 liquid medium at 7.5% glycerol content with a C:N ratio of 7.5:1. Optimal culture for using as inoculum is generated between 72 and 90 hours when the biomass is in the late exponential growth phase (between arrows).

FIGS. 10A, 10B: 50× zoom showing three layers: aerial hyphae layer, transition zone layer, and dense bottom layer; FIG. 10C: 50× zoom showing two distinct layers.

FIG. 11A: Top surface of strain MK7 biomat revealing aerial hyphae and mycelia extending out from dense mycelial layer. Image generated using transmitted light microscope at 100× magnification; FIG. 11B: Top surface of strain MK7 biomat revealing aerial hyphae and mycelia extending out from dense mycelial layer. Image generated using transmitted light microscope at 400× magnification; FIG. 11C: Bottom surface of strain MK7 biomat revealing hyphae and mycelia. Image generated using transmitted light microscope at 400× magnification; FIG. 11D: Dense interior of strain MK7 biomat revealing its intertwined fibrous composition. Image generated using transmitted light microscope at 400× magnification.

DETAILED DESCRIPTION

Definitions

Figure 1:
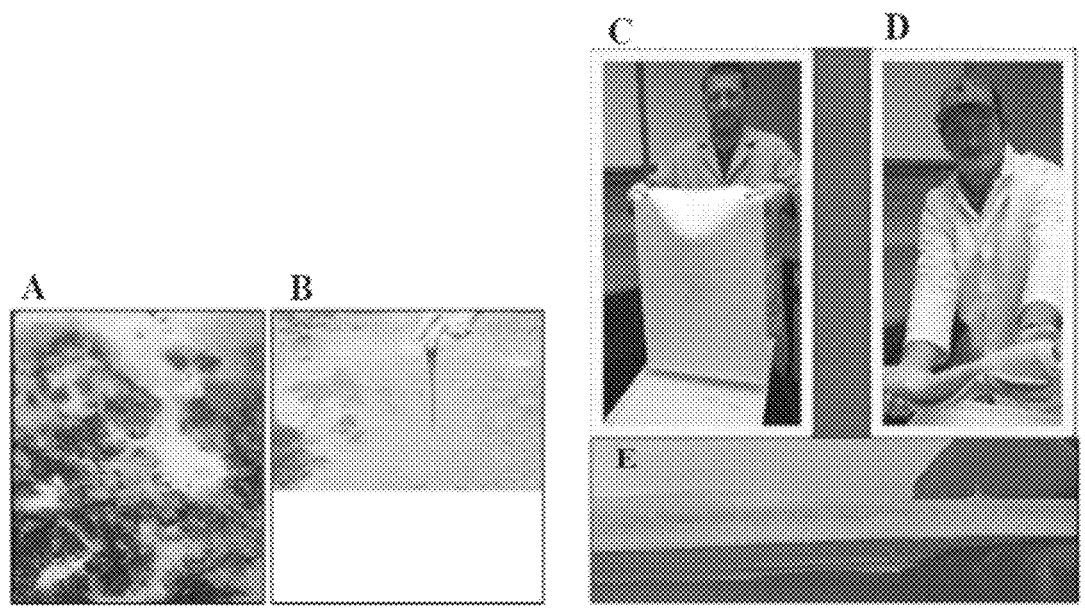
FIG. 1. A, B: strain MK7 in nature in a hot spring environment at Yellowstone National Park; C, D: strain MK7 biomass produced under distinct artificial conditions showing high density, high tensile strength cohesive pure biomass; E: cross section of strain MK7 biomass of C, D.

As used herein, the verb "comprises," and its conjugations are used in this description and in the claims, in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "derived from" refers to the origin of source, and may include naturally occurring, recombinant, unpurified, or purified molecules. A fungus derived from a specific, isolated fungal strain and/or its progeny may comprise certain mutations but still retain one, two or more, or all of the distinguishing morphological and physiological characteristics of the isolated fungi or its progeny from which it was derived.

As used herein, the term "acidophilic" refers to an organism whose optimal growth conditions are under acidic conditions.

As used herein, the term "feedstock" refers to any renewable, biological material that can be used directly as a fuel, or converted to another form of fuel or energy product. Biomass feedstocks are the plant and algal materials used to derive fuels like ethanol, butanol, biodiesel, and other hydrocarbon fuels.

As used herein, the phrase "lignocellulosic feedstocks" refers to feedstocks containing lignocellulose. Non-limiting examples of lignocellulosic feedstocks include, agricultural crop residues (e.g., wheat straw, barley straw, rice straw, small grain straw, corn stover, corn fibers (e.g., corn fiber gum (CFG), distillers dried grains (DDG), corn gluten meal (CGM)), purpose grown grass crops, energy crops, switchgrass, hay-alfalfa, sugarcane bagasse), corn steep liquor, beet pulp non-agricultural biomass (e.g., algal mats, urban tree residue), corn steep liquor, beet pulp, forest products and industry residues (e.g., softwood first/secondary mill residue, hard softwood first/secondary mill residue, recycled paper pulp sludge), lignocellulosic containing waste (e.g., newsprint, waste paper, brewing grains, municipal organic waste, yard waste, clinical organic waste, waste generated during the production of biofuels (e.g., processed algal biomass, glycerol, residues from the production of cellulosic ethanol, solid residues from biodiesel production), and a combination thereof.

As used herein, unless otherwise specified, the term "carbohydrate" refers to a compound of carbon, hydrogen, and oxygen that contains a aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment they are monosaccharides. In another embodiment they can be pyranose and furanose sugars. They can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sufinyl, sulfamonyl, ester, carboxylic acid, amide, phosphonyl, phosphinyl, phosphoryl, thioester, thioether, oxime, hydrazine, carbamate. These saccharide units can be arranged in any order and the linkage between two saccharide units can occur in any of approximately ten different ways. As a result, the number of different possible stereoisomeric oligosaccharide chain is enormous. In one embodiment, said carbohydrates are selected from the group consisting of monosaccharides, disaccharides, oligosaccharides, polysaccharides, and a combination thereof.

As used herein, the term "monosaccharide" refers to sugar monomers selected from the group consisting of three-carbon sugars (trioses), four-carbon sugars (tetroses), five-carbon sugars (pentoses), six-carbon sugars (hexoses), etc., and a combination thereof. In one embodiment, the five-carbon sugars are selected from the group consisting of ketopentose (e.g., ribulose, xylulose), aldopentose (ribose, arabinose, xylose, lyxose), deoxy sugar (deoxyribose), and a combination thereof. In one embodiment, the six-carbon sugars are selected from the group consisting of aldohexoses (e.g., allose, altrose, glucose, mannose, idose, galactose, talose), cyclic hemiacetals, ketohexoses (e.g., psicose, fructose, sorbose, tagatose). In one embodiment, said monosaccharides are selected from the group consisting of trioses, tetroses, pentoses, hexoses, heptoses, etc., and a combination thereof.

In one embodiment, the monosaccharides are in linear form; in another embodiment, the monosaccharides are in cyclic form.

As used herein, the phrase "fermentable sugars" refers to sugar compounds that can be converted to useful value-added fermentation products, non-limiting examples of which include amino acids, proteins, sugars, carbohydrates, lipids, nucleic acids, polyketides, vitamins, pharmaceuticals, animal feed supplements, specialty chemicals, chemical feedstocks, plastics, solvents, fuels, or other organic polymers, lactic acid, and ethanol. Specific value-added products that may be produced by the methods disclosed, but are not limited to, β-glucan, lactic acid; specialty chemicals; organic acids, including citric acid, succinic acid and maleic acid; solvents; fish feed and animal feed supplements; pharmaceuticals; vitamins; amino acids, such as lysine, methionine, tryptophan, threonine, carotenoids, human food, nutraceutical, and aspartic acid; industrial enzymes, such as proteases, cellulases, amylases, glucanases, lactases, lipases, lyases, oxidoreductases, transferases and xylanases; and chemical feedstocks.

As used herein, the term "fungus" or "fungi" refers to a distinct group of eukarotic, organisms with absorptive nutrition and lacking chlorophyll.

As used herein, the term "acidification material" refers to any materials, chemical compounds, agents, and/or compositions which when added into a solvent (e.g., water), gives a solution with a hydrogen ion activity greater than in pure solvent (e.g., water). The material can be in gas, liquid, or solid form. The material can be organic and/or inorganic. Non-limiting examples of acidification material include any material that comprises hydrogen halides and their solutions (e.g., hydrochloric acid (HCl), hydrobromic acid (HBr), and hydroiodic acid (HI)), halogen oxoacids (e.g., hypochloric acid, chloric acid, perchloric acid, periodic acid and corresponding compounds for bromine and iodine), sulfuric acid ($H_2SO_4$), fluorosulfuric acid, nitric acid ($HNO_3$), phosphoric acid ($H_3PO_4$), fluoroantimonic acid, fluoroboric acid, hexafluorophosphoric acid, chromic acid ($H_2CrO_4$), sufonic acids, methanesulfonic acid (aka mesylic acid, $MeSO_3H$), ethaneslfonic acid (aka esylic acid, $EtSO_3H$), benzenesulfonic acid (aka besylic acid, $C_6H_5SO_3H$), p-toluenesulfonic acid (aka tosylic acid $CH_3C_6H_4SO_3H$), trifluoromethanesulfonic acid (aka triflic acid, $CF_3SO_3H$), carboxylic acids (e.g., acetic acid, citric acid, formic acid, gluconic acid, lactic acid, oxalic acid, tartaric acid, Vinylogous carboxylic acids (e.g., ascorbic acid, meldrum's acid), acid salts (e.g., sodium bicarbonate ($NaHCO_3$), sodium hydrosulfide (NaHS), sodium bisulfate ($NaHSO_4$), monosodium phosphate ($NaH_2PO_4$), and disodium phosphate ($Na_2HPO_4$)).

As used herein, the term "neutralize," "neutralizing," and "neutralization" refers to a chemical reaction in aqueous solutions, wherein an acid and a base react to form water and salt, and wherein the pH of the solution is brought back to an initial pH.

As used herein, the term "manganese donor" refers to a composition or compound which can provide manganese ion (e.g., manganese (I), manganese (II), and manganese (III)) in an aqueous solution. Non-limiting examples of manganese donors include, $Mn_2(CO)_{10}$, $K_5Mn(CN)_6NO$, $MnCl$, $MnF_2$, $MnBr_2$, MnO, $MnO_2$, MnCh, $MnF_3$, $MnBr_3$, $MnCO_3$, $Mn(CH_3COO)_2$, $C_6H_9MnO_6$, $MnTiO_3$, $[CH_3COCH=C(O)CH_3]_2Mn$, $[C_6H_{11}(CH_2)_3CO_2]_2Mn$, $(HCO_2)_2Mn$, $Mn(C_5H_1F_6O_2)_2$, $Mn(PH_2O_2)_2$, MnI, $(C_3H_5O_3)_2Mn$, $MnMoO_4$, $Mn(NO_3)_2$, $Mn(ClO_4)_2$, $C_{32}H_{16}MnN_8$, $MnSO_4$, $(CH_3COO)_3Mn$, $C_{32}H_{16}ClMnN_8$, $C_{48}H28ClMnN4O_8$, $C_5H_4CH_3Mn(CO_3)$, $Mn(C_5H_4C_2H_5)_2$, and $C_{16}H_{22}Mn$.

As used herein, the term "pH buffering materials" refers to the compositions that when added in a liquid mixture, can maintain the pH of said liquid mixture wherein the pH is kept around about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0. For example, the pH of the liquid mixture is in a range between about 0.5 to about 3.0. The preferred pH for the filamentous acidophic MK7 strain is about 2.2 to about 3.0. Such composition can comprise compounds such as acid, acid salts, basic and basic salts, for example, HCl, $H_2NO_3$, $H_2SO_4$, $NaHCO_3$, NaHS, $NaHSO_4$, $NaH_2PO_4$, $Na_2HPO_4$, $NaHSO_3$, $KHCO_3$, KHS, $KHSO_4$, $KH_2PO_4$, $K_2HPO_4$, $KHSO_3$. NaOH, KOH, $Mg(OH)_2$, $Na_2CO_3$, $K_2CO_3$, $KHCO_3$, $CaCO_3$, $MgCO_3$, $Na_2S$, $K_2S$, etc.

As used herein, the term "aerobic conditions" refers to conditions where sufficient oxygen, is provided, and anaerobic respiration in a microorganism growing under such conditions is prohibited and anaerobic metabolic pathways are inhibited preventing anaerobic respiration.

As used herein, the term "microaerobic" and "microaerophilic" are used interchangeably to refer to conditions wherein the supply of oxygen is limited, but the cellular respiration in an organism is dominantly aerobic respiration.

As used herein, the term "fatty acids" refers to long-chained molecules having a methyl group at one end and a carboxylic acid group at the other end.

As used herein, the term "isolated fungus" refers to any composition comprising a fungus population which is obtained from a natural source.

As used herein, the term "carbon source" generally refers to a substance suitable to be used as a source of carbon for prokaryotic or eukaryotic cell growth. Carbon sources include, but are not limited to, biomass hydrolysates, acid whey, sweet whey, carbohydrates (e.g., starch, sucrose, polysaccharides, and monosaccharides), cellulose, hemicellulose, xylose, and lignin, as well as monomeric components of these substrates and/or combinations thereof. Carbon sources can comprise various organic compounds in various forms, including but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. A carbon source can also be a feedstock or lignocellulosic feedstock, such as sugar beet pulp. Photosynthetic organisms can additionally produce a carbon source as a product of photosynthesis.

As used herein, the term "biocatalyst" refers to a living system or cell of any type that speeds up chemical reactions by lowering the activation energy of the reaction and is neither consumed nor altered in the process. Biocatalysts may include, but are not limited to, microorganisms such as yeasts, fungi, bacteria, and archaea. For example, the isolated fungal species and/or strain(s) of the present invention can be used as a biocatalyst in the production of proteins and lipids, or in the degradation of carbon substrates or organic molecules for the production of proteins and lipids.

As used herein, the term "fermentation" or "fermentation process" refers to a process in which an organism or a biocatalyst is cultivated in a culture medium containing raw materials, such as a carbon source and nutrients, wherein the organism or biocatalyst converts those raw materials into products.

As used herein, the term "biomass" refers to biological material derived from living, or recently living organisms, e.g., stems, leaves, and starch-containing portions of green plants, or wood, waste, forest residues (dead trees, branches and tree stumps), yard clippings, wood chips, or materials derived from algae or animals and/or industrial byproducts and waste streams, food waste/scraps, and other simple sugars. In some cases, biomass contains a significant portion of protein and/or lipid. In other cases, it is mainly comprised of starch, lignin, pectin, cellulose, hemicellulose, and/or pectin.

As used herein, the term "cellulosic biomass" refers to biomass composed primarily of plant fibers that are inedible or nearly inedible by humans and have cellulose as a prominent component. Those fibers may be hydrolyzed to yield a variety of sugars that can be fermented by microorganisms. Examples of cellulosic biomass include grass, wood, and cellulose-rich residues resulting from agriculture or the forest products industry.

As used herein, the terms "filamentous biomat," and "filamentous fungi biomat" are used interchangeably and refer to biomats produced by and containing filamentous fungi.

As used herein, the term "starch" refers to a polymer of glucose readily hydrolyzed by digestive enzymes, e.g., amylases. Starch is usually concentrated in specialized portions of plants, such as potatoes, corn kernels, rice grains, wheat grains, and sugar cane stems.

As used herein, the term "lignin" refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

As used herein, the term "cellulose" refers to a long-chain polymer polysaccharide carbohydrate of beta-glucose of formula $(C_6H_{10}O_5)_n$, usually found in plant cell walls in combination with lignin and any hemicellulose.

As used herein, the term "hemicellulose" refers to a class of plant cell-wall polysaccharides that can be any of several heteropolymers. These include xylan, xyloglucan, arabinoxylan, arabinogalactan, glucuronoxylan, lucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction. Proportions of each of the monosaccharides in relation to D-galacturonic acid vary depending on the individual plant and its micro-environment, the species, and time during the growth cycle. For the same reasons, the homogalacturonan and RG-I fractions can differ widely in their content of methyl esters on GalA residues, and the content of acetyl residue esters on the C-2 and C-3 positions of GalA and neutral sugars.

As used herein, the term "facultative anaerobic organism" or facultative anaerobic microorganism" or a "facultative anaerobic biocatalyst" is defined as an organism that can grow in wither the presence or in the absence of oxygen, such as the fungal strains isolated in the present invention.

As used herein, the term "distillers dried grains", abbreviated as DDG, refers to the solids remaining after a fermentation, usually consisting of unconsumed feedstock solids, remaining nutrients, protein, fiber, and oil, as well as biocatalyst cell debris. The term may also include soluble residual material from the fermentation and is then referred to as "distillers dried grains and solubles" (DDGS).

As used herein, the term "nutrient" is defined as a chemical compound that is used by an organism or biocatalyst to grow and survive. As an example, nutrients can be organic compounds such as carbohydrates and amino acids or inorganic compounds such as metal salts.

As used herein, the term "complex nutrient" is defined a nutrient source containing mostly monomeric organic compounds used by an organism or biocatalyst for the production of proteins, DNA, lipids, and carbohydrates. The term "rich nutrient" is used interchangeably throughout with the term complex nutrient. Typically, complex nutrients or rich nutrients are derived from biological materials, such as slaughterhouse waste(s), dairy waste(s), or agricultural residues. Complex nutrients or rich nutrients include, but are not limited to: yeast extract, tryptone, peptone, soy extract, corn steep liquor, soy protein, and casein.

As used herein, the term "aerobic metabolism" refers to a biochemical process in which oxygen is used to make energy, typically in the form of ATP, from carbohydrates. Typical aerobic metabolism occurs via glycolysis and the TCA cycle, wherein a single glucose molecule is metabolized completely into carbon dioxide in the presence of oxygen.

As used herein, the phrase "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and fermentation, in which the electrons from NADH are utilized to generate a reduced product via a "fermentative pathway."

As used herein, the term "microbiological fermentation" refers to a process where organic substances are broken down and re-assembled into products by microorganisms. The substances may include, but are not limited to, glucose, sucrose, glycerol, starch, maltodextrine, lactose, fats, hydrocarbons, protein, ammonia, nitrate, and phosphorus sources. The products may include, but not limited to, specialty products (including but not limited to, mycoprotein products, soy products, tempeh, etc.), traditional products (including but not limited to, bread, beer, wine, spirits, cheese, dairy products, fermented meats and vegetables, mushrooms, soy sauce and vinegar), agricultural products (including but not limited to, gibberellins, fungicides, insecticides, silage, amino acids such as L-Glutamine, L-Lysine, L-Tryptophan, L-Throenine, L-aspartic (+), L-arylglycines), enzymes (including but not limited to carbohydrates, celluloses, lipases, pectinases, proteases), fuels and chemical feedstocks (including but not limited to, acetone, butanol, butanediol, isopropanol, ethyl alcohol, glycerol, methane, glycerol, butyric acid, methane, citric acid, fumaric acid, lactic acid, propionic acid, succinic acid, and L-glutaric acid or salts of any of these acids), nucleotides, organic acids, pharmaceuticals and related compounds (including but not limited to alkaloids, antibiotics, hormones, immunosuppressant, interferon, steroids, vaccines, vitamins) and polymers (including but not limited to alginates, dextran, gellan, polyhydroxybutyrate, scleroglucan and xanthan). The microorganisms used for fermentation may include both prokaryotic microorganisms (including bacteria, cyanobacteria) and eukaryotic microorganisms (including yeast, fungi and algae).

As used herein, the phrase "energy crops" refers to plants grown as a low cost and low maintenance harvest used to make biofuels, or directly exploited for its energy content. Commercial energy crops are typically densely planted, high yielding crop species where the energy crops will be burnt to generate power. Woody crops such as Willow or Poplar are widely utilized as well as tropical grasses such as *Miscanthus* and *Pennisetum purpureum* (bout known as elephant grass).

As used herein, the term "surface fermentation" refers to those fermentations in which the microorganisms employed grow on the surface of the fermentation media without any further support. The media is typically a free-flowing aqueous media. Without being bound by theory, it is thought that filamentous biomats result from some combination of aerobic, microaerobic and/or anaerobic metabolism. For example, the surface of the biomat is thought to rely on aerobic respiration while the bottom of the biomat may be microaerobic to highly anaerobic.

As used herein, the term "solid substrate surface fermentation" refers to those fermentations in which the microorganisms employed grow on the surface of the fermentation media using carbon and nutrients supplied by solids that are submerged in the fermentation media. In some embodiments, some portion of the biomat may be partially submerged.

As used herein, the term "submerged fermentation" refers to those fermentations wherein the microorganisms employed grow in a submerged state within fermentation media. Many fermentations fall within this category, such as the penicillin submerged fermentation technique.

As used herein, the term "solid-state fermentation" refers to the culture of microorganisms grown on a solid support selected for the purpose. For example, a solid culture substrate, such as rice or wheat bran, is deposited on flatbeds after seeding with microorganisms; the substrate is then left in a temperature-controlled room for several days. Solid-state fermentation uses culture substrates with low water levels (reduced water activity). The medium (e.g. rice or wheat bran) is saturated with water, but little of it is free flowing. The solid medium comprises both the substrate and the solid support on which the fermentation takes place.

As used herein, the term "nutraceutical" refers to substances that have health or medicinal benefits. In some instances, a nutraceutical not only supplements the diet but also aids in the prevention and/or treatment of disease and/or disorders. The term "nutraceutical" was coined from "nutrition" and "pharmaceutical" in 1989 by Stepen DeFelice, MD, founder and chairman of the Foundation for Innovation in Medicine (FIM).

As used herein, "progeny" refers to any and all descendants by lineage which originate from a strain no matter however or wherever produced. Included within the definition of "progeny" as used herein are any and all mutants of the isolated/deposited strain and its progeny, wherein such mutants have at least one of the physiological and/or morphological characteristics of the isolated/deposited strain and its progeny.

Artificial Media for Growth of Filamentous Fungi Biomat

An artificial media is used to produce a filamentous fungal biomat. The artificial media provides the nutrients required for increased cell cycle times as compared to those found in nature (i.e. increased growth rate) and results in increased cell density. The artificial media comprises at least the following macronutrients: nitrogen (N), phosphorus (P), calcium (Ca), magnesium (Mg), carbon (C), potassium (K), sulfur (S). Trace nutrients such as iron (Fe), boron (B), chromium (Cr), copper (Cu), selenium (Se), manganese (Mn), molybdenum (Mo), vanadium (V), and zinc (Zn) can also be added to the media to supplement carbon sources. Carbon sources such as lignocellulosic feedstocks, sweet whey, and/or acid whey typically provide sufficient trace nutrients so that additional trace nutrients are not required.

Additional nutrient additions can be added to the artificial media. Examples of such are carbohydrates (e.g., monosaccharides, polysaccharides), amino acid donors (e.g., amino acid, polypeptides), and combinations thereof. In addition, compounds that can facilitate pretreatment of the lignocellulosic carbon source can also be added into the artificial media. Such compounds include, but are not limited to, acidification materials, manganese donors, nutrients, and pH buffering material.

The artificial medium can be in the form of a liquid impregnated solid, a liquid, or a gel. The artificial medium can also be in the form of a liquid covering a solid carbon substrate, such as a lignocellulose feedstock or other solid carbon substrate. Here, the solid substrate is submerged under the surface of a liquid, such that the biomat grows on the surface of the liquid using carbon derived from the submerged solid, a process known as solid substrate surface fermentation (SSSF). Extracellular enzymes excreted from the fungus degrade the solid carbon substrate, releasing soluble carbon that can be taken up by the biomat at or near the biomat/water interface. The resulting biomat forms a mat on a liquid layer above the submerged solid substrate. In general, the liquid layer above the submerged carbon source should be about 0.01-1.0 cm deep. Too little liquid results in no mat formation and solid-state fermentation and/or submerged fermentation ensues. Too much liquid results in inefficient conversion and a depressed biomat growth cycle.

There are a large variety of substances that can be used as a carbon source for the artificial media. These include sugars (e.g., glucose, galactose, mannose, trehalose, sucrose, arabinose, mannose, xylose, fructose, etc.), glycerol, starch, carbohydrates, glycerol, whey, lignocellulosic feedstock, waste stream(s) (e.g. acid whey) and combinations thereof. Suitable lignocellulosic feedstocks include, for example, switchgrass, energy crops, forest hardwoods and other products, brewers spent grain, wheat straw, grasses, leaves, AFEX crop residues, anaerobic digestate, agricultural crop residues (e.g., barley straw, rice straw, small grain straw, corn stover, corn fibers (e.g., corn fiber gum (CFG), distillers dried grains (DDG), corn gluten meal (CGM)), hay-alfalfa, sugarcane bagasse, non-agricultural biomass (e.g., algal mats, urban tree residue), industry residues (e.g., softwood first/secondary mill residue, hard softwood, first/secondary mill residue, recycled paper, pulp sludge), lignocellulosic containing waste (e.g., newsprint, waste paper, brewing grains, municipal organic waste, yard waste), clinical organic waste, waste generated during the production of biofuels (e.g., processed algal biomass, residues from the production of cellulosic ethanol, solid residues from biodiesel production), and a combination thereof. Suitable waste stream(s) include agricultural waste, municipal organic wastes, waste from biofuel production (e.g., cellulosic ethanol production residues), algal biomass, brewers spent grain and/or waste streams (e.g., molasses, corn syrup, etc.), industrial waste (e.g., organic molecules such as phenol and other aromatics) and fibers such as beta-glucan, cellulose, chitin, hemicellulose and polydextros, monosaccharides, disaccharides, oligosaccharides, polysaccharides, and any combination thereof. The monosaccharides encompass trioses, tetroses, pentoses, hexoses, heptoses, etc., and any and all combinations thereof, the pentoses encompass ribulose, xylulose, ribose, arabinose, xylose, lyxose, deoxyribose, and any and all combinations thereof, while the hexoses are selected from the group consisting of allose, altrose, glucose, mannose, glucose, idose, galactose, talose, psicose, fructose, sorbose, tagatose, and any and all combinations thereof. The disaccharides encompass sucrose, lactose, maltose, and any and all combinations thereof while the polysaccharides encompass starch, glycogen, cellulose, chitin, and any and all combinations thereof.

The carbon source that is used to grow the isolated fungal strain can comprise cellulose in an amount of from about 5% to about 100%, from about 10% to about 95%, from about 20% to about 90%, from about 30% to about 85%, from about 40% to about 80%, from about 50% to about 75%, or from about 60% to about 70% by dry weight of the carbon source. Alternatively, the cellulosic carbon source comprises cellulose in an amount of at least about 5%, at least about 10%, at least about 20%, at least about 30%, at least about 40%, at least about 50%, at least about 60%, or at least about 70% of the dry weight of the carbon source. In other cases, the cellulosic carbon source used to grow the isolated fungal strain comprises from about 1% to about 50%, from about 5% to about 40%, or from about 10% to about 30% by weight of a component selected from lignin, hemicellulose, or a combination thereof. In some embodiments of the present invention, the cellulosic carbon source used to grow a microorganism comprises at least about 1%, at least about 5%, at least about 10%, at least about 20%, or at least about 30% by weight of a component selected from lignin, hemicellulose, or a combination thereof.

Suitable nitrogen sources include urea, ammonium nitrate ($NH_4NO_3$), ammonium sulfate ($NH_4SO_4$), nitrate salts (e.g. $KNO_3$), ammonia salts (i.e. $NH_4SO_4$) and organic N (e.g. proteins, peptides), industrial waste streams high in nitrogen, corn steep liquor, and combinations thereof. Artificial media prepared with a pure urea nitrogen source provides approximately 25% faster growth of the filamentous fungi than does artificial media prepared with a combination of urea and ammonium nitrate (i.e. 70 $g/m^2$/day vs. 52 $g/m^2$/day, respectively). Combinations of urea and ammonium nitrate can also be used. Growth, albeit much slower than that produced with urea alone or a urea combination, also occurs when ammonium sulfate is used as the sole nitrogen source. While ammonium nitrate alone can also be used, this nitrogen source again does not produce the vigorous growth seen with combinations of urea.

Manipulation of the carbon to nitrogen ration (C:N) within the artificial media has a significant influence on the composition of the biomat produced by the fungal species and/or strain(s). Typically, a low C:N ratio, such as a C:N ratio of 7.5:1 or less, favors production of proteins and amino acids as compared to lipids. On the other hand, a C:N ratio of more than 7.5:1 favors production of lipids as compared to proteins. Oftentimes lipid formation is particularly favored when the artificial media has a C:N ratio of at least 10:1, 15:1, 20:1, 26:1, 30:1, 40:1, or 50:1.

The pH of the artificial media is determined based on the products desired and the fungal species and/or strain(s) employed. *Fusisporium, Pseudofusarium, Gibberella, Sporotrichella, Aspergillus, Penicillium, Triocoderma*, species within the *Mucorales* sp. (e.g., *Rhizopus* sp.), the isolated filamentous acidophilic fungal strain designated as MK7, and combinations thereof, high lipid production takes place over pH range 2.0-7.0 and optimally at a pH of less than 3.5. High protein production, while predominantly influenced as a function of C:N ratios, requires a pH of at least 2.7 and preferably a pH between 4.5 and 5.5.

Cultures and Compositions Comprising Isolated Fungal species and/or strains

The present invention uses a pure culture of an isolated fungal species and/or strain, or a pure co-culture of two fungal species and/or strains, or comprised of a substantially pure culture of three or more fungal species and/or strains. A large number of isolated filamentous fungal species and/or strains can be used, such as a species and/or strain(s) of *Fusisporium, Psedofusarium, Gibberella, Sporotrichella, Aspergillus. Penicillium, Triocoderma, Pichia* spp, species within the *Mucorales* sp. (e.g. *Rhizopus* sp.), and combinations thereof. The biologically pure culture/co-culture/substantially pure culture can also comprise the isolated filamentous acidophilic fungal strain designated as MK7, which has been deposited as ATCC Accession Deposit No. PTA-10698, or active mutants thereof. Biologically pure cultures of genetically modified filamentous fungi can also be used. The pure fungal species and/or strain(s) and/or its progeny are typically in the form of conidia, microconidia, macroconidia, pycnidia, chlamydospores, hyphae, fragments of hyphae and mycelia or a combination thereof.

The filamentous acidophilic MK7 fungal strain is a new strain of acidophilic fungus, which can directly convert carbon sources such as lignocellulosic carbon sources, carbohydrates, (e.g., acid whey) and algal biomass to filamentous fungi biomats comprising proteins and lipids.

Methods of producing useful products using the artificial media and the isolated fungus stain and/or its progeny, comprise:

a) Inoculating one or more of the fungal species or strains and/or its progeny into artificial media having a carbon source selected from the group consisting of sugar, glycerol, lignocellulosic feedstocks, carbon containing agricultural, industrial, and municipal waste products, carbohydrates, yeast extract, casamino acids, acid whey, sweet whey and/or a combination thereof in a container, wherein the artificial media can support the growth of said isolated fungal strain via surface fermentation;

b) growing said isolated fungal strain in said artificial media to produce filamentous fungi biomats;

c) harvesting the filamentous fungi biomats; and d) optionally isolating, purifying and/or producing products from the filamentous fungi biomats.

Growth is produced under aerobic conditions. In another embodiment the growth is produced under microaerobic conditions. Alternatively, growth is produced as the result of any combination of aerobic conditions, microaerobic conditions and anaerobic conditions, such as via surface fermentation.

The useful products are protein-rich biomass, biomats and/or a filamentous fungi biomat. For example, the useful products produced using the fungi and methods disclosed include, but are not limited to, protein biomats for use in food products, fish feed products, animal feed products, bioplastics, and/or precursors thereof. Here, the growth is produced by aerobic conditions, microaerobic conditions, and anaerobic conditions or any combination thereof.

A large number of the acidophilic fungal species and/or strain(s), such as *Fusisporium, Pseudofusarium, Gibberella, Sporotrichella, Aspergillus. Penicillium, Triocoderma*, species within the *Mucorales* sp. (e.g., *Rhizopus* sp.), the isolated filamentous acidophilic fungal strain designated as MK7 and combinations thereof, and/or their progeny can be cultured in the absence of antibiotics with little or no contamination. Typically, contamination in the artificial media is caused by other organisms such as bacteria, other undesired fungi (e.g., yeasts, molds), algae, plants, insects, and a mixture thereof.

At least one composition comprising an isolated fungal species and/or strain of *Fusisporium, Pseudofusarium, Gibberella, Sporotrichella, Aspergillus. Penicillium, Triocoderma*, species within the *Mucorales* sp. (e.g., *Rhizopus* sp.), yeasts capable of producing filaments (i.e. *Yarrowia*) the isolated filamentous acidophilic fungal strain designated as MK7, and combinations thereof is also disclosed. The composition can further comprise an artificial medium that supports growth of the fungal species and/or strain(s), and optionally one or more of an acidification material, a manganese donor, a nutrient addition, and/or a mixture thereof.

Surface Fermentation

The current disclosure initiates surface fermentation by inoculating artificial media with a suspension of planktonic cells of the desired filamentous fungal species and/or strain(s). Inoculum culture from an inoculum reactor is added to the artificial media at a concentration that will produce a mature biomat in the desired period of time. In theory, the media could be inoculated with a single cell; however, such an inoculation would require extraordinarily stringent sterility conditions and a significantly extended period of time in order for mature biomat to develop. Typically, inoculation with 0.5-1.0 g of cells per liter of growth media will produce a biomat in 3 to 6 days. For example, adding inoculum containing about 10 g/L of cells at 7.5% (volume to volume) of the medium used will produce a biomat in 3 to 6 days. No external oxygen is introduced to the artificial media by bubbling or other means, sufficient oxygen can be culled from ambient or near ambient conditions.

Without being bound by theory, it is thought that because cell growth is much more rapid in the presence of oxygen, conidia present at the surface of the artificial media where more oxygen is present will grow rapidly and begin formation of the mycelial biomat. It is believed that oxygen concentrations are much lower only a few micrometers below the surface of the artificial media and consequently would place fungal cells located in those regions in a stress environment. Stress is known to increase excretion of extracellular polysaccharides, which have a "sticky" phenotype, and would thus aid in the rapid formation of the filamentous fungi biomat by adhering to the cells proliferating at the surface. Substrate concentration, however, also has a significant effect. For example, when the carbon substrate concentration is below 4%, filamentous fungi biomats will not form. It should be noted that initial environmental stress to form mats does not necessarily infer that a stressed mat, i.e. a mat containing toxins excreted by the stressed organism is formed.

Typically, shallow trays containing artificial media are used for surface fermentation under controlled conditions of temperature, humidity, and airflow suitable for the fungal species and/or strains(s) employed. Sterile conditions are maintained for optimal filamentous fungi biomat growth. Sufficient airflow is maintained to remove heat and carbon dioxide produced from microbial respiration and supply oxygen without agitating the surface of the artificial media and disrupting fungal hyphae growth.

In general, a "skin" begins to form on the surface of the artificial media on day 2 after inoculation. This "skin" is the initial filamentous fungi biomat which frequently includes aerial hyphae as well as hyphae in contact with the artificial media and which continues to grow and increase in cell density. Typically, three to six days after inoculation, the resultant filamentous fungi biomats are 1 to 30 mm thick and have sufficient tensile strength and structural integrity to be handled without tearing.

The filamentous fungi biomats produced have a structure as described which is not seen in nature. First, naturally formed filamentous fungi biomats are not composed of a pure culture/co-culture/substantially pure culture. Typically, the biomats formed in nature contain various types of algae and/or bacteria in addition to at least one filamentous fungal species and form an artificial microecosystem. Examples of fungal biomats formed in nature are mycorrhizal fungal mats, which exist in a largely dispersed form in the soil and are associated with plant roots, lichens (e.g. Reindeer moss and crustose lichen), and mushrooms (e.g. *Armillaria ostoyae*).

Second, the biomats formed using the methods and techniques described herein have a significantly greater cell density than those found in nature, even taking into account the multiple species found in naturally formed biomats. The produced filamentous fungi biomats tend to be very dense typically, 50-200 grams per liter. Natural and submerged processes for growth of filamentous fungi commonly result in biomass densities of about, 15 grams per liter. Solid-state fermentation processes result in a mixture of the substrate with a small percentage of fungi, i.e. less than 5% fungal composition. From the perspective of percent solids, the methods disclosed herein produced filamentous fungi biomats that commonly range from 5-20% solids. In contrast, natural and submerged processes for growth of filamentous fungi commonly result in percent solid ranges of less than 1.5%. One result of the densities achieved, the filamentous nature, and the extracellular matrix found in these dense biomats is an ability to be maintained as a cohesive mat upon drying. This is in stark contrast to the powdery and/or non-cohesive form normally found with other dried filamentous fungi biomats.

Third, the biomats formed using the methods and techniques described herein have a high tensile strength compared to naturally occurring biomats, allowing them to be lifted and moved without breakage.

Figure 10A:
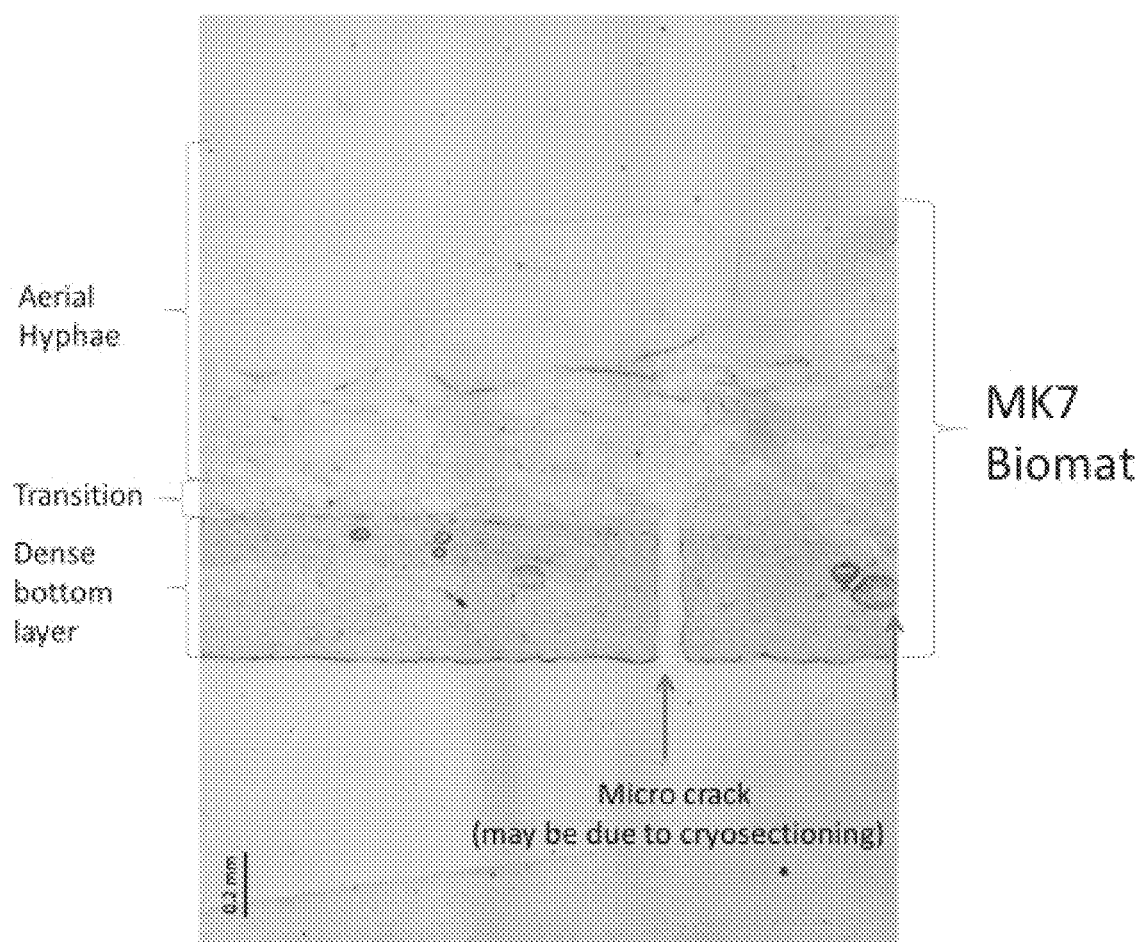
FIGS. 10A-10C. Transmitted light microscopic images of cross sections of 5 days old MK7 biomats produced using MK7-1 medium+glycerol.
Figure 10B:
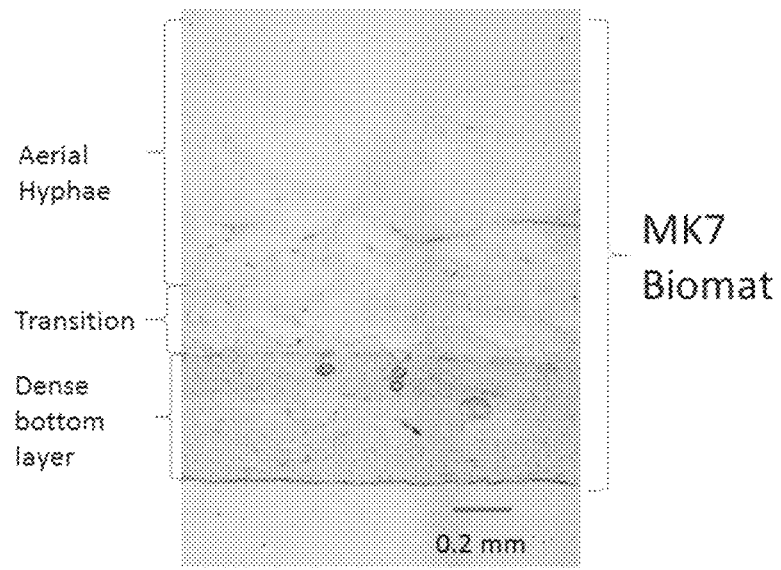
Figure 10C:
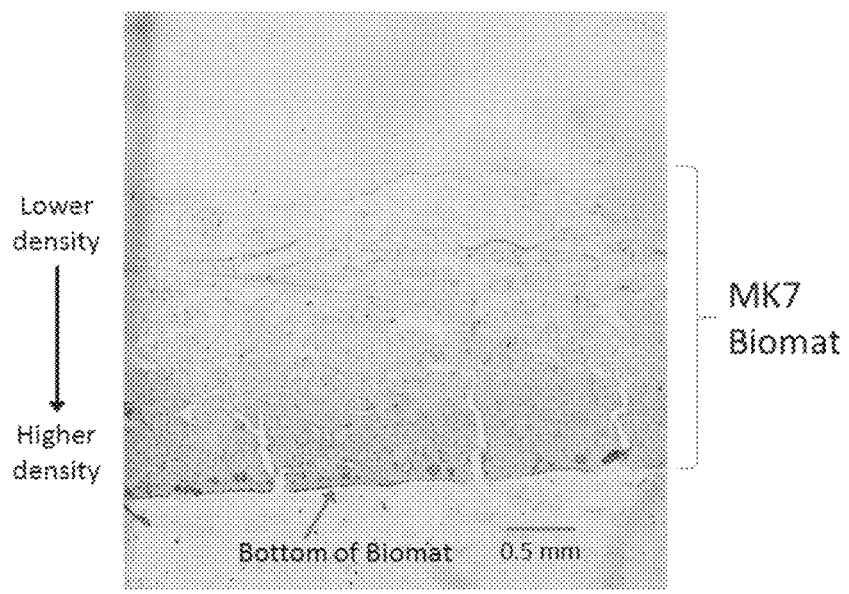

Fourth, the instant biomats have a defined structure comprising, in some instances, a single dense layer comprised of long filaments generally aligned parallel to the air:biomat interface. In some filamentous fungi biomats at least two layers exist: (a) a dense bottom layer and (b) an aerial hyphae layer. In some filamentous fungi biomats at least three structurally different layers are visible: (a) a dense bottom layer, (b) an aerial hyphae layer and (c) a transition zone layer (see FIGS. 10A and B). For systems with aerial hyphae and systems with three layers, the aerial hyphae layer is typically most visibly dominant, followed by the dense bottom layer, while the transition zone layer, if present, is smallest. Each of the layers normally has a characteristic cell density associated with it as compared to the other layer(s). For example, the aerial hyphae layer is significantly less dense than the bottom layer of the biomat (see FIG. 10A). If aerial hyphae are produced, they are predominantly oriented perpendicular to the biomat:air and/or biomat:media interface. For all biomats, the dense layer is comprised of long filaments which are predisposed to be aligned parallel with the biomat:air and/or biomat:media interface. Further, the resulting biomat is comprised of at least a majority of the fungal biomass and in preferred embodiments, comprised of essentially no residual feedstock and is essentially pure fungal biomass.

In those instances where aerial hyphae are formed, such as when glycerol is used as a substrate, a number of key distinguishing factors also exist between the aerial hyphae layer and the dense bottom layer. In terms of length, aerial hyphae tend to be longer than those found in the dense bottom layer. The density and distribution of the individual aerial hyphae is less than those associated with the dense layer mycelium. The aerial hyphae tend to a vertical orientation at the terminus juxtaposed to the atmosphere. That is, aerial hyphae tend to grow relatively perpendicular to the surface medium. On the other hand, the hyphae of the dense layer tend to grow in a predominantly parallel orientation to the air:biomat and/or biomat:media interface. The low relative density of the aerial hyphae combined with their longer length and vertical orientation suggests a maximization of oxygen harvesting. Further, little to no extra cellular matrix is found in the aerial hyphae layer. In contrast, a lot of extracellular matrix can be found in the dense bottom layer.

The aerial layer of the biomat, if formed, appears to accelerate the growth of the biomat. Disruptions to the aerial layer disrupted area negatively impact the accelerated growth of the biomat. Disruptions include contact with a solid object, contact with water droplets, and cracks or fissures caused from agitation of the liquid media upon which the biomat grows. Typically, the disrupted biomat area undergoes no further growth when the cause of the disruption is removed. Generally, the biomat growth is produced by aerobic conditions, microaerobic conditions, and anaerobic conditions or any combination thereof.

The biomats are normally harvested between day 3 and day 12 after inoculation, depending on the species/strain(s) used and the desired product, although later harvest times are also possible. The filamentous fungi biomats can be harvested by a number of different methodologies which can include; rinsing, physical processing (size reduction, pressure treatments, dehydration, etc.), inactivation of viability procedures, temperature cycling, extractions and/or separation of biomass constituents, and conversion and/or inclusion into different systems. In some embodiments the filamentous fungi biomats are harvested, rinsed with water, and are then either dried in a temperature controlled oven to deactivate many of the enzymes and limit biochemical transformations within the biomat, or, are frozen.

Filamentous fungi are recognized as very useful as host cells for recombinant protein production and expression platforms, resulting in useful products expressed in the biomass, and/or a filamentous fungi biomat. Examples of filamentous fungi which are currently used or proposed for use in such processes include *Neurospora crassa, Acremonium chrysogenum, Tolypocladium geodes, Mucor circinelloides, Trichoderma reesei, Aspergillus nidulans, Aspergillus niger* and *Aspergillus oryzae*. Further, microbial species used to produce biomats as disclosed can be genetically modified to express/depress systems by manipulation of gene expression, including transcription, such that they either overexpress or do not express compounds or chemistries found in their native or unaltered form. The use of and manipulation of fungal systems to over express existing chemistries, express systems not naturally present or depress systems commonly present in the native form is known as the art, i.e. *Aspergillus* spp., *Penicillium* spp., *Rhizopus* spp., *Trichoderma* spp., and yeasts such as *Pichia* spp. Useful products produced using the biomat and methods disclosed include, but are not limited to, biomass and/or biomass biomats used to express pharmaceuticals, nutraceuticals, building block chemicals for industrial application, medicinals, enzymes and/or precursors thereof.

Acidophilic Fungal Species and/or Strain(s)

The acidophilic fungal species and/or strains used in the present invention are lignocellulose degrading, filamentous fungal strains and/or their progeny that have at least the following identifying characteristics:
  a) the isolated strain is acidophilic and can grow at pH ranging from about 0.68 of about 8.5; and
  b) produce filamentous, biomats containing proteins and lipids from artificial media via surface fermentation under aerobic conditions, microaerobic conditions, anaerobic conditions or any combination thereof. Here, the artificial media's carbon source includes carbohydrates, lignocellulosic feedstocks, carbon containing waste products (e.g. acid whey), or a combination thereof.

The isolated species and/or strain(s) further typically comprise one or more of the following additional identifying characteristics:
  c) the ability to produce proteins, lipids amino acids, enzymes, nucleic acids (nucleotides), carbohydrates, fibers such as beta glucans, polyketides, alkaloids, pigments, and antibiotics. Examples of include, but are not limited to esters, glutamic acid, aspartic acid, amylases, proteases, cellulases, xylanases, lipases, peroxidases, manganese peroxidases, nucleic acids/nucleotides: DNA/RNA, purines, pyrimidines, oleic acid, palmitoleic acid, beta-glucan, chitin, beta-carotene, glycosides, phenolics, terpenoids from carbon sources as described herein and algal feedstocks, and from waste generated during biofuel production (e.g. processed algal biomass, glycerol) under a variety of anaerobic, aerobic microaerobic conditions and/or any combination thereof,
  d) comprise an 18S rRNA and ITS region DNA sequence that shares at least 98% identity to SEQ ID NO.:1.

Suitable filamentous acidophilic fungal species and/or strain(s) include *Fusisporium, Pseudofusarium, Gibberella, Sporotrichella, Aspergillus, Penicillium, Triocoderma*, species within the *Mucorales* sp. (e.g., *Rhizopus* sp.), the isolated filamentous acidophilic fungal strain designated as MK7, and combinations thereof, and/or their progeny. The strain designated as MK7, has been deposited as ATCC Accession Deposit No. PTA-10698.

The acidophilic fungal species and/or strain(s) and/or its progeny can grow at a low pH of at most about 7.0, about 6.5, about 6.0, about 5.5, about 5.0, about 4.5, about 4.0, about 3.5, about 2.0, about 1.8, about 1.6, about 1.4, about 1.2, about 1.0, about 0.9, about 0.8, or about 0.7 or about 0.6, or about 0.5. For example, the fungal strain can grow at a low pH ranging from about 0.68 to about 2.0.

The acidophilic species and/or strain(s) employed can produce lipids and proteins in high quantities within the filamentous fungi biomats grown under the low pH ranges as described above. For example, the isolated strain can convert the carbon source to lipids at a higher rate within a low pH as described above than has been previously reported in the art, such as the previously isolated *Fusarium* strains have been described (see Nairn et al., 1985, Bhatia et al., 2006, and Naqvi et al., 1997). The acidophilic species and/or strain(s) employed can convert a carbon source to lipids at a rate of at least 0.04 g lipid/g carbon source, 0.05 g lipid/g carbon source, 0.06 g lipid/g carbon source 0.07 g lipid/g carbon source, 0.08 g lipid/g carbon source, 0.1 g lipid/g carbon source, 0.12 g lipid/g carbon source, 0.14 g lipid/g carbon source, 0.16 g lipid/g carbon source, 0.18 g lipid/g carbon source, 0.2 g lipid/g carbon source, 0.25 g lipid/g carbon source, 0.3 g lipid/g carbon source, 0.35 g lipid/g carbon source, or 0.4 g lipid/g carbon source, after 10 days incubation at pH 2.5.

The culturing conditions of the current invention also produces filamentous biomass having a more favorable lipid profile when compared to the biomass previously produced from cultured fungi or microalgae. For example, the acidophilic species and/or strain(s) used produce more saturated fatty acids (e.g., palmitic (16:0) and stearic acids (18:0)) and mono-unsaturated fatty acids (e.g., oleic acid (18:1)), but less polyunsaturated fatty acids, which area more vulnerable to oxidation.

In addition, the acidophilic fungal species and/or strain(s) and/or its progeny can grow at a high metal concentration, where the metal is selected from the group consisting of Mn, Ag, Zn, Fe, Al, Be, Pb, Cu, Cr, Ni, Cd, Co, Ni, Pd, Pt, U, Th, Mo, Sn, Ti, As, Au, Se, Sb and Hg.

The acidophilic fungal species and/or strains and/or their progeny are capable of rapid, high density cell growth under the culturing conditions. Here, the microorganisms are capable of achieving a cell density (measured as dry weight/L of artificial media) of at least about 10 g/L, at least about 15 g/L, at least about 20 g/L, at least about 25 g/L, at least about 30 g/L, at least about 50 g/L, at least about 75 g/L, at least about 100 g/L, at least about 125 g/L, at least about 135 g/L, at least about 140 g/L, at least about 145 g/L, at least about 150 g/L, at least about 160 g/L, at least about 170 g/L, at least about 180 g/L, at least about 190 g/L, at least about 200 g/L, at least about 210 g/L, at least about 220 g/L, at least about 230 g/L, at least about 240 g/L, at least about 250 g/L.

For example, the acidophilic fungal species and/or strain(s) are capable of achieving a cell density of from about 10 g/L to about 300 g/L, from about 15 g/L to about 300 g/L, from about 20 g/L to about 300 g/L, from about 25 g/L to about 300 g/L, from about 30 g/L to about 300 g/L, from about 50 g/L to about 300 g/L, from about 75 g/L to about 300 g/L, from about 100 g/L to about 300 g/L, from about 125 g/L to about 300 g/L, from about 150 g/L to about 300 g/L, from about 170 g/L to about 300 g/L, from about 130 g/L to about 290 g/L, from about 135 g/L to about 280 g/L, from about 140 g/L to about 270 g/L, from about 145 g/L to about 260 g/L, from about 150 g/L to about 250 g/L, from about 170 g/L to about 250 g/L, from about 100 g/L to about 280 g/L. The high density growth of the acidophilic fungal species and/or strain(s) of can be further increased by adjusting the fermentation conditions (such as temperature, pH, concentration of ions, time of incubation and/or gas concentrations).

*Fusarium* Species

Information regarding acidophilic *Fusarium* species, methods of identifying, isolating culturing is described in Nelson et al., (Taxonomy, Biology, and Clinical Aspects of *Fusarium* Species, 1994, *Clinical Microbiology Reviews*, 7(4): 479-504), Toussoun and Nelson (1976, *Fusarium*), Booth (*Fusarium*: laboratory guide to the identification of the major species, 1977, Commonwealth Mycological Institute, ISBN 0851983839, 9780851983837) and Leslie et al., (The *Fusarium* laboratory manual, 2006, Wiley-Blackwell, ISBN 0813819199, 9780813819198), each of which is herein incorporated by reference in its entirety.

Proteins, including, e.g., certain enzymes, produced by the filamentous fungal species and/or strain(s) can be purified from the filamentous biomass produced by the organisms. Methods of protein purification are known to one skilled in the art. Detailed protein purification methods have been described in Janson and Ryden (Protein purification: principles, high-resolution methods, and applications; Wiley-VCH, 1998, ISBN 0471186260, 9780471186267), Detscher (*Guide to protein purification, Volume* 182 *of Methods in enzymology*, Gulf Professional Publishing, 1990, ISBN 0121820831, 9780121820831), and Cutler (*Protein purification protocols, Volume* 244 *of Methods in molecular biology*, Humana Press, 2004 ISBN 1588290670, 9781588290670), which are incorporated by reference in their entireties for all purposes.

Proteins need not be purified from the mats to find utility and usefulness as products. That is, the mat can be processed without purification and be useful; i.e. as a protein source, as a food stuff, and/or as animal feed. The mats can form products unto themselves; the mix of biomat produced products in situ are important and valuable.

Lipids of the Fungal Species and/or Strain(s)

As noted above, when cultured in artificial media having a high C:N ratio, filamentous fungi biomats are produced which have a high lipid content and a more favorable lipid profile as compared to algae and other lipid producing organisms. The lipids can be extracted from the isolated filamentous biomass. In some cases, the lipids are primarily triacylglycerides with fatty acid acyl groups. In some instances, the fatty acids are essentially unsaturated fatty acids and/or saturated fatty acids. The unsaturated fatty acids include oleic acid (18:1), α-linolenic acid (18:3), eicosenoic acid (20:1), and combinations thereof. Saturated fatty acids include palitic acids (16:0), stearic acids (18:0), arachidic acid (20:0), behenic acid (22:0), and combinations thereof. Other types of lipids that may be produced include, but are not limited to, sterols (e.g. ergosterol, a vitamin in D2 precursor), diacyclyglycerides, carotenoids, saturated fats (e.g., butyric acid, hexanoic acid, octanoic acid, decanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, docosanoic acid, tetracosanoic acid), monounsaturated fats (e.g., tetradecenoic acid, pentadecenoic acid, hexadecenoic acid, heptadecenoic acid, octadecenoic acid, eicosenoic acid, docosenoic acid, cis-tetracosenoic acid), and polyunsaturated fats (e.g., hexadecadienoic acid, linoleic acid, linolenic acid, alpha-linolenic acid, gamma-linolenic acid, parinaric acid, eicosadienoic acid, arachidonic acid, timnodonic acid, brassic acid, clupanodonic acid and docosahexaenoic acid).

The filamentous fungal species and/or strain(s) and/or their progeny are capable of efficient production of lipids. In some instances, the amount of lipids produced is at least about 1 g/L/day, 5 g/L/day, at least about 10 g/L/day, at least about 20 g/L/day, at least about 30 g/L/day, at least about 40 g/L/day, at least about 50 g/L/day, at least about 60 g/L/day, at least about 70 g/L/day, or more. For example, the amount of biological oil produced is from about 1 g/L/day to about 5 g/L/day, from about 5 g/L/day to about 70 g/L/day, from about 10 g/L/day to about 70 g/L/day, from about 20 g/L/day to about 70 g/L/day, or from about 30 g/L/day to about 70 g/L/day. These values are far greater than the highest reported value in the literature of about 12 g/L/day (see Dey, P. et al. (2011) Comparative lipid profiling of two endophytic fungal isolates—*Colletotrichum* sp. and *Alternaria* sp. having potential utilities as biodiesel feedstock. *Bioresource Technology* 102:5815-5823; Gong, Z. et al. (2013) Efficient conversion of biomass into lipids by using the simultaneous saccharification and enhanced lipid production process. *Biotechnology for Biofuels* 6:36; Gong, Z. et al. (2014) Lipid production from corn stover by the oleaginous yeast *Cryptococcus curvatus*. *Biotechnology for Biofuels* 7:158; Hui, L. et al. (2010) Direct microbial conversion of wheat straw into lipid by a cellulolytic fungus of *Aspergillus oryzae* A-4 in solid-state fermentation. *Bioresource Technology* 101:7556-7562; Liang, Y. et al. (2014) Microbial lipid production from pretreated and hydrolyzed corn fiber. *Biotechnol Progress* 30:945-951; Liu, C.-Z. et al. (2012) Ionic liquids for biofuel production: Opportunities and challenges. *Applied Energy* 92:406-414; Ruan, Z. et al. (2013) Co-hydrolysis of lignocellulosic biomass for microbial lipid accumulation. *Biotechnol. Bioeng.* 110:1039-1049; Sung, M. et al. (2014) Biodiesel production from yeast *Cryptococcus* sp. using Jerusalem artichoke. *Bioresource Technology* 155:77-83; Xie, H. et al. (2012) Enzymatic hydrolysates of corn stover pretreated by a N-methylpyrrolidone-ionic liquid solution for microbial lipid production. *Green Chem.* 14:1202-1210).

Lipids can be extracted from the filamentous fungi biomats using various procedures. Non-limiting examples of lipid extraction are described in King et al. (Supercritical Fluid Extraction: Present Status and Prospects, 2002, *Grasa Asceites*, 53,8-21), Folch et al. (A simple method for the isolation and purification of total lipids from animal tissues, 1957, *J Biol. Chem.*, 226, 497-509), Bligh and Dyer (A rapid method of total lipid extraction and purification. 1959, *Can. J Biochem. Physiol.*, 37, 911-917), Cabrini et al. (Extraction of lipids and lipophilic antioxidants from fish tissues—a comparison among different methods. 1992, *Comp. Biochem. Physiol.*, 101(3), 383-386), Hara et al. (Lipid extraction of tissues with a low toxicity solvent. 1978, *Anal. Biochem.* 90, 420-426), Lin et al. (Ethyl acetate/ethyl alcohol mixtures as an alternative to Folch reagent for extracting animal lipids. 2004, J. Agric. Food Chem., 52, 4984-4986), Whiteley et al. (Lipid peroxidation in liver tissue specimens stored at subzero temperatures. 1992, Cryo-Letters, 13, 83-86), Kramer et al. (A comparison of procedures to determine free fatty acids in rat heart. 1978, J. Lipid Res., 19, 103-106) and Somashekar et al. (Efficacy of extraction methods for lipid and fatty acid composition from fungal cultures, 2001, *World Journal of Microbiology and Biotechnology*, 17(3):317-320).

In another example, lipid can be extracted by methods similar to the FRIOLEX® (Westfalia Separator Industry GmbH, Germany) process is used to extract the biological oils produced by the microorganisms. FRIOLEX® is a water-based physical oil extraction process, whereby raw material containing oil can be used directly for extracting oil without using any conventional solvent extraction methods. In this process, a water-soluble organic solvent can be used as a process aid and the oil is separated from the raw material broth by density separation using gravity or centrifugal forces.

After the lipids have been extracted, the lipids can be recovered or separated from non-lipid components by any suitable means known in the art. For example, low-cost physical and/or mechanical techniques are used to separate the lipid-containing compositions from non-lipid compositions. If multiple phases or fractions are created by the extraction method used to extract the lipids, where one or more phases or fractions contain lipids, a method for recovering the lipid-containing phases or fractions can involve physically removing the lipid-containing phases or fractions from the non-lipid phases or fractions, or vice versa. In some cases, a FRIOLEX® type method is used to extract the lipids produced by the microorganisms and the lipid-rich light phase is then physically separated from the protein-rich heavy phase (such as by skimming off the lipid-rich phase that is on top of the protein-rich heavy phase after density separation).

There are at least two stages in the production of lipids by the filamentous fungal species and/or strain(s): (a) the filamentous fungi biomat accumulation stage and (b) the lipid production stage. The filamentous fungi biomat accumulation stage produces a filamentous biomass, of the fungal species and/or strain(s) such that about 10% to about 95%, about 20% to about 95%, about 30% to about 95%, about 40% to about 95%, or about 50% to about 95% of the total filamentous fungi biomat production of the fungal strain is achieved during the filamentous fungi biomat accumulation stage. In other cases, about 60% to about 95%, about 70% to about 95%, or about 80% to about 95% of the total filamentous fungi biomat production of the microorganism is achieved during the filamentous fungi biomat accumulation stage. In other circumstances, the filamentous fungi biomat accumulation stage produces filamentous biomass of the microorganism such that at least about 10%, at least about 20%, at least about 30%, at least about 40%, at least about 50%, at least about 60%, at least about 70%, at least about 80%, at least about 90%, at least about 95%, or 100% of the total filamentous biomass production of the microorganism is achieved during the filamentous fungi biomat accumulation stage. For example, about 50% to about 95% of the total filamentous fungi biomat production of the microorganism is achieved during the filamentous fungi biomat accumulation stage.

With respect to the lipid production stage, lipids are produced throughout all growth stages as they are required for cell growth and proliferation; that is, lipids are produced during the filamentous fungi biomat accumulation stage. While not being bound by theory, it is believed that some storage lipids are produced in later stages of biomat growth while other storage lipids are produced earlier on during biomat formation. In addition, under low nitrogen conditions the organism will accumulate storage lipids at a faster rate.

The lipid accumulation stage produces lipids such that about 10% to about 95%, about 20% to about 95%, about 30% to about 95%, about 40% to about 95%, or about 50% to about 95% of the total lipid production of the microorganism is achieved during the lipid accumulation stage. In some cases, about 60% to about 95%, about 70% to about 95%, or about 80% to about 95% of the total lipid production of the microorganism is achieved during the lipid accumulation stage. In other circumstances, the lipid accumulation stage produces lipids such that at least about 10%, at least about 20%, at least about 30%, at least about 40%, at least about 50%, at least about 60%, at least about 70%, at least about 80%, at least about 90%, or at least about 95% of the total lipid production of the microorganism is achieved during the lipid accumulation stage. Preferably, about 50% to about 95% of the total lipid production of the microorganism is achieved during the lipid accumulation stage.

Once the lipids are produced in accordance with the present invention, various methods known in the art can be used to transform the biological oils into esters of fatty acids for use as ingredients for food or pharmaceutical products. The production of esters of fatty acids can comprise transesterifying the biological oils produced by the microorganism. The extraction of the lipids from the microorganisms and the transesterification of the lipids can be performed simultaneously, in a one-step method. For example, the culture containing the isolated fungal strain can be exposed to conditions or treatments (or a combination of conditions or treatments) that promote both extraction of the lipids and the transesterification of the lipids. Such conditions or treatments include, but are not limited to, pH, temperature, pressure, the presence of solvents, the presence of water, the presence of catalysts or enzymes, the presence of detergents, and physical/mechanical forces. Two sets of conditions or treatments can be combined to produce a one-step method of extracting and transesterifying the lipids, where one set of conditions or treatments favorably promotes extraction of the lipids and the other set of conditions or treatments favorably promotes transesterification of the lipids, so long as the two sets of conditions or treatments can be combined without causing significant reduction in the efficiency of either the extraction or the transesterification of the lipids. Hydrolysis and transesterification can be performed directly on whole-cell filamentous biomass.

Alternatively, the extraction of the lipids is performed as a step that is separate from the step of transesterification of the lipids. Such transesterification reactions are performed using acid or base catalysts. Methods for transesterifying the biological lipids into esters of fatty acids for use as ingredients for food or pharmaceutical products involves reacting the biological oils containing triglycerides in the presence of an alcohol and a base to produce esters of the fatty acid residues from the triglycerides.

Alcohols suitable for use in transesterification include any lower alkyl alcohol containing from 1 to 6 carbon atoms (i.e., a $C_{1-6}$ alkyl alcohol, such as methyl, ethyl, isopropyl, butyl, pentyl, hexyl alcohols and isomers thereof). Without being bound by theory, it is believed that the use of lower alkyl alcohols produces lower alkyl esters of the fatty acid residues. For example, the use of ethanol produces ethyl esters. If the alcohol is methanol or ethanol, the fatty acid esters produced are a methyl ester and an ethyl ester of the fatty acid residue, respectively. Typically, the alcohol comprises from about 5 wt. % to about 70 wt. %, from about 5 wt. % to about 60 wt. %, from about 5% to about 50 wt. %, from about 7 wt. % to about 40 wt. %, from about 9 wt. % to about 30 wt. %, or from about 10 wt. % to about 25 wt. % of the mixture of the lipids composition, the alcohol and the base. The composition and the base can be added to either pure ethanol or pure methanol. In general, the amount of alcohol used may vary with the solubility of the lipids or composition containing triglycerides in the alcohol.

The composition comprising triglycerides, the alcohol and the base are reacted together at a temperature and for an amount of time that allows the production of an ester from the fatty acid residues and the alcohol. Suitable reaction times and temperatures to produce an ester may be determined by one of skill in the art. Without intending to be bound by theory, the fatty acid residues are believed to be cleaved from the glycerol backbone of the triglyceride and esters of each fatty acid residue are formed during the step of reacting. The step of reacting the composition in the presence of an alcohol and a base is performed at a temperature from about 20° C. to about 140° C., from about 20° C. to about 120° C., from about 20° C. to about 110° C., from about 20° C. to about 100° C., or from about 20° C. to about 90° C. Alternatively, the step of reacting the composition in the presence of an alcohol and a base is performed at a temperature at or greater than about 20° C., 75° C., 80° C., 85° C., 90° C., 95° C., 105° C., or 120° C. Depending on the desired product, the step of reacting the composition in the presence of an alcohol and a base is performed for a time from about 2 hours to about 36 hours, from about 3 hours to about 36 hours, from about 4 hours to about 36 hours, from about 5 hours to about 36 hours, or from about 6 hours to about 36 hours. Instead, the step of reacting the composition in the presence of an alcohol and a base can be performed for about 0.25, 0.5, 1.0, 2.0, 4.0, 5.0, 5.5, 6, 6.5, 7, 7.5, 8, 8.5, 10, 12, 16, 20, 24, 28, 32, or 36 hours.

The step of reacting the lipids composition, alcohol and base may be conducted by refluxing the components to produce the fatty acid esters, such as PUFA esters. The step of reacting the lipids composition may also be carried out at a temperature that does not result in the refluxing of the reaction components. For example, carrying out the step of reacting the lipids composition under pressures greater than atmospheric pressure can increase the boiling point of the solvents present in the reaction mixture. Under such conditions, the reaction can occur at a temperature at which the solvents would boil at atmospheric pressure, but would not result in the refluxing of the reaction components. Generally, the reaction is conducted at a pressure from about 5 to about 20 pounds per square inch (psi); from about 7 to about 15 psi; or from about 9 to about 12 psi. Some reactions are conducted at a pressure of 7, 8, 9, 10, 11, or 12 psi. Reactions conducted under pressure may be carried out at the reaction temperatures listed above. Reactions conducted under pressure may be carried out at a temperature at or greater than about 70° C., 75° C., 80° C., 85° C., or 90° C.

Fatty acid esters are separated from the reaction mixture by distilling the composition to recover a fraction comprising the ester of the fatty acid. A targeted fraction of the reaction mixture including the fatty acid esters of interest can be separated from the reaction mixture and recovered. The distillation can be performed under vacuum. Without being bound by theory, distillation under vacuum allows the distillation to be accomplished at a lower temperature than in the absence of a vacuum and thus may prevent the degradation of the esters. Typical distillation temperatures range from about 120° C. to about 170° C., such as performing the distillation at a temperature of less than about 180° C., less than about 175° C., less than about 70° C., less than about 165° C., less than about 160° C., less than about 155° C., less than about 150° C., less than about 145° C., less than about 140° C., less than about 135° C., or less than about 130° C. Typical pressures for vacuum distillation range from about 0.1 mm Hg to about 10 mm Hg, such as a vacuum distillation pressure of at or greater than about 0.1, 0.5, 1, 1.5, 2, 2.5, 3, 3.5, or 4 mm Hg.

The lipids extracted from the filamentous fungal species or strain and/or its progeny of the present invention are used to produce biolubricants. As used herein, the term "biolubricants" refers to lubricants produced by using material originated from living or recently living organisms. As used herein, the term "lubricants" refers to substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 09. One of the single largest applications for lubricants, in the form of motor oil, is to protect the internal combustion engines in motor vehicles and powered equipment. Typically, lubricants contain 90% base oil (most often petroleum fractions, called mineral oils) and less than 10% additives. Vegetable oils or synthetic liquids such as hydrogenated polyolefins, esters, silicones, fluorocarbons and many others are sometimes used as base oils. These are primarily triglyceride esters derived from plants and animals. For lubricant base oil use the vegetable derived materials are preferred. Common ones include high oleic canola oil, castor oil, palm oil, sunflower seed oil and rapeseed oil from vegetable, and Tall oil from animal sources. Many vegetable oils are often hydrolyzed to yield the acids which are subsequently combined selectively to form specialist synthetic esters.

Thus, the lipids extracted from the filamentous fungi biomats formed by the filamentous fungal species and/or strain(s) and/or their progeny of the present invention can be used to produce ester-based biolubricant compositions by adding suitable additives. Methods of making ester-based lubricant compositions are known to one skilled in the art. For a non-limiting example, a quantity of biologically-derived oil comprising triglycerides is provided and processed so as to hydrolyze at least some of the triglycerides and form free fatty acids, wherein the fatty acids are of a type selected from the group consisting of saturated fatty acids, monounsaturated fatty acids, and polyunsaturated fatty acids, and combinations thereof. The fatty acids are separated by type, such that at least the monounsaturated fatty acids are substantially isolated from the saturated fatty acids and the polyunsaturated fatty acids. Next, at least some of the monounsaturated fatty acids are modified to form an ester product (e.g., comprising triesters), and at least some of the saturated fatty acids and/or polyunsaturated fatty acids are hydrotreated to yield alkanes (paraffins). Note also that in some embodiments, such ester products can include one or more of the following: mono-, di-, and triester species, and hydroxylated analogues thereof.

Acid pH Tolerant Enzymes from Filamentous Fungal Species and/or Strain(s)

The genome of *Fusarium oxysporum* f sp. *lycopersici* strain 4287 has recently been sequenced and has been shown to carry a variety of genes involved in the degradation of lignin, hemicellulose and cellulose. Furthermore, the enzymes involved in the degradation of these materials (e.g., cellulase, xylanase, ligninase, glucuronidase, arabinofuranosidase, arabinogalactanase, ferulic acid esterase, lipase, pectinase, glucomannase, amylase, laminarinase, xyloglucanase, galactanase, glucoamylase, pectate lyase, chitinase, exo-[3-D-glucosaminidase, cellobiose dehydrogenase, and acetylxylan esterase, xylosidase, a-L-arabinofuranosidase, feruloyl esterase, endoglucanase, [3-glucosidase, Mn-peroxidase, and laccase) have been studied extensively in *F. oxysporum* strain F3 (Xiros et al. (2009) Enhanced ethanol production from brewer's spent grain by a *Fusarium oxysporum* consolidated system. Biotechnol Biofuels 10:4). Consequently, acidophilic filamentous fungal species and/or strain(s) such as *Fusarium* species and the acidophilic filamentous fungal strain designated as MK7, are expected to be fully equipped to hydrolyze complex carbon sources, such as lignocellulosic materials and waste streams (e.g. acid whey). It is also expected that since these acidophilic filamentous fungal species and/or strain(s) are capable of growth at much lower pH (0.7-7.5) in comparison to other filamentous strains (pH>2; Starkey, 1973), the enzymes for lignin, hemicellulose and cellulose degradation will have higher activities at low pH. Enzymes with high activity under acidic conditions would be especially useful in processes conducted at low pH.

Toxins Produced by *Fusarium* Species.

Oftentimes, microbial based production requires the use of costly and time consuming methods to prevent contamination. As discussed above, filamentous acidophilic fungal species and/or strain(s) are highly resistant to contamination by other organisms. It is known, for example, that members of the *Fusarium* genus generate toxins (e.g., fumonisins), which have potent antibiotic, insecticidal and phytotoxic properties. Similarly, the filamentous acidophilic MK7 fungal strain requires little or no external antibiotics to be added when used in the production of filamentous fungi biomats. Some *Fusarium* species can produce nine different toxins, with production depending on their relationship with different host plants (Marasas et al., 1984, Toxigenic *Fusarium* species, identity and mycotoxicology, ISBN 0271003480). The production of toxins also varies with media used for fermentation. The toxins produced and secreted by *Fusarium* species include, but are not limited to, bikaverin, enniatins, fusaric acid, lycomarasmin, moniliformin, oxysporone, trichothecenes, zearelones, various naphthoquinones and anthraquinones (e.g., nonaketide naphthazarin quinones, bikaverin and norbikaverin, heptaketides, nectriafurone, 5-0-methyljavanicin, and anhydrofusarubin lactol).

Additionally, the toxins from *Fusarium* species may include, 4-Acetoxyscirpenediol (4-3-acetoxy-3,15-dihydroxy-12,13-epoxytrichothec-9-ene. A similar compound, monodeacetylanguidin 4- or 15-acetylscirpentriol), 3-Acetyldeoxynivalenol (Deoxynivalenol monoacetate, 3"-acetoxy-7",15-dihydroxy-12,13-epoxytrichothec-9-en-8-one), 8-Acetylneosolaniol (Neosolaniol monoacetate, 4",8", 15-triacetoxy-3"-hydroxy-12,13-epoxytrichothec-9-ene), 4- or 15-Acetylscirpentriol (4-Acetoxyscirpenediol), Acetyl T-2 toxin (3",4",15-triacetoxy-8"-(3-methylbutyry(oxy)-12, 13-epoxytricho-thec-9-ene), Anguidin (Diacetoxyscirpenol), Avenacein, Beauvericin, Butenolide (4-acetamido-4-hydroxy-2-butenoic-acid-lactone), Calonectrin (3",15-diacetoxy-12,13-epoxytrichothec-9-ene), 15-Deacetylcalonectrin (15-De-O-acetylcalonectrin, 3"-acetoxy-15-hydroxy-12,13-epoxytrichothec-9-ene), Deoxynivalenol (Rd toxin, Vomitoxin, 3", T', 15-trihydroxy-12,13-epoxytricho-thec-9-en-8-one), Deoxynivalenol diacetate (Diacetyldeoxynivalenol), Deoxynivalenol monoacetate (3-Acetyldeoxynjvalenol), Diacetoxyscirpendiol (7"-Hydroxydiacetoxyscirpenol), Diacetoxyscirpenol (Anguidin, 4,15-diacetoxy-3'-hydroxy 12,13-epoxytrjchothec-9-ene), Diacetoxyscerpentriol (7",8"-Dihydroxydiacetoxyscirpenol), Diacetyldeoxynivalenol (Deoxynivalenol diacetate, 3",15-diacetoxy-7-hydroxy 12,13-epoxytrichothec-9-en-8-one), Diacetylnivalenol (Nivalenol diacetate, 4,15-diacetoxy-3',7'-dihydroxy-12,13-epoxytrichothec-9-en-8-one), 7",8"-Dihydroxydiacetoxyscirpenol (Diacetoxyscirpentriol, 4,15-diacetoxy-3",7",8"-trihydroxy-12,13-epoxytrichothec-9-ene), Enniatins, Fructigenin, Fumonisin B1 (1,2,3-propanetricarboxylic acid 1,-1-[1-(12-amino-4,9,11-trihydroxy-2-methyltridecyl)-2-(1-methylpentyl)-1,2-ethanediyl] ester; macrofusine), Fusarenon (Fusarenon-X, Fusarenon, Monoacetylnivalenol, Nivalenol monoacetate, 4-acetoxy-3",7", 15-trihydroxy-12,13-epoxytrichothec-9-en-8-one) Fusaric acid (Fusarinic acid, 5-butylpicolinic acid), Fusarinic acid (Fusaric acid), F-2 (Zearalenone), HT-2 toxin=15-acetoxy-3",4-dihydroxy-8"-(3-methylbutyryloxy)-12-epoxytrichothec-9-ene, 7"-Hydroxy-diacetoxyscirpenol (Diacetoxyscirpendiol, 4,15-diacetoxy-3",7"-dihydroxy-12,13-epoxytrichothec-9ene), 8"-Hydroxydiacetoxyscirpenol (Neosolaniol), 1,4-Ipomeadiol(1-(3-furyl)-1,4-pentanediol), lpomeanine(1-(3-furyl)-1,4-pentanetione), 1-Ipomeanol(1-(3-furyl)-1-hydroxy-4-pentanone), 4-lpomeanol(1-(3-furyl)-4-hydroxy 4pentanone), Lateritin, Lycomarasmin, Moniliformin (potassium or sodium salt of 1-hydroxycyclobut-1-ene-3,4-dione), Monoacetoxyscirpenol (15-acetoxy-3",4"-dihydroxy-12,13-epoxytrichothec-9ene),
Monoacetylnivalenol (Fusarenon-X), Monodeacetylanguidin (4-Acetoxyscirpenediol), Neosolaniol (8"-Hydroxydiacetoxyscirpenol, 4,15-diacetoxy-3"8"-dihydroxy-12,13-epoxytrichothec-9-ene), Neosolaniolacetate (8-Acetylneosolaniol), Neosolaniol monoacetate (8-Acetylneosolaniol), Nivalenol (3",4",7",15"-tetrahydroxy-12,13-epoxy-trichothec-9-en-8-one), Nivalenol diacetate (Diacetylnivalenol), Nivalenol monoacetate (Fusarenon-X), NT-1 toxin (T-1 toxin, 4",8"-diacetoxy-3",15-dihydroxy-12, 13-epoxy-trichothec-9-ene), NT-2 toxin (4"-acetoxy-3",8", 15-trihydroxy-12,13-epoxytrichothec-9-ene), Rd toxin (Deoxynivalenol), Sambucynin, Scirpentriol (3",4",15"-trihydroxy-12,13-epoxytrichothec-9-ene), Solaniol (Neosolaniol), T-1 toxin (NT-1 toxin), T-2 toxin (4",15"-diacetoxy-3"-hydroxy-8"-(3-methylbutyrlyloxy)-12,13-epoxytrichothec-9-ene), Triacetoxy-scirpendiol (4",8",15"-triacetoxy-3",7"-dihydroxy-12,13-epoxytrichothec-9-ene), Triacetoxy-scirpenol (3",4",15"-triacetoxy-12,13-epoxytrichothec-9-ene), Vomitoxin (Deoxynivalenol), Yavanicin, Zearalenol (2,4-dihydroxy-6-(6,10-dihydroxy-trans-1-undecenyl)-benzoic acid-lactone), Zearalenone (6-(10-hydroxy-6-oxo-trans-1-undecenyl)-resorcylic acid lactone). More detailed toxins produced by *F. oxysporum* are described in Tatum et al. (Naphthoquinones produced by *Fusarium oxysporum* isolated from citrus. 1985, *Phytochemistry* 24:457-459), Tatum et al. (Naphthofurans produced by *Fusarium oxysporum* isolated from citrus. 1987, *Phytochemistry,* 26:2499-2500), Baker et al. (Novel anthraquinones from stationary cultures of *Fusarium oxysporum*. 1998, *J Ferment Bioeng* 85:359-361). Thrane (*Fusarium* species on their specific profiles of secondary metabolites, in *Fusarium*. Mycotoxins, taxonomy and pathogenicity, 1989, ed by Chelkowski J, Elsevier, N.Y., USA, pp 199-225); Baker et al., Antimicrobial activity of naphthoquinones from Fusaria, Mycopathologia 111: 9-15, 1990; Marasas et al. (Toxigenic *Fusarium* species, identity and mycotoxicology, 1984, Pennsylvania State University Press, University Park, Pa., USA), each of which is incorporated by referent in its entirety for all purposes.

The present invention is further illustrated by the following examples that should not be construed as limiting. The contents of all references, patents, and published patent applications cited throughout this application, as well as the Figures and Sequence Listing, are incorporated herein by reference in their entirety for all purposes.

EXAMPLES

Example 1: Strain MK7 in the Natural Environment

Naturally occurring strain MK7 is always associated with algae, archaea and bacteria in nature and is characterized by average densities of less than 0.5 g dry biomass/L spring water (FIG. 1). In addition, MK7 occurs in nature as "streamers." Purcell et al. define "streamers" as follows: "Streamers are submerged aggregations of filamentous and other cell morphologies projecting into flowing water from a point of attachment" (Purcell et al. (2007) FEMS Microbiology Ecology 7 60:456-466). Strain MK7 as a percentage of total streamer biomass is less than 10%. Furthermore, strain MK7 biomass in nature is characterized by greater than 30% biomass as macro conidia cells, which are never found in surface fermentation biomats produced by the methods outline in this disclosure.

Example 2: Preparation of Artificial Media

MK7-1 liquid medium used in the following procedures was prepared by adding the ingredients listed in Table 1A to deionized water (18.2 Mohm), temperature between 22-30° C. followed by adjusting the pH to 2.8, pH adjusted lower with 13 N HCl. pH was measured using an Oakton Instruments model 150 pH meter and probe (Orangeburg, N.Y.). The medium was then boiled for 20 minutes and allowed to cool to room temperature (~23° C.) prior to use. Immediately before adding the liquid medium, the pH is checked again using the Oakton Instruments 150 pH meter and probe and adjusted back to pH 2.8 if required.

MK7-3 liquid medium was prepared in the same way using the ingredients listed in Table 1B.

In some embodiments the carbon source used is not glycerol, but can be selected from various other carbon sources, such as sugars, glycerol, lignocellulosic materials, hydrolysates of lignocellulosic materials, municipal or agricultural waste, food processing waste (e.g. acid whey), industrial waste stream products, potato waste (potato peels, potato discards due to degradation, potato cuttings, bruised potato), starch wastes, sugar beet waste, sugar beet pulp, waste from corn processing (i.e. corn steep liquor), wastes from production of biofuels (residues from cellulosic ethanol production, anaerobic digestate, etc.). In those cases, the media is adjusted to accommodate the contribution of nutrients from the carbon source used. For example, if the carbon source is molasses, acid whey, or lignocellulose, the trace elements needed will likely be partially or entirely provided by the carbon source and only the macronutrients may need to be added to the media. In other embodiments the carbon source may be classified as "food grade." In these instances, there is no expectation of trace elements and macronutrients associated with the carbon source and so all trace elements and macronutrients must be added.

TABLE 1A

Ingredients in MK7-1 medium used for inoculum generation.
MK7-1 Medium

| | Liquid (g/L) | Plate (g/L) | Grade | Lot # | Vendor | Location |
|---|---|---|---|---|---|---|
| NH4NO3 | 12.9 | 3 | ACS | 144801A | Fisher | Waltham, MA |
| Urea | 4.3 | 0.3 | ACS | A0355726 | ACROS | Somerville, NJ |
| KH2PO4 | 10 | 2 | Reagent | | Eiser-Golden | |
| CaCl2•2 H20 | 2.6 | 0.4 | ACS | 53H0276 | Sigma | St. Louis, MO |
| MgSO4•7H2O | 2 | 0.3 | Lab | 5GJ15040920A | Fisher | Waltham, MA |
| Yeast Extract | 2 | 0 | | | | |
| Agar | 0 | 15 | Technical | 5287994 | Fisher | Waltham, MA |
| Glycerol | 75 | 60 | Food | 4O19410427A | Duda Energy | Decatur, AL |
| Micronutrients* | mg/L | mg/L | | | | |
| FeSO4•7 H2O | 9.98 | 4.99 | ACS | 3562C398 | Amresco | Solon, OH |
| ZnSO4•7 H2O | 4.4 | 2.2 | USP/FCC | 61641 | Fisher | Waltham, MA |
| MnCl2•4 H2O | 1.01 | 0.51 | | 13446-34-9 | Fisher | Waltham, MA |
| CoCl2•6 H2O | 0.32 | 0.16 | | 7791-13-1 | Fisher | Waltham, MA |
| CuSO4•5 H2O | 0.31 | 0.16 | Technical | 114675 | Fisher | Waltham, MA |
| (NH4)6Mo7O24•4 H2O | 0.22 | 0.11 | ACS | 68H0004 | Sigma | St. Louis, MO |
| H3BO3 | 0.23 | 0.11 | ACS | 103289 | Fisher | Waltham, MA |
| EDTA, free acid | 78.52 | 39.3 | Electrophoresis | 46187 | Fisher | Waltham, MA |
| | pH | pH | | | | |
| HCl | 2.8 | 4.8 | ACS | 5GK251022 | Fisher | Waltham, MA |

TABLE 1B

Ingredients in MK7-3 medium.
MK7-3 Medium

| | Liquid (g/L) | Grade | Lot # | Vendor | Location |
|---|---|---|---|---|---|
| Urea | 8.4 | ACS | A0355726 | ACROS | Somerville, NJ |
| KH2PO4 | 10 | Reagent | | Eiser-Golden | |
| CaCl2•2 H20 | 2.6 | ACS | 53H0276 | Sigma | St. Louis, MO |
| MgSO4•7H2O | 2 | Lab | 5GJ15040920A | Fisher | Waltham, MA |
| Yeast Extract | 2 | | | | |
| Agar | 0 | Technical | 5287994 | Fisher | Waltham, MA |
| Glycerol | 75 | Food | 4O19410427A | Duda Energy | Decatur, AL |
| Micronutrients* | mg/L | | | | |
| FeSO4•7 H2O | 9.98 | ACS | 3562C398 | Amresco | Solon, OH |
| ZnSO4•7 H2O | 4.4 | USP/FCC | 61641 | Fisher | Waltham, MA |
| MnCl2•4 H2O | 1.01 | | 13446-34-9 | Fisher | Waltham, MA |
| CoCl2•6 H2O | 0.32 | | 7791-13-1 | Fisher | Waltham, MA |
| CuSO4•5 H2O | 0.31 | Technical | 114675 | Fisher | Waltham, MA |
| (NH4)6Mo7O24•4 H2O | 0.22 | ACS | 68H0004 | Sigma | St. Louis, MO |
| H3BO3 | 0.23 | ACS | 103289 | Fisher | Waltham, MA |
| EDTA, free acid | 78.52 | Electrophoresis | 46187 | Fisher | Waltham, MA |
| | pH | | | | |
| HCl | 2.8 | ACS | 5GK251022 | Fisher | Waltham, MA |

Example 3: Inoculation Process

Figure 2:
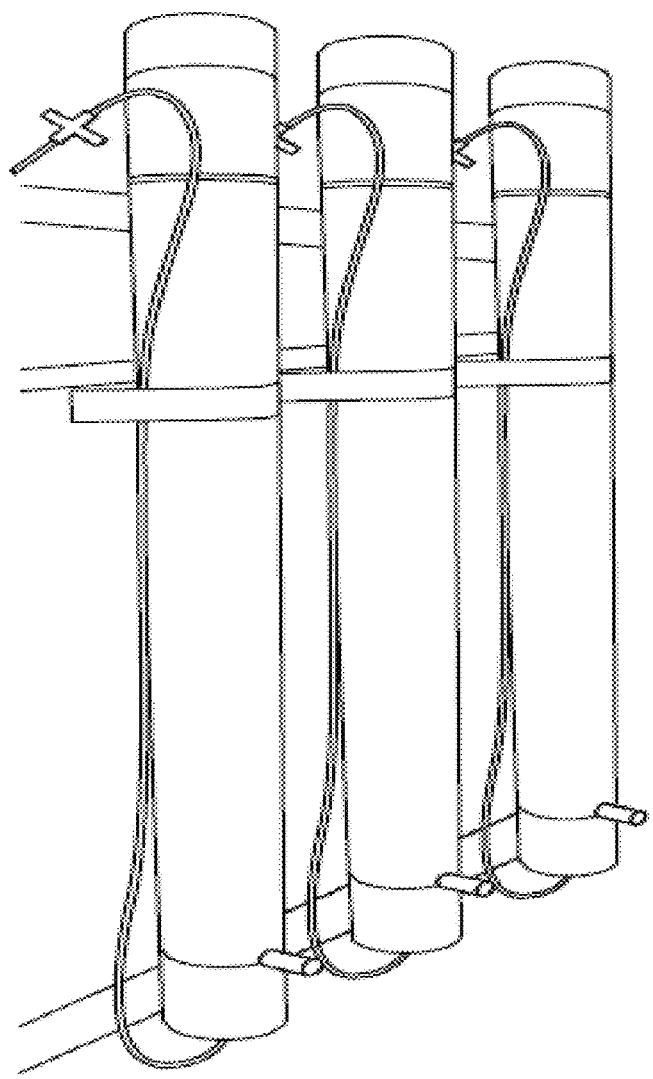
FIG. 2. Exemplary 10 L bioreactors used for the generation of inoculum.

Cultures to be used for inoculation of trays were grown in 10 L bioreactors under submerged fermentation conditions in MK7-1 liquid medium. It should be noted that other bioreactor sizes are amenable and that the choice of the 10 L reactor size is not to be construed as limiting. The 10 L reactor was constructed of a 1.3 m long section of 10.16 cm diameter clear PVC tubing with a PVC endcap at the bottom. A plastic aeration port/fitting with a 3 mm orifice was attached to the bottom endcap and tubbing to supply air was attached to the aeration port. A plastic sampling port/valve was attached to the side of the clear PVC wall 15 cm from the bottom of the bottom endcap. The top of the clear PVC reactor was covered by sterile gauze, which was held in place by a loosely fitting PVC endcap with a 3 mm hole to allow gasses to escape from the reactor. The assembled bioreactor is shown in FIG. 2.

Inoculum for the 10 L bioreactor was prepared from an archived culture stock of the filamentous acidophilic MK7 fungal strain (Lot #003). The archived stock culture consisted of the filamentous acidophilic MK 7 fungal strain mycelial mat grown on a sterile Petri dish containing solid medium comprised of 1.5% agar (BD Difco granulated agar, Lot #5287994, ThermoFisher, Waltham, Mass.), glycerol and inorganic nutrients as described in Table 1 for MK7-1 plate medium. The agar medium was prepared by boiling for 20 minutes, allowing the medium to cool to 50° C., and then pouring 25 mL of the solution into a sterile Petri plate. After cooling and solidification, the plate was inoculated with a second generation archived freezer stock, by using a sterile loop (heated to red hot in a flame and cooled) to collect a sample from the archived stock and streaking it on the Petri plate (FIG. 3A).

After 5 days of growth, the mycelial mat completely grew over the surface of the agar medium (FIG. 3B). The culture was then frozen at −80° C. Five days prior to inoculating the 10 L reactor, a Petri plate stock was removed from the freezer and allowing to equilibrate to room temperature (~23° C.) for 2 hours. The mycelial mat grown on the surface of the agar was then removed with sterile forceps (forceps were heated with a flame to red hot and cooled with isopropanol) and placed into 350 mL of sterile MK7-1 liquid medium in a sterile 1 L glass baffled shaker flask covered with a sterile gauze cloth. The flask was rotated at 200 rpm on a VWR OS-500 laboratory shaker (VWR, Radnor, Pa.) for 5 days prior to its use as inoculum for the 10 L bioreactor.

In preparation for receiving the inoculum, the 10 L bioreactor was sterilized by adding 330 mL of concentrated Na-hypochlorite solution (Chlorox® bleach=8.25% Na-hypochlorite) to 11 L of drinking quality tap water in the bioreactor and letting it equilibrate for two days. After two days, another 330 mL of concentrated Na-hypochlorite solution was added to the reactor. After one day, the diluted Na-hypochlorite solution was completely drained from the reactor and the reactor was rinsed with ~80° C. boiled water by adding 2 L of the hot water and swirling to rinse all of the surfaces inside the bioreactor. The rinse water was then drained. 3.5 L of sterile MK7-1 liquid medium was added to the bioreactor and bubbled with sterile air (0.2 um filtered) at a rate of 400 mL per minute through the aeration port located at the bottom of the reactor. These bubbling conditions generated bubbles ranging in size from 3 to 30 mm in diameter and resulted in mixing and homogenous distribution of fungal cells throughout the liquid medium (planktonic cells) during growth. Experiments have shown that higher bubbling rates or smaller bubble sizes result in biofilm growth habit that forms clumps of biomass that stick to surfaces in the bioreactor. Biofilm growth habit therefore is not desirable since a homogeneous suspension of cells is desirable for inoculation of the tray reactors. The inoculum grown in the 1 L shaker flask was then added to the 10 L reactor using aseptic technique (spraying all nearby outside surfaces with 70% isopropanol/30% water prior to opening the top of the bioreactor and not touching any of internal surfaces of the bioreactor). To build additional culture volume in the 10 L reactor, sterile fresh MK7-1 liquid medium was added to the reactor after the culture attained 6 g/L dry filamentous biomass density. If fresh MK7-1 liquid medium is to be added to the reactor, the volume should be no more than 9 times the liquid culture volume in the reactor. Dry filamentous biomass was measured by collecting a sample via aside port on the bioreactor while the aeration system is operating, and filtering a known volume through a 0.22 um filter (Millipore, Cat #GSWP04700, Darmstat, Germany) using a vacuum filtration apparatus (Millipore, Cat #WP6111560, XX1004700, XX1004705, Darmstat, Germany). The pre-weighed filter, plus the wet filamentous biomass is dried at 50° C. for 4 h in the Benchmark Scientific Incu-Shaker Mini (Edison, N.J.) and then weighed on a Mettler Toledo scale model MS3035 (Columbus, Ohio).

The filamentous acidophilic MK7 fungal strain has a specific growth rate of about $0.024 \text{ h}^{-1}$ in the 10 L reactor (FIG. 4) and growth during the exponential phase will follow the equation:

$$x = x_o \exp^{\mu t} \tag{Eqn 1}$$

Where x is the final biomass, $x_o$ is the initial biomass, $\mu$ is the specific growth rate, and t is the time. For use as inoculum in the tray reactors, the culture cell density in the 10 L reactor should be above 6 g/L dry weight and in the late exponential growth phase (FIG. 4; exponential growth is the period of growth in a culture when cell numbers are continuously doubling; late exponential growth is the period just prior to cessation of exponential growth when cell growth rates begin to decline). If culture medium with lower cell densities is used for inoculum, it will result in significantly slower biomat formation (lag phase that is longer than 2 days) and is thus not desirable.

Inoculum is defined herein as essentially composed of planktonic cells, which are defined as single cells that are not clumped or aggregated together and are about 4 microns in width to 5-20 microns in length.

To inoculate surface tray reactors for surface fermentation or solid substrate surface fermentation, the liquid culture was removed from the 10 L reactor via a port near the bottom of the reactor while continuously being mixed by bubbling. The culture to be used for inoculum was removed in an aseptic manner by spraying the inside of the port with 70% isopropanol/30% deionized water mixture, then opening the valve to allow about 25 mL of culture to be expelled and thus rinse the valve. This waste inoculum culture was disposed. The inoculum culture is added directly to the tray reactor medium as described in Example 3.

Example 4: Growth of Strain MK7 in Tray Reactors Via Surface Fermentation

Figure 5A:
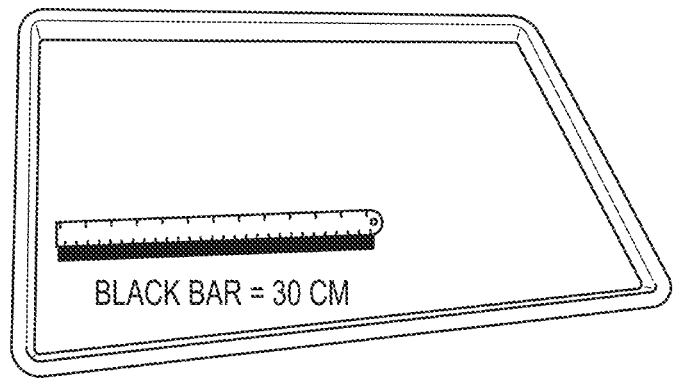
FIG. 5A: Trays used as tray reactors for producing biomat. The ruler in the tray is 31.75 cm (12.5 inches) long.
Figure 5B:
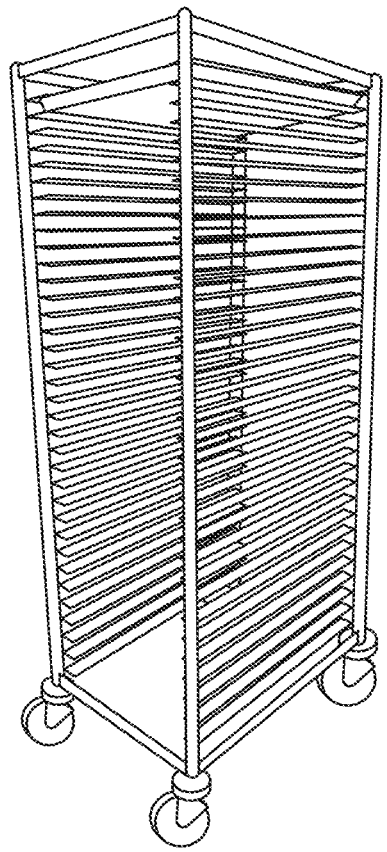
FIG. 5B: Bioreactor consisting of a tray rack system used to hold 39 plastic trays. The whole reactor is wrapped in Saran®-like clear plastic wrap.

Filamentous acidophilic MK 7 fungal strain, were grown in shallow tray reactors. It should be noted that different tray sizes are amenable to the teachings of this innovation. In this example, the inside dimensions of the polyethylene trays were 41.27 cm wide by 61.28 cm long with 2.54 cm tall sidewalls (total surface area available for mat growth=0.253 m²; FIG. 5; Winco, Idaho Falls, Id.). It is desirable that trays be clean of debris and chemicals as well as sterilized prior to use to minimize potential contamination. Consequently, prior to use, the trays were thoroughly washed with soap and warm drinking quality tap water (50-70 C), thoroughly rinsed with the warm tap water for 1 minute, and removal of all soap residues was validated. This was followed by spraying all surfaces of the trays until all surfaces were wetted with a solution of 70% isopropanol/30% deionized water (18.2 Mohm) and wiping the trays with gloved hands using a paper towel soaked in the alcohol mixture. Trays were then placed inside a rack system such that said tray can accept and hold liquid medium (described below) without spilling and allowed to dry.

The tray and rack system for used for the surface fermentation process described here provides all the necessary components to form a biomat and enable rapid growth of the biomat. The rack system used to hold the reactor trays was a chrome-coated steel, 39 tray rack purchased from Global Equipment Company (Chicago, Ill.; FIG. 5A, B). Clear plastic Saran®-like wrap 16 inches wide (Costco, Bozeman, Mont.) was used to wrap and enclose the rack system, and isolate the trays from the surrounding room. This enabled control of environmental conditions (humidity, air flow) and minimized contamination (FIG. 5A, B). Humidified sterile air was blown into the enclosed rack at a rate of 800 mL/minute via bubbling through 200 mL of deionized water (18.2 Mohm), water temperature 22-30° C. (to humidify the air) and passage through an autoclaved 0.2 um filter (Millipore, Cat #SLFG85000, Darmstat, Germany) to remove microorganisms. Ideally, the rate of airflow is such that it creates a slight positive pressure in the rack system (>0.1 psi) thereby minimizing the amount of airborne contaminants from entering the enclosed tray and rack system until the biomat reaches the desired density and/or consistency.

While the microbial mat is active, cells are respiring; that is, producing carbon dioxide and heat, as well as consuming oxygen. Accumulating carbon dioxide can reduce availability of oxygen and should be limited. Thus, airflow should be such that it flushes out carbon dioxide that is produced and accumulated during microbial respiration. Additionally, airflow should be such that it removes excess heat generated during microbial respiration and supplies adequate oxygen to the respiring cells. Airflow should be adjusted to meet these needs. For example, as need increases when a greater number of trays are used, airflow should be increased to meet the increased temperature and atmospheric needs. Airflow should not be strong enough to perturb the fungal hyphae and inhibit their growth and function. Ideally, in a tray system airflow would result in air flow across the trays. In one embodiment, the airflow can be generated by a fan that passes air through a 0.2 um filter and across the mats. The fan speed and resulting air flow can be controlled by a smart sensor/actuation system based upon temperature, carbon dioxide and oxygen sensors positioned in the rack.

Temperature of the tray system ranged from 250±2° C. during growth. Temperature was measured using Thermo-Scientific Genesys 10S Series, Biomat 3S, Evolution 60S software and sensor system (Thermo Fisher. Waltham, Mass.). The thermocouple sensors were placed 20 mm inside the tray rack system at mid-height and at the top of the tray rack system.

MK7-1 medium was prepared as described in Example 2 [addition of nutrients, pH adjustment, boiling and cooling to room temperature (~23° C.)]. After medium preparation, inoculum culture was obtained from the inoculum reactor (see Example 3) and added at a rate of 7.5% (volume to volume) of the MK7-1 medium in a pot. For example, 113 mL of inoculum was added to 1.5 L of medium in the pot. This ratio of inoculum to medium provides adequate conditions for rapid growth of the cells and mat formation. In this embodiment, the desired dry cellular filamentous biomass after inoculation of the fresh medium is 0.45 to 0.75 g/L. However, densities ranging from 0.01 to 100 g/L could potentially be used to successfully generate a biomat in the present tray system. Reducing the inoculum to medium ratio results in slower growth as described in Example 3.

The volume of carbon substrate to the volume of medium impacts the resulting rate of biomass production. In general, when the aforementioned ratio is too small, the growth rates slow down due to lack of available carbon; that is, they become carbon limited. When the aforementioned ratio is too large, the resulting osmotic pressure becomes too great and the biomass growth rates diminish. Furthermore, when carbon is limited, resulting biomass density and biomass cohesiveness is small, thereby diminishing the processing and handling advantages offered by the surface fermentation process. For example, the filamentous fungal strain designated as MK7 has optimal growth conditions when the aforementioned ratio is between 8-15%.

The medium/cell suspension was mixed with a sterilized large plastic spoon (30 cm long, sterilized by rinsing with the alcohol mixture) and 1.5 L of the resulting mixture was added to each tray using a sterilized (rinsed with the alcohol mixture) graduated cylinder. After all trays were loaded into the rack system, the rack system was wrapped with the clear plastic.

Figure 6:
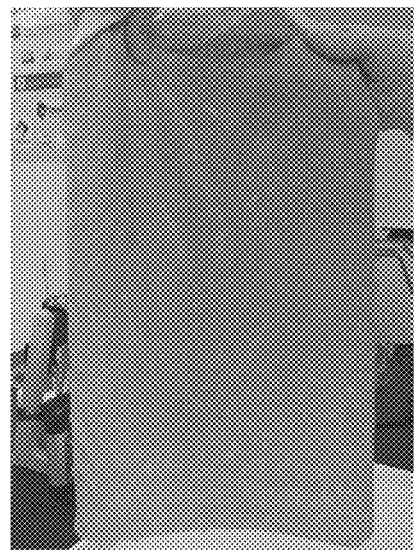
FIG. 6. Harvested strain MK 7 biomat cultivated for high-lipid production under limited nitrogen conditions (C:N ratio of 40:1) after 8 days of surface fermentation in a 0.25 m² tray with 1.5 liters of MK7-1 medium and 125 g/L glycerol.

After 6 days of incubation, the resultant biomats were 3 to 10 mm thick with enough tensile strength and structural integrity so that they can be handled without tearing (FIG. 6). The biomats were harvested by first removing the clear plastic wrap around the rack system and removing the trays from the rack. Biomats were removed from the trays by hand, placed in a 12.7×23 cm Pyrex glass tray and gently rinsed for two minutes with drinking quality tap water. The rinsed biomats were either left on the glass tray and dried or placed in a 3.7 L plastic bag and frozen. To dry, the biomats were placed in a temperature controlled oven and heated at 60°±1° C. for 45 minutes to deactivate many of the enzymes and limit biochemical transformations within the mat, followed by heating at 50°+1° C. until the dry weight did not change (approximately 48-72 hours). Average dry weights of biomats produced given the above conditions were 81 g dry filamentous biomass per tray for the filamentous acidophilic MK7 fungal strain. This is equivalent to 54 g/L, 324 g/m² surface area and a productivity of 0.37 g/L/hour. Average moisture content of the undried biomat was 0.17 dry filamentous biomass/g or 83% liquid.

Figure 7:
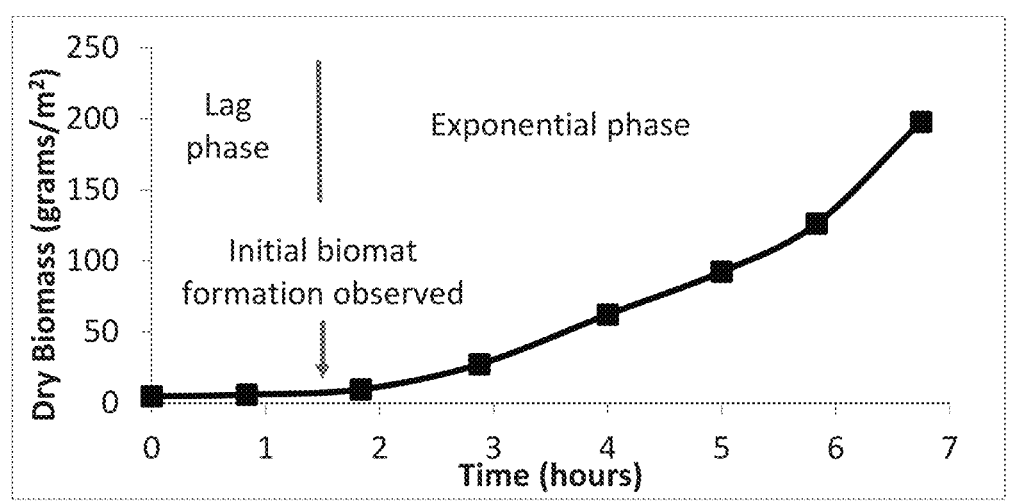
FIG. 7. Typical growth pattern for strain MK7 in shallow trays showing lag phase, where biomass accumulation rates are relatively slow 0-1.5 days), and time of biomat formation (arrow, 1.5 days) when exponential growth begins. Biomat grown in MK7-1 medium with 7.5% glycerol and 30:1 C:N ratio.

Cellular growth in trays typically occurs according to the growth curve shown in FIG. 7. Cells grow in a planktonic (homogenous/evenly distributed cells throughout the medium) state until about 48 hours of growth. After 48 hours, the cells aggregate at the surface of the medium and begin to form a biofilm; in other words, a microbial mat where cells are intertwined and stuck together. The mat is a very thin skin at first, but continues to grow rapidly until some limiting factor such as lack carbon substrate or other nutrient limits growth.

Due to the sensitivity of the biomat to disturbance and consequent decline of growth, it is important that trays remain undisturbed and the integrity of the biomat is maintained during the entire growth period. Disturbances that impact the biomat include excessive shaking of the tray, applying pressure to the mat, applying liquid to the surface of the biomat, rapid air flow across the biomat, disturbing, breaking or compression of the hyphae, or physical disruption of the mat itself. These types of disturbances result in loss of the advantages of growing a biomat, which include rapid growth rates and high filamentous biomass accumulation per liquid volume and surface area.

It is hypothesized that the aerial hyphae and mycelia play an important role in supplying oxygen for respiration of cells in the entire biomat. Thus, the formation, growth and function of aerial hyphae/mycelia is important for rapid growth of the biomat. Consequently, any disturbance that impacts formation or growth of these hyphae/mycelia results in a decline of biomat growth.

The surface fermentation method and medium described above provides all the necessary components to form a biomat and enable rapid growth. A wide variety of tray systems were tested using the above concepts and nearly equivalent productivity per unit area was obtained. For example, using 7.5% glycerol and a 10:1 C:N ratio, productivities remained constant at about 44 $g/m^2/d$ during the growth phase as the surface areas of the bioreactors were increased from 0.02 to 1 $m^2$.

Figure 8:
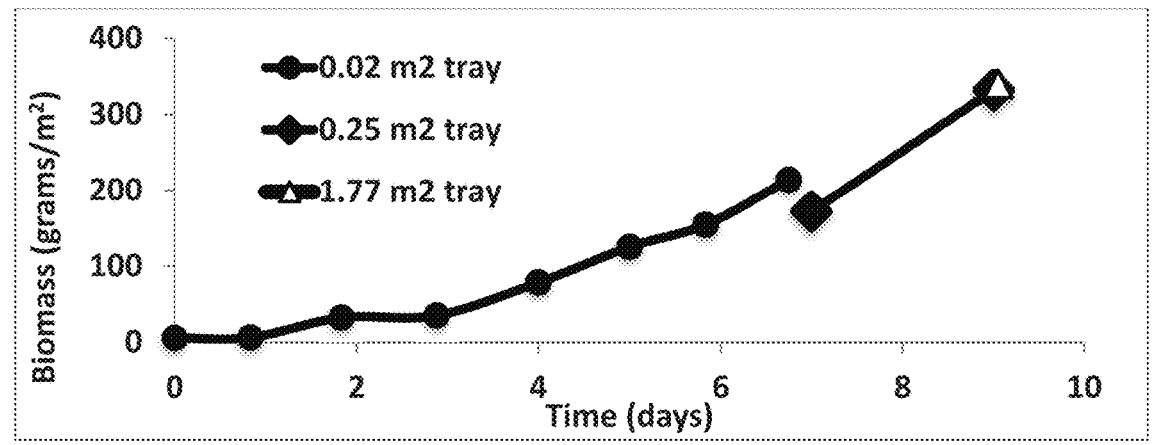
FIG. 8. Dry weights of strain MK7 biomats grown on glycerol in tray sizes ranging three orders of magnitude.

Example 5: Effects of Tray Size on Filamentous Fungi Biomat Growth and Productivity To test the effects of tray size on biomat growth and productivity, strain MK7 filamentous fungi biomats were grown on MK7-1 medium with 7.5% glycerol in 0.02 $m^2$ Pyrex® glass trays, 0.25 $m^2$ polypropylene trays and a 1.77 $m^2$ plastic lined tray. Liquid medium volume to surface area ratios were 6 $L/m^2$ for all treatments. Growth rates were only minimally affected by tray size and linear growth rates were observed after 6 days (FIG. 8). Dry biomass productivity was 1.32, 1.54, and 1.57/$m^2$/h for the 0.02, 0.25, and 1.77 $m^2$ trays, respectively.

Example 6: Growth of Strain MK7 on Different Media

The growth characteristics of filamentous acidophilic MK7 fungal strain growth characteristics (i.e. growth rate, cell density, substrate conversion efficiency, mat formation) vary dramatically as a function of choice of growth medium and whether the cultures are grown in SSF/submerged fermentation or SSSF/surface fermentation conditions. The filamentous acidophilic MK7 fungal strain was cultivated on a historical (May 2009 to November 2012) medium MK7A, initially designed to mimic the chemistry found in the organism's natural environment in Yellowstone National Park but with increased nitrogen, phosphorous, calcium and magnesium concentrations to match a nutrient source found beneficial for other filamentous fungi (Table 2; MK7A). MK7-1 medium was developed to enhance and improve the filamentous acidophilic MK7 fungal strain growth characteristics, especially in regards to mat formation by surface fermentation (Table 2). Specifically, phosphate, calcium and magnesium and nitrogen were increased and an additional nitrogen source was added (urea). Increasing calcium, magnesium and adding urea specifically increased growth rates and enhanced mat formation.

TABLE 2

Chemical components of historical medium MK7A (submerged fermentation) compared to Modified MK7-1 designed for high-density filamentous biomass formation by surface fermentation.

| MK7A Medium | | Modified MK7-1 Medium | |
|---|---|---|---|
| | g/L | | g/L |
| NH4NO3 | 3.5 | NH4NO3 | 12.9 |
| KH2PO4 | 2.0 | Urea | 4.3 |
| CaCl2•2H2O | 0.4 | KH2PO4 | 10.0 |
| MgSO4•7H2O | 0.3 | CaCl2 | 2.0 |
| MnSO4•7H2O | 0.5 | MgSO4•7H2O | 2.0 |
| Micronutrients** | mg/L | Micronutrients* | mg/L |
| FeCl3•6H2O | 20.00 | FeSO4•7 H2O | 4.99 |
| ZnSO4•7 H2O | 0.22 | ZnSO4•7 H2O | 2.20 |
| CoSO4 | 0.01 | MnCl2•4 H2O | 0.51 |
| CuCl2•2 H2O | 0.05 | CoCl2•6 H2O | 0.16 |
| NaMoO4•2H2O | 0.03 | CuSO4•5 H2O | 0.16 |
| Na2B4O7•10H2O | 4.50 | (NH4)6Mo7O24•4 H2O | 0.11 |
| VOSO4•2H2O | 0.3 | H3BO3 | 0.11 |
| Glucose g/L | 40.0 | EDTA, free acid | 39.3 |
| pH | 2.5 | Glucose g/L | 125.0 |
| C:N ratio | 16.3 | pH | 2.8 |
| | | C:N ratio | 7.5 |

Initial experiments with MK7A medium were done exclusively under submerged fermentation conditions in shaker flasks. Maximum growth rates, conversion efficiency (g of carbon substrate converted to filamentous biomass) and highest filamentous biomass produced under these conditions were 0.072 g/L/h; 22%; and 8.6 g/L, respectively (Table 3).

TABLE 3

Growth characteristics of the filamentous acidophilic MK7 fungal strain under a variety of conditions.

| Biorector | Carbon source | Average Growth Rate (g/L/hr) | Maximum Biomass Produced g/L | Maximum Biomass Produced g/m^2 | Biomass production rate g/m^2/day | Maximum biomass Produced (days) | Conversion Efficiency |
|---|---|---|---|---|---|---|---|
| Submerged - aerated | 4% glucose minimal | 0.072 | 8.6 | | | 5 | 22% |
| Submerged - aerated | 4% glucose MK7-1 | 0.126 | 15.1 | | | 5 | 38% |
| Submerged - aerated | 7.5% Glycerol MK7-1 | 0.28 | 24.1 | 23 | | | 31% |
| 0.02 m^2 Tray - 100 ml | 4% glucose MK7-1 | 0.135 | 19.5 | 110 | 18.3 | 6 | 49% |
| 0.02 m^2 Tray - 100 ml | 12.5% Glycerol MK7-1 | 0.44 | 64.7 | 324 | 52.9 | 6 | 52% |
| 0.25 m^2 Tray - 1.25 L | 12.5% Glycerol MK7-1 | 0.46 | 66.2 | 331 | 55.2 | 6 | 53% |

To increase cell density, MK7A medium was utilized in conjunction with surface fermentation conditions. Biomats formed in carbon concentrations between 4-15% with glucose or sucrose and 4-30% with glycerol. Urea was found to increase rates of production in surface fermentation conditions and $NH_4NO_3$, $NH_4PO_4$, $NH_4SO_4$ are alternative sources of $NH_4$. Addition of urea has benefits of less expensive market prices as compared to other $NH_4$ sources. 12.5% carbon substrate was found to be ideal for increasing filamentous biomass densities up to 180 g/L (density after biomat removal from tray) and optimizing growth rates.

High density biomats produced with surface fermentation and MK7-1 medium have a number of advantages over submerged fermentation conditions (with either media) including: (1) increased filamentous biomass density up to 180 g/L (density after biomat removal from tray) compared to maximum of 24.1 g/L with submerged fermentation (Table 3), (2) increased growth rates up to 0.46 g/L/h compared to maximum rates of 0.28 g/L/hr under submerged conditions, (3) increased density of carbon feedstock from 7.5 to 12.5% for maximum growth rates, (4) much easier harvesting conditions for filamentous biomass especially when high density filamentous biomass is produced (e.g. centrifugation not necessary), (5) there is no need to aerate the filamentous biomass as compared to large complex aerated bioreactors for submerged fermentation (6) much more scalable and expandable to use surface tray systems compared to very large commercial submerged fermenters (7) less liquid waste.

Figure 9:
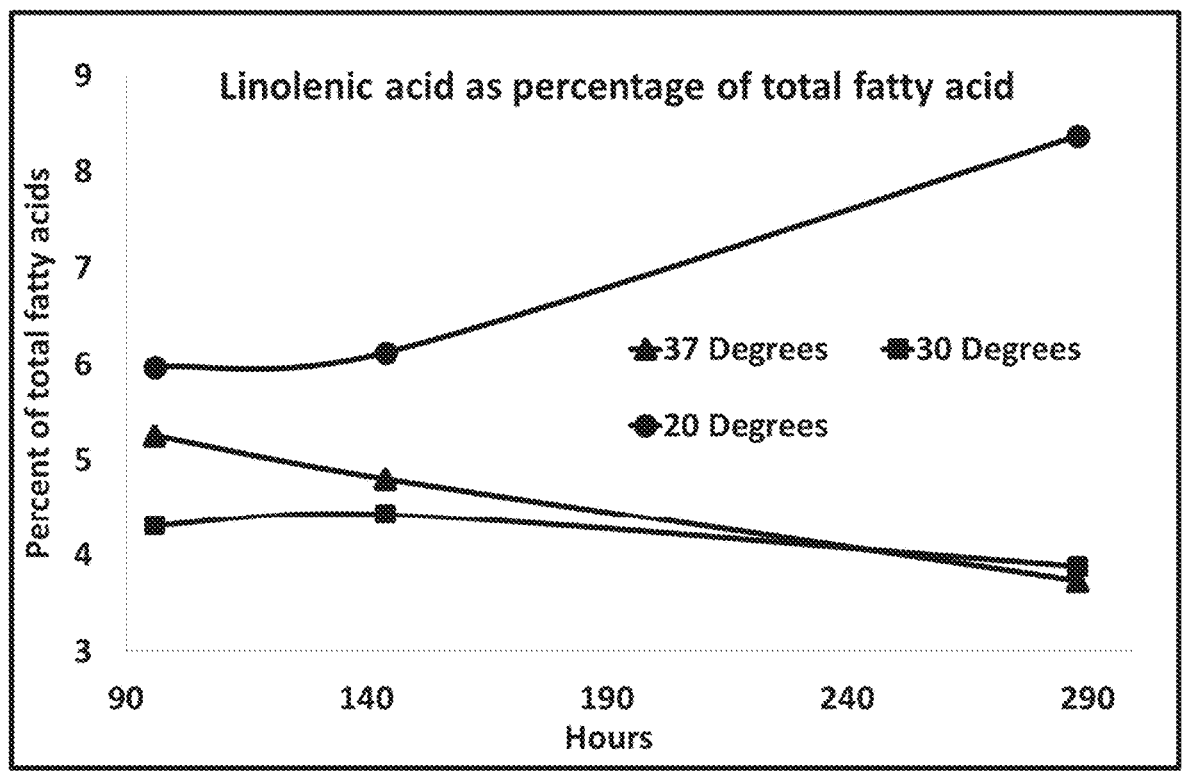
FIG. 9. Linolenic acid production by strain MK7 as a function of cultivation duration and temperature. 4% glycerol surface fermentation; pH 2.8 and MK7-1 medium.

Decreasing C:N ratios to <10:1 were also highly beneficial for filamentous biomass production and increased the levels of protein versus lipids. Historically, MK7A medium was designed for production of lipids by the filamentous acidophilic MK7 fungal strain especially at C:N ratios above 30:1. Varying C:N ratios along with culture conditions allow for the tailoring of lipid concentrations in the filamentous acidophilic MK7 fungal strain biomass between 5 to up to 60% of weight of biomass. Fatty acid profiles for filamentous biomass were very similar between MK7A and MK7-1 media with various simple carbon substrates (e.g. glycerol, glucose, sucrose), but temperature was found to increase the concentration of polyunsaturated fatty acids with the omega-3 linolenic acid increasing over time at lower relative temperatures (FIG. 9).

Example 7. Growth of Strain MK7 on MK7A and MK7-1 Media

Strain MK7 filamentous fungi biomats were produced under surface fermentation conditions using MK7A and MK7-1 media with either sucrose or glycerol as a carbon source (feedstock). To evaluate filamentous fungi biomats produced from MK7A and MK7-1 media, five different media formulations were prepared: 1) 4% sucrose in MK7A medium, 2) 4% sucrose in MK7-1 medium, 3) 4% glycerol in MK7A medium, 4) 10% glycerol in MK7-1 medium, and 5) 12.5% glycerol in MK7-1 medium. The pH of all five media formulations was adjusted to 2.7 using appropriate additions of concentrated HCl followed by boiling for 10 minutes. After cooling to room temperature (~23° C.), a 7.5% volume/volume of strain MK7 inoculum in exponential growth phase was added to each media. The pH was readjusted to 2.7 and 250 mL aliquots of the inoculated media were added to sanitized 0.023 $m^2$ Pyrex® glass trays. The trays were then placed in a tray rack system and the mixtures of media with inoculum were allowed to incubate at 23°±1° C.

Based on results from previous experiments, it is expected that biomass will form on all of the media combinations. It is also expected that biomass will form more quickly on MK7A media relative to MK7-1 media. This is due to the more hospitable chemical conditions of the MK7A media for growth (e.g. lower ionic strength/osmotic pressure, lower ammonium concentration). In time however, filamentous fungi biomats that develop on the surface of the MK7-1 media will grow with a faster growth rate than biomass growing on MK7A media. That is, both systems have different growth rate curves with the MK7-1 media exhibiting fast growth in the early stages followed by reduced growth rates in the later stages. Conversely, filamentous fungi biomats grown on the MK7-1 media have initially relatively slow growth rates in the early growth stages followed by extremely rapid growth rates in the later stages of biomass growth. Ultimately, filamentous fungi biomats grown on the MK7-1 media become thicker and have greater tensile strength than biomats grown on MK7A media. It is expected that the significantly lower concentrations of nutrients in the MK7A media (e.g. N, P, K) will result in early nutrient limitation, causing growth inhibition with biomats that are not as thick or strong as biomats produced on MK7-1 media.

Example 8: Structure of Biomats Produced by Strain MK7

The structure of the biomat was determined by transmitted light microscopy. Here, biomats were produced from strain MK7 grown for 5 days on MK7-1 medium with 7.5% glycerol. Biomats were harvested, frozen (-20° C.), and dissected into 1 cm×1 cm square blocks before embedding in 10% gelatin (Sigma G2500-3000 Bloom gelatin, Sigma-Aldrich, Saint Louis, Mo.) in cryomolds (VWR 25608-916, Radnor, Pa.). The gelatin/tissue sample was flash-frozen by exposing the cryomolds to the vapor phase of a liquid nitrogen bath before placing at -20° C. overnight.

Cyrosectioning was accomplished using a Leica model 39475214 Cryosectioner (Leica, Wetzlar, Germany). Samples were removed from the cryomolds and coated with OTC tissue freezing medium (Leica 14020108926) prior to cryosectioning into 10-50 m thick slices. Sample slices were visualized and imaged using a transmitted light microscopy (Microscope: Zeiss AxioObserver; Camera: Zeiss AxioCam HRc, Carl Zeiss, Oberkochen, Germany).

With glycerol mats, at least two distinct layers were observed: (a) a dense bottom layer and (b) an aerial hyphae layer. In some samples at least three structurally different layers were visible: (a) a dense bottom layer, (b) an aerial hyphae layer and (c) a transition zone layer (see FIGS. 10A and B). Typically, the aerial hyphae layer is most visibly dominant, followed by the dense bottom layer, while the transition zone layer, when present and/or visible, is smallest. In some instances, for example the biomat shown in FIG. 10A, the visible ratio of the (a) dense bottom layer to the (b) aerial hyphae layer to the (c) transition zone layer was about 3.86 to about 9.43 to about 1. In another sample, such as the biomat shown in FIG. 18B, the ratio was about 1.7 to about 3.7 to about 1. There was no visibly distinct transition zone layer apparent in FIG. 18C.

Figure 11A:
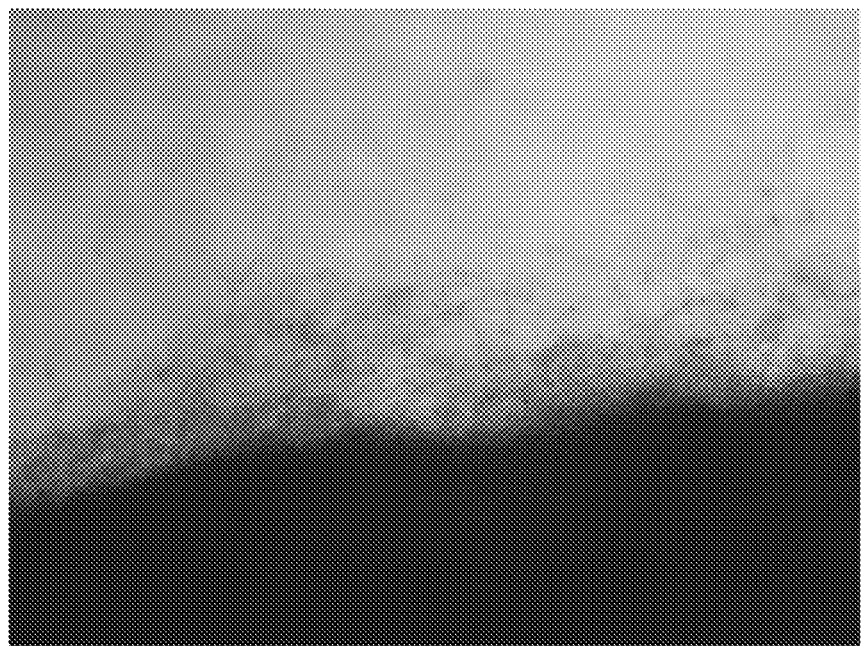
FIGS. 11A-D. Cross sectional micrographs of 5 days old MK7 biomat produced using MK7-Urea medium.
Figure 11B:

Additional optical imaging of an MK7-3 grown biomat indicated no lipids or pigments present in the top aerial hyphae layer as compared to the dense bottom layer (FIGS. 11A and 11B). Aerial hyphae are found extending from the mat and each is exposed to the atmosphere without liquid between the hyphae. This distinguishes them from hyphae/ mycelia in the other layer(s) of the mat, which are separated by liquid and/or an extracellular polysaccharide/protein matrix. Aerial hyphae are responsible for oxygen transfer and CO2 transfer. Oxygen accessibility results in oxygen absorbing hyphae in the top aerial hyphae layer. These aerial hyphae appear to be longer than the hyphae/mycelia found in the lower mat layer(s) (compare FIG. 11B with FIG. 11C). The aerial hyphae of the top layer also tend to have a preponderance of vertical orientation, that is they tend to be oriented perpendicular to the filamentous fungi biomat air interface.

Figure 11C:
Figure 11D:
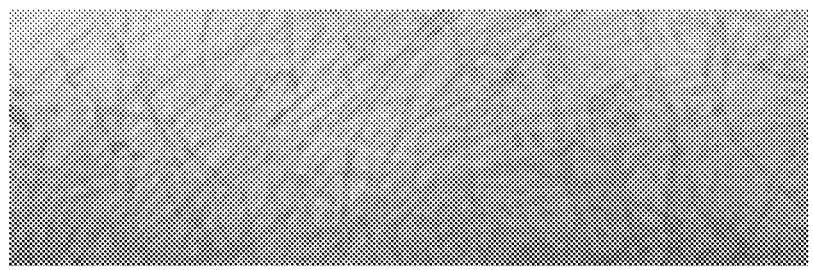

Vertical orientation was not as predominant in the hyphae of the dense bottom layer (FIG. 11C). Here, the hyphae tend to be intertwined and have a mix of orientations and have a preponderance of horizontal orientations. The hyphae of the bottom layer also appeared to contain a purple pigment, which was not evident in the top aerial layer. Preliminary experiments indicated that the bottom layer contains approximately 30% lipids and that the hyphae are embedded in a protein and/or polysaccharide matrix. The bottom layer hyphae are also the primary storage area for pigments, lipids, carbohydrates, and protein.

Biomats produced from strain MK7 grown on (1) MK7-1 medium and (2) MK7-3 medium, were harvested after 5 days and frozen at 20° C. The thickness of both biomats ranged from 2 to 4 mm. One cm² square sections were cut from the two frozen biomats in triplicate and then cut in half latitudinally, producing top and bottom half cross sections, each approximately 1.5 mm thick.

The average density for the biomat grown in MK7-1 media was 0.131 g/cm³ for the top latitudinal section (standard deviation=0.068) and 0.311 g/cm³ for the bottom latitudinal section (standard deviation=0.032). The ratio of top to bottom densities was 0.42.

For the biomat grown in MK7-3 medium, the average density for the top latitudinal section was 0.102 g/cm³ (standard deviation=0.048) while the average density for the bottom latitudinal section was 0.256 g/cm³ (standard deviation=0.010. The ratio of top to bottom densities was 0.40.

Example 9: Tensile Strength of Biomat Produced by Strain MK7

The tensile strength of an MK7 biomat grown for 5 days on MK7-3 media was evaluated. Here, a 25.4 cm wide, 46 cm long, 3.5 mm thick mat was used. The water content of the mat was about 85%, equating to approximately 15% dry weight. The total dry weight was 70 g/0.25 m² tray or 280 g/m². The mat had a density of 0.08 g/cm³.

To measure tensile strength, one end of the mat was clamped into a stationary position while the other end was clamped to a free moving apparatus. The free moving apparatus was itself attached to a scale that measures applied tension. A steady and slow tension was applied to the mat by pulling on the scale over several seconds until the mat broke. The measured tension required to break/rip/tear the mat ranged from 0.28 kg/2.54 cm of mat width to 0.58 kg/2.54 cm of mat width, which is equivalent to 0.11 kg/cm of mat width to 0.23 kg/cm of mat width. The average was 0.5 kg/2.54 cm mat width, or 0.2 kg/cm mat width.

Example 10: Growth of Strain MK7 Biomats on Crude Glycerin

Dense strain MK7 biomats were produced in 8 days using crude glycerin as a carbon and nutrient source (feedstock). Crude glycerin, a by-product of biodiesel production, was obtained from W-2 Fuels (Product Code GL32000, Batch 4300, CAS No. 56-81-5, Adrian, MI). The crude glycerin was comprised of 75-85% glycerin, 2-10% water, 2-5% salts, 1-2% fats, oils or esters, and <1% methanol.

A 7.5% concentration of crude glycerin in drinking quality tap water (weight:volume) was supplemented with either full-strength or ½ strength MK7-1 medium salts to create 11 L of full strength and ½ strength MK7-1 medium. The pH of these solutions was adjusted to 4.8 followed by boiling for 10 minutes. After cooling to room temperature (~23° C.), a 5% volume:volume strain MK7 inoculum prepared as described in Example 3 was added to the medium. The pH was readjusted to 4.8 and 1.5 L aliquots of the inoculated crude glycerin medium were added to sanitized polypropylene 0.25 m² trays before placing the trays in a rack system.

The mixtures were incubated at 23±1° C. and resulted in flexible, relatively dense biomats that were about 4 mm thick after 8 days at which time they were harvested. Biomats were dried at 50° C. for 72 h and the average dry weights±standard deviations were 30.3±3.1 g (n=6) for the full strength media treatment and 30.2±2.8 g (n=8) for the ½ strength media treatment. The average conversion of glycerin to dry biomat was 34% and the density of the moist mats on a dry biomass weight basis was 0.03 g/cm² for both treatments.

Example 11: Hyphael/Mycelial Structure of Strain MK7 Biomats Grown on Wheat Distillers Solubles Consolidated strain MK7 filamentous fungi biomats were produced in 7 days using dried wheat distillers solubles (ds) as the carbon and nutrient source (feedstock). The wheat ds were comprised of 31.5% protein, 8.6% oil, 2.8% starch, 13.5% sugar, 2.7% fiber, 8.5% ash, 0.19% calcium, 0.29% magnesium, 1.7% potassium, 0.78% phosphorus, and 3.5% sulfate. Two growth media treatments were prepared: Treatment 1 used 5% ds dry weight in water and Treatment 2 used 5% ds dry weight in ½ strength MK7-1 salts medium. The pH of the mixtures was adjusted to 3.4. The mixtures were inoculated with 7.5% (volume:volume) of strain MK7 inoculum prepared as described in Example 3 and 175 ml of that medium was added to alcohol sterilized 12.7×12.7 cm plastic trays. Filamentous fungi biomats were harvested after 7 days of incubation at room temperature (~23° C.). Biomats grown on 5% ds as the sole carbon and nutrient source (Treatment 1, without MK7-1 salts) were an average of 2.7 mm thick (n=3 trays), showed no distinct layering, and had an average dry weight of 0.83 g with an average density of 0.019 g/cm³ and a conversion efficiency of approximately 10%. No aerial hyphae were observed and the mats were saturated with liquid throughout; i.e. the top surface of the mats were at the surface of the liquid.

Biomats grown on 5% ds supplemented with MK7-1 salts (Treatment 2) were an average of 6.4 mm thick and had an average dry weight of 3.11 g with an average density of 0.030 g/cm³ and a conversi8on efficiency of approximately 40%. These mats developed an extensive fluffy white aerial hyphae system that was about 4-7 mm thick immediately above a distinct denser layer that was about 0.9 mm thick. The density of the upper layer was 0.011 g/cm³ and the density of the lower layer was 0.148 g/cm³.

Example 12: Growth of Strain MK7 Filamentous Fungi Biomats on Corn Steep Liquor and Corn Steep Liquor/Starch as the Carbon and Nutrient Source Dense strain MK7 filamentous fungi biomats were produced in as little as 4 days using corn steep liquor as the sole carbon and nutrient source (feedstock). Further, corn steep liquor with 5% starch addition was also shown to be capable of producing dense filamentous fungi biomats. Corn steep liquor is a viscous by-product of corn wet-milling and has a composition of amino acids, vitamins, and minerals that makes it suitable as a supplement for microbial fermentations. The corn steep liquor used in this example was purchased from Santa Cruz Biotechnology, Inc. (Dallas, Tex.; Lot #B0116). These experiments demonstrated the use of corn steep liquor as a replacement for MK7-1 nutrients. Treatments included 10% and 20% corn steep liquor as the sole carbon and nutrient source, and 10% and 20% corn steep liquor plus 5% starch (each) with the starch providing additional carbon for filamentous fungi biomat growth.

Four batches of media were prepared by adding 10% or 20% corn steep liquor to 1 L volumes containing 0 or 50 g dry starch. The media was adjusted to pH 3.6 by adding a suitable amount of HCl and boiled for 15 minutes in a suitable container. After cooling to room temperature, the pH of the mixture was readjusted to 3.6 and the mixture inoculated with 7.5% strain MK7 inoculum as prepared in Example 3. Aliquots of 175 ml of media were added to five square trays (0.016 m$^2$ surface area/tray) and the prays incubated in a rack system at 23°+1° C. Filamentous fungi biomats were harvested after 6 days. The average final pH for the corn steep liquor treatments at 10%, 20%, 10%+ starch, and 20%+starch were 3.97, 3.69, 4.23, and 4.15, respectively. The average biomass weight±standard deviation for these treatments were 1.1±0.2, 0.1±0.1, 2.3±0.1 and 2.1±0.2 g, respectively.

Example 13: Conversion of Cattle Feedlot Lagoon Water to Filamentous Fungi Biomats Growth experiments were conducted using cattle feedlot lagoon water as the sole carbon and nutrient source. The initial dissolved organic carbon content of the waters was 4 g/L and initial total dissolved nitrogen content was 0.8 g/L.

Feedlot lagoon water was adjusted to pH 2.6 with concentrated HCl and inoculated with 7% strain MK7 inoculum as prepared in Example 3. Sterilized 0.25 m2 polypropylene trays were filled with 1.5 L of the inoculated waste water and placed into a tray rack system for incubation at 24°±1° C. Filamentous fungi biomats began to form on the surface of the liquid 2 days after inoculation. After ten days, the filamentous fungi biomats and remaining liquid were collected in a single vessel and dried prior to analysis for total C and N using a Costech total C and N analyzer (ECS 4010, Costech Analytical Technologies, Valencia, Calif.). The average dry biomass produced per tray was 6.531 g (n=2). Analyses of the mats and residual liquid revealed that about 77% of the carbon and 99-100% of the nitrogen was removed from the feedlot lagoon wastewater by the mats (method detection limit~1%). Carbon and nitrogen removal rates for the system were 6.8 and 1.2 mg/L/h when averaged across the 10-day period. According to present understanding, it is possible to remove most of the C and nearly all of the N from feedlot waters by acidifying the lagoon to pH 2.6 with HCl and inoculating with strain MK7. It is further possible to treat lagoons directly, resulting in a floating filamentous fungi biomat on the feedlot water on site that can then be harvested for subsequent use.

Example 14: Growth of Strain MK7 Biomats on Acid Whey Surrogate Medium

Dense strain MK7 biomats were produced from Acid Whey Surrogate Medium (AWS) in 7 days. Composition of the AWS medium was based on the typical composition of acid whey as described in Tsakali et al. (2010). Composition of the Tsakali medium and the AWS Medium used in this Example is described in Table 4.

Figure 18:
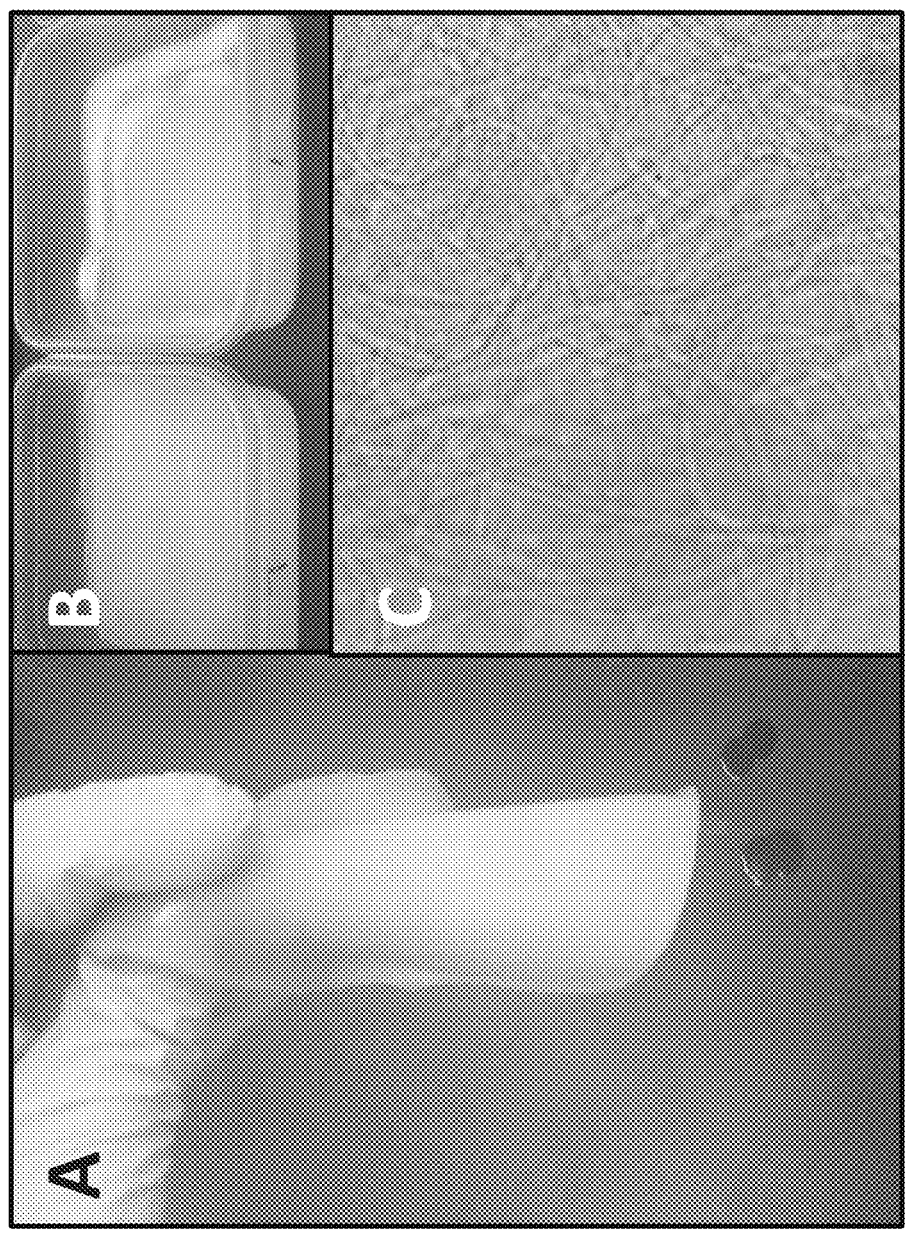
FIG. 18. Strain MK7 biomats after 7 days of growth on Acid Whey Surrogate mediums (AWS) at an initial pH of 4.8 (A, B, C). Transmitted light microscope image (400×) of biomat (C) showing filamentous nature of the material.

Biomats were produced in sterilized 12.7×12.7 cm (0.016 m$^2$) polypropylene trays using 87 mL of pH 4.8 AWS medium. The medium was prepared by mixing the ingredients listed in Table 4 in a 1 L Erlenmeyer flask, adjusting the pH to 4.8, and then boiling for 10 minutes. After the medium cooled to about 23° C., a 7.5% volume (volume/volume) of inoculum in exponential growth phase was added to the flask. This inoculum was generated as described in Example 3. Aliquots of 87 mL of the inoculated culture medium were added to isopropyl swabbed trays (Example 3) and the trays were placed on a larger (0.25 m$^2$) tray mounted in the tray rack system as described in Example 3. The cultures were allowed to incubate at 25±1° C. resulting in relatively dense biomats that were harvested after 7 days (FIG. 18). The mean pH value of the residual liquid after 7 days was 6.9±0.1. Thus, the growth process neutralized the pH of AWS from 4.8, typical of acid whey, to near neutral (~7). Transmitted light microscopy revealed the filamentous nature of the biomats generated on AWS medium (FIG. 18). The average thickness of the moist biomats was 4±0.5 mm. Biomats were dried at 50° C. for 30 h and the resulting average dry weights were 1.88±0.2 g. The average density of the moist biomats was 0.29 g/cm$^3$. The average conversion of dry feedstock (lactose and total proteins) to dry biomat was 42.2%.

TABLE 4

Composition of a typical acid whey as described in Tsakali et al., 2010, and the Acid Whey Surrogate medium (AWS) used in this Example for growing MK7 biomat.

| | Tsakali (%) | AWS (%) |
|---|---|---|
| Water | 94.5 | 94.5 |
| Dry Matter | 5.5 | 5.5 |
| Lactose | 4 | 4 |
| Lactic Acid | 0.4 | 0 |
| Total Protein* | 1 | 1 |
| Citric Acid | 0.1 | 0.1 |
| Minerals** | 0.6 | 1.3 |
| pH | 4.8 | 4.8 |

*Total protein source for AWS was whey protein concentrate as 100% Whey Protein GNC ProPerformance from GNC, Pittsburgh, PA.
**Mineral composition of AWS was ½ strength MK7-1 medium described in Table 1A but without glycerol.

Example 15: Growth of Strain MK7 Biomats on Acid Whey

Strain MK7 biomats are grown in 6 days using acid whey as the primary carbon and nutrient source. Biomats are produced in sterilized 12.7×12.7 cm (0.016 m$^2$) polypropylene trays using 125 mL of raw acid whey that has been subjected to a variety of treatments. The treatments are conducted to evaluate growth rates and biomass productivity after adjusting pH, adding select nutrients and/or heating to minimize the presence of competing microorganisms.

Acid whey volumes of 500 mL are added to previously sterilized 1 L Erlenmeyer flasks (heated to 125° C. for 10 minutes) and the liquid medium is subjected to the selected treatments (1-12) as outlined in Table 5. The pH is either not adjusted (average pH of acid whey is 4.8) or adjusted to pH 2.7 with concentrated HCl. Nutrient addition treatments include: no addition, 2.5 g/L of urea as a nitrogen source, or ½ strength MK7-1 as a full suite of nutrients prepared in the acid whey liquid as described in Example 1, minus the glycerol. Heat sterilization is conducted by boiling the acid whey liquid medium for 15 minutes after the other treatments (pH and or nutrient additions) are performed. After the media has cooled to about 23° C., a 7.5% volume (volume/volume) of inoculum in exponential growth phase is added to the flask. This inoculum is generated as described in Example 3. Aliquots of 125 mL of the inoculated culture medium are added to isopropyl swabbed trays (see Example 3 for sterilization procedure) and the trays are placed on larger (0.25 m$^2$) trays mounted in the tray rack system as described in Example 3. The cultures are allowed to incubate at 25±1° C. for at least 6 days.

TABLE 5

Treatment matrix used for evaluating acid whey as a nutrient medium for growth of strain MK7 biomats.

| Treatment | pH | Nutrient Addition | Heat Sterilization |
|---|---|---|---|
| 1 | not adjusted | no | no |
| 2 | not adjusted | no | yes |
| 3 | not adjusted | Urea | no |
| 4 | not adjusted | Urea | yes |
| 5 | not adjusted | ½ MK7-1 | no |
| 6 | not adjusted | ½ MK7-1 | yes |
| 7 | 2.7 | no | no |
| 8 | 2.7 | no | yes |
| 9 | 2.7 | Urea | no |
| 10 | 2.7 | Urea | yes |
| 11 | 2.7 | ½ MK7-1 | no |
| 12 | 2.7 | ½ MK7-1 | yes |

Example 16: Growth of Strain MK7 Filamentous Fungi Biomats on Anaerobic Digestate Dense strain MK7 biomats were produced in 7 days using anaerobic digestate as the sole carbon and nutrient source (feedstock). Anaerobic digestate is the lignin-rich solid residue that remains after the microbial fermentation of lignocellulose-rich biomass (e.g. corn stover, wheat straw, cattle manure) under oxygen limited conditions. Anaerobic digestate is considered resistant to further decomposition by microorganisms and for this reason is commonly used as a soil amendment or is burned to power steam generators for production of electricity.

Moist anaerobic digestate (500 g) was added to 2 L of drinking quality tap water forming a mixture. The native pH of this mixture was 5.5. The mixture was inoculated with 7.5% (volume:volume) of strain MK7 inoculum, prepared as described in Example 3. 200 ml of the resulting mixture was added to square 12.7×12.7 cm trays. Consolidated biomats formed on the surface and were harvested after 7 days of incubation at room temperature (~23° C.). The biomats had an average thickness of 2.6 mm and had an average dry weight of 0.62 g (n=3, standard deviation=0.03 g) and a corresponding density of 0.015 g/cm$^3$. The average conversion efficiency was 2.3%.

To enhance rates of anaerobic digestate conversion to microbial biomass, an additional experiment was conducted by supplementing the anaerobic digestate with Barley Medium, effectively using an augmented growth medium. The Barley Medium was used to stimulate growth and induce in situ enzyme production by strain MK7 for further degradation and conversion of anaerobic digestate to fungal biomass. The augmented Barley Medium was prepared by combining 1 L of tap water, 50 g of barley flower, 1 g yeast extract, 0.1 mL glucoamylase (Distillate VHP, Dupont), 0.1 mL alpha-amylase (SPEZYME ALPHA, 13,775 AAU/g, Dupont) and 0.1 mL beta-glucanase (Optimash TBG, Dupont). The mixture was heated to 65 C and stirred for 15 minutes while at 65 C. Afterward, the mixture was boiled for 15 minutes to deactivate the enzymes. The mixture was then cooled to room temperature.

The protocol described above for the anaerobic digestate experiment was repeated with exception that the tap water was substituted with augmented Barley Medium and the total volumes of each component used were reduced by one half. The average conversion of anaerobic digestate to biomats was 6±2% after subtraction of biomass generated in the control treatment where no anaerobic digestate was added.

Example 17: Growth of Other Filamentous Fungi in Tray Reactors

The growth of *Rhizopus oligosporus* and *Fusarium venenatum* were evaluated using the surface fermentation techniques described in Examples 1, 2, and 3 for strain MK7.

*Rhizopus oligosporus* is extensively used for Tempeh (human food) production around the world. *Rhizopus oligosporus* strain ATCC 22595 was obtained from ATCC on Oct. 1, 2015. The pure culture sample of *R. oligosporus* obtained from ATCC was placed on MK7-1 agar medium in Petri plates as described in Example 2.

*Fusarium venenatum* used in Quorn™ food production was culled from a Quorn Chik'n Nuggets package (UPC code: 33735-00006) purchased on Jan. 16, 2016 from Albertson's supermarket in Bozeman, Mont. To isolate *F. venenatum*, a sample (~0.25 cm$^2$) of Quorn™ Chik'n Nuggets containing *F. venenatum* was placed in 100 mL of sterile pH 5, MK7-1 medium in a 250 ml baffled shaker flask. The medium and flask were sterilized by boiling the medium in the flask for 20 minutes. The medium was allowed to cool to 23 C prior to addition of the Quorn™ sample. After 3 days of incubation at 23±1 C while rotating at 200 rpm, 1 mL of culture was removed and used to inoculate another identical flask and medium. After 3 more days of incubation in the same manner, a 50 µL aliquot of the culture was removed and plated on sterile MK7-1 agar medium (pH 4.8) in a sterile Petri plate.

Figure 12:
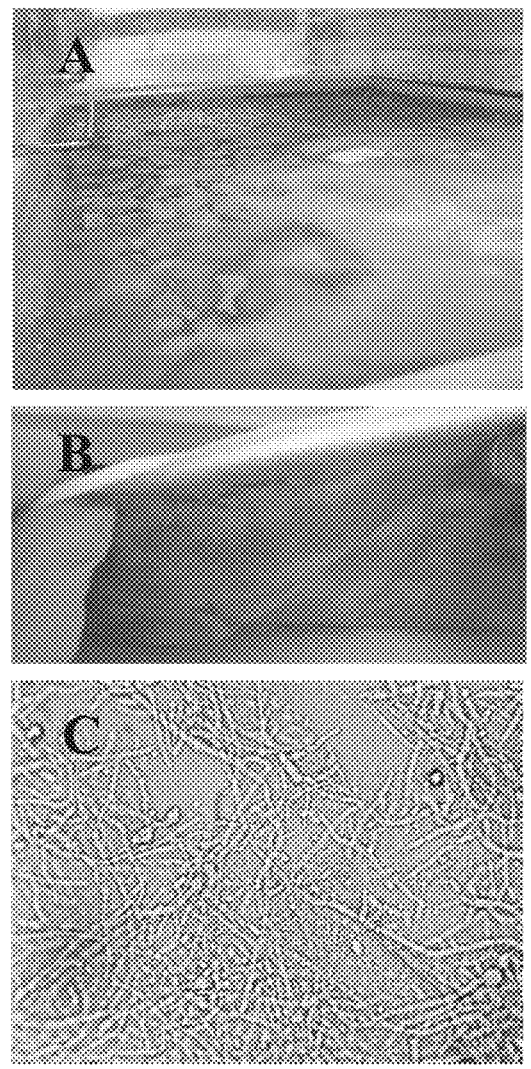
FIG. 12. A, B: Biomat of *Rhizopus oligosporus* grown on 0.25 m² tray for 6 days using MK-7 medium at pH 4.1 with 5% glycerol. C: 400×light microscope image of *Rhizopus oligosporus* hyphae in mat.
Figure 13:
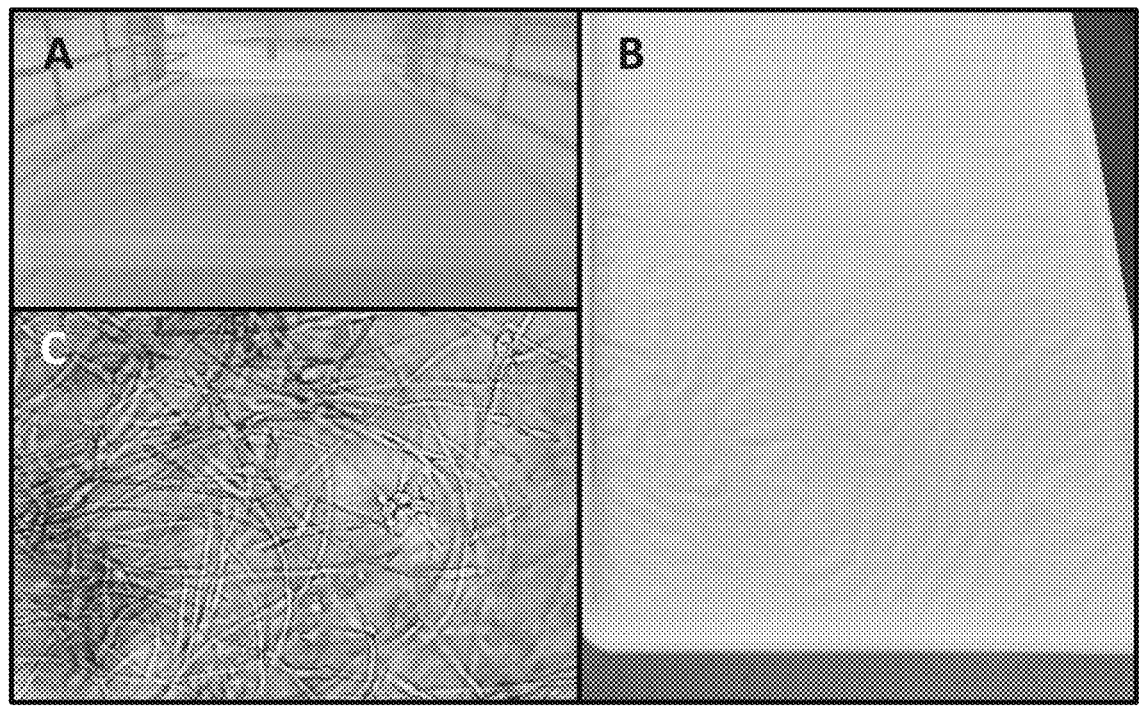
FIG. 13. Images of *Fusarium venenatum* grown in 0.25 m² tray reactor after A: 4 days, and B: 6 days. The biomats were grown using MK7-1 medium at pH 5.0 and 12.5% glycerol. Image C shows the hyphal form of *F. venenatum* taken a 400× magnification using a light microscope. Under these conditions, *F. venenatum* produced an average of 71 g of dry biomass per tray for two trays.

The mycelial mats that developed on the *R. oligosporus* and *F. venenatum* plates were used to inoculate 350 mL of MK7-1 medium in sterile 1 L baffled shaker flasks as described in Example 3. After 5 days of growth in the shaker flasks as described in Example 3, the cultures were used as inoculum for tray reactors. Desirable inoculum for the tray reactors consists of microbiologically pure cultures with cellular density greater than 6 g/L that are in the late exponential phase (see Example 3). As described in Example 3, two trays containing 1.5 L of inoculated MK7-1 medium were prepared for each of the two organisms. The pH of the media was adjusted to 4.1 for *Rhizopus* and 5.0 for *Fusarium*. Images of the resultant cultures and mats are shown in FIGS. 12 and 13.

Example 18: Comparison of Filamentous Fungi Biomat Produced by Solid-State Fermentation (SSF) Compared to Biomass Produced by Solid Substrate Surface Fermentation (SSSF)

SSF Procedure

Solid-state fermentation (SSF) as referred to herein means the microbial fermentation process that occurs on solids at low water contents, typically below 50%.

MK7 SSF inoculum was prepared by the addition of 20 g glucose to 1 L Mandels and Reese medium in a 2 L glass vessel and autoclaved for 45 minutes at 121° C. at pH 4.5. 100 ml of the resulting medium was added to a 250 ml Erlenmeyer flask and inoculated with 0.25 g of strain MK7 from −80° C. glycerol stock. The culture was incubated at 30° C., 180 rpm for 14 days before use as inoculum for SSF.

An example of the SSF process is that which was used for the production of biomats in WO 2016/004380 and US 2016/0002680. Specifically, 100 grams of wheat straw was size reduced in a commercial blender and placed in a 2 liter glass bottle. 300 ml of Mandels and Reese medium and 3 ml of concentrated $H_2SO_4$ was added. The resulting slurry was autoclaved for 45 minutes at 121° C. The pH of the autoclaved slurry was adjusted with NaOH to 3.0, allowed to cool to room temperature, and then transferred equally between four 250 ml Erlenmeyer flasks. 10 ml of strain MK7 inoculum was added and the flasks shaken at 30° C., 180 rpm for 4 days followed by transfer of the contents of all flasks to a single 9×9 inch Pyrex® dish. The resulting culture was covered with Saran® wrap and incubated at 30° C. for 7 days before harvesting.

SSSF Procedure

Figure 14:
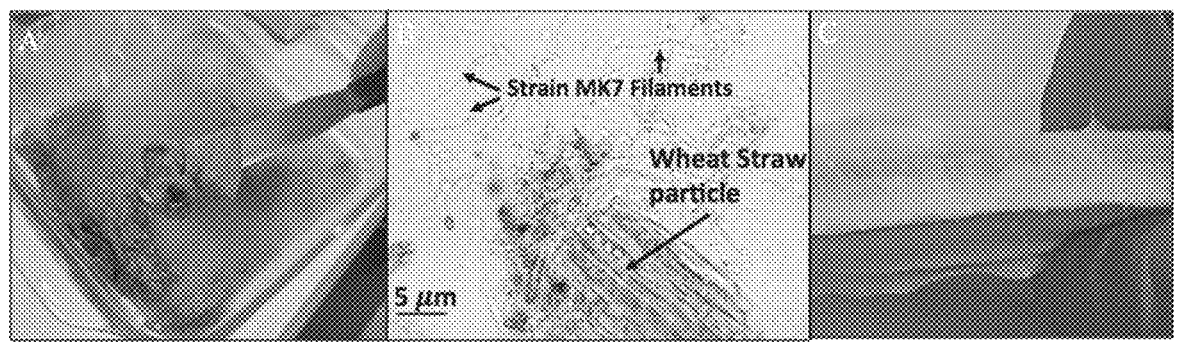
FIG. 14. A: Harvesting strain MK7 biomass cultivated via solid-state fermentation (SSF) showing strain MK7 completely integrated in lignocellulose at <5 g strain MK7 dry weight biomass/L (media: feedstock mixture). B: Midrograph image of harvested strain MK7 biomass of A showing filaments randomly integrated with wheat straw. C: strain MK7 biomat by solid substrate surface fermentation (SSSF) showing dense (180 g·L), cohesive essentially pure strain MK7 biomass.

The SSSF inoculum is described in Example 3 and procedures are described in Examples below (i.e. conversion of sugar beet pulp and other lignocellulosic materials that float on top of a liquid layer. Specifically, as referred to herein SSSF means fermentation that occurs when a solid substrate is submerged under the surface of a liquid, such that a filamentous fungi biomat grows on the surface of the liquid using carbon and nutrients derived from the submerged solid. Filamentous fungi biomats produced are cohesive, dense, and free of feedstock (FIG. 14C).

The biomass production and the resulting biomats produced differ considerably between the SSSF and SSF procedures. Medium components, ionic strength, osmotic pressure, feedstock concentration, inoculum quality, cultivation time (Tables 6 and 7) are all important parameter differences between SSSF and SSF methodologies. These process differences result in vastly different biomass properties (e.g. density, formation of a consolidated mat, microbial purity, filament length, filament organization, etc.).

Biomass produced by SSSF results in the production of filamentous fungi biomats that float on top of a liquid layer and that are physically separate from a solid feedstock layer. The resulting filamentous fungi biomat is an essentially pure fungal biomass organized into a cohesive and dense mat. The mat has a high tensile strength and is comprised of long filaments with average lengths spanning from millimeters to multiple centimeters (as shown in FIGS. 1C, 11 and 12). The filaments are predominantly organized parallel to the surface of the biomat and are connected by highly dense clumps of fungi. The surface of the biomat may or may not exhibit aerial hyphae that are oriented perpendicular to the surface of the biomat. The filamentous fungi biomat is easily removed from the growth environment as it is physically separate from the liquid or solid substrate, which enables rapid and easy harvesting of relatively pure filamentous fungi biomats.

In contrast, biomass grown by SSF produces biomass heterogeneously integrated with the solid substrate in a random configuration. The biomass filaments produced are generally less than 100 m in length (FIG. 14B). Further, the biomass produced by SSF is not cohesive and suffers from low tensile strength such that it cannot be picked up in a single unit (see FIG. 14A). The resulting biomass/solid substrate mixture tends to be of low density, particularly when compared to filamentous fungi biomats produced by SSSF.

TABLE 6

The following describes key differences in SSF and SSSF methodologies:

| | SSF | SSSF |
|---|---|---|
| Density (g dry weight strain MK7 biomass/kg of medium: substrate mixture | <5 | 120-180 |
| Tensile Strength | Not measurable | Wet biomass: 0.05-0.24 kg/com width, average~0.009 kg/com width. Dry biomass (no subsequent processing): 2-6 kg/com width, average ~3 kg/com width |
| Osmotic pressure of medium (atm) | 3.4 | 18.6 |
| Ionic strength of medium (molar) | 0.077 | 0.368 |
| Cell type used for inoculum | Stationary phase filamentous cells (i.e. cells > 100 μm in length) | Late exponential phase planktonic cells (i.e. cells < 20 μm in length) |
| Lignocellulose in medium (%) | >25 | 2.5-25 |
| Average filament length | 0.001-0.02 cm | 0.05-2 cm |
| Filament orientation | Random | Parallel |
| Final composition (%) | Less than 5% fungi | Greater than 95% fungi |
| Final biomat consistency | Fragile, not cohesive, heterogeneous | Robust, cohesive, homogeneous |

Example 19: SSF and SSSF of Sugar Beet Pulp by Strain MK7

Strain MK7 biomass was produced using SSF and SSSF methods with sugar beet pulp as the primary carbon source. Beet pulp is the vegetable portion of the sugar beet that remains after the sugar has been removed from the beet pulp at the processing plant. Sugar beet pulp was obtained from the Western Sugar Cooperative production plant in Billings, Mont., and was comprised of approximately 24% dry matter, 9.1% crude protein, 0.6% crude fat, 23.1% crude fiber, 4% ash, and 0.56% calcium.

For the SSF experiment, 50 g of dry beet pulp was mixed with 250 ml water. The mixture was autoclaved for 20 minutes to ensure sterility. After cooling to room temperature (~23° C.), the mixture was inoculated with 250 mg of moist strain MK7 biomat that was grown as a biomat on the surface of a corn stover/water mixture. The strain MK7 biomat was mixed into the beet pulp mixture with a sterilized spatula and the resulting inoculated mixture was allowed to incubate at room temperature for 4, 5, and 7 days.

For the SSSF experiments, beet pulp was added at a concentration of 7% to ½ strength MK7-1 medium (pulp weight:liquid volume) to create 300 ml of medium. The pH of the medium was adjusted to 4.8 by the addition of a suitable amount of HCl, followed by boiling for 20 minutes. After cooling to room temperature, approximately 100 mg of MK7 biomat that was grown as a filamentous fungi biomat on the surface of a corn stover/water mixture as described in Example C was mixed into the medium with a sterilized spatula. The pH was re-adjusted to 4.8 by the addition of a suitable amount of HCl and 100 ml aliquots of the inoculated pulp medium was then added to sterilized 0.023 $m^2$ Pyrex® glass trays prior to placing the trays in a tray rack system. The inoculated mixture was incubated at 23±1° C., resulting in flexible, dense biomats that were about 2.9, 3.4, and 4.1 mm thick after 4, 5, and 7 days, respectively. The biomats were harvested and dried at 50° C. for 48 h and the dry weights were 1.85 g (4 days), 2,25 g (5 days), and 2.85 g (7 days). The conversion of beet pulp to dry biomat was 26.4%, 32.1%, and 40.7% for the 4, 5, and 7 day mats, respectively. Biomat densities based on dry weight of the most biomat volume were 0.028, 0.029, and 0.030 $g/cm^3$ for the 4, 5, and 7 day mats, respectively.

Significantly different biomass forms resulted from growth using SSF versus SSSF. SSF produced biomass structures that were intimate mixtures of both biomass and substrate. These mixtures were comprised of low density fungal biomass intertwined around and within fragments of the beet pulp substrate. These intimate mixtures were primarily comprised of the substrate interspersed with a small amount of fungal biomass. Separation of the biomass from the substrate was not done as it would require significant additional process and would be technically difficult to accomplish.

In contrast, SSSF resulted in filamentous fungi biomats that were physically separate and distinct from the beet pulp substrate, allowing direct and straightforward harvesting of the biomat. Further, the resulting filamentous fungi biomats were dense, essentially pure and comprised of long aligned filaments.

Example 20: Growth of Strain MK7 Filamentous Fungi Biomats on Carrot and Broccoli Waste Dense strain MK7 biomats were produced in 6 days using homogenized broccoli or homogenized carrots as feedstocks. The broccoli and carrots were purchased from Costco Wholesale in Bozeman, Mont. 100 grams of each feedstock was individually homogenized in a commercial food processor using a metal blade at high speed for 5 minutes and placed in 2-liter beakers with 9000 ml of tap water. Medium salts were added as follows to form a mixture:

|  | g/L |
| --- | --- |
| $NH_4NO_3$ | 5.25 |
| Urea | 1.75 |
| $KH_2PO_4$ | 5.0 |
| $CaCl^2$ | 1.0 |
| $MgSO_4 \cdot 7\ H_2O$ | 1.0 |
| Micronutrients | mg/L |
| $FeSO_4 \cdot 7\ H_2O$ | 2.50 |
| $Zn\ SO_4 \cdot 7\ H_2O$ | 1.10 |
| $MnCl_2 \cdot 4\ H_2O$ | 0.25 |
| $CoCl_2 \cdot 6\ H_2O$ | 0.08 |
| $Cu\ SO_4 \cdot 5\ H_2O$ | 0.08 |
| $(NH_4)_6Mo_7O_{24} \cdot 4\ H_2O$ | 0.06 |
| $H_3BO_3$ | 0.06 |
| EDTA, free acid | 19.63 |

The pH of the mixture was adjusted to 3.5 by adding 1.3 ml concentrated HCl. The medium was covered with aluminum foil and then boiled for 30 minutes. After cooling to room temperature (~23° C.), 50 ml (7.5% volume:volume) of inoculum prepared as described in Example 3 was added to the medium for each feedstock and stirred until a homogenous mixture formed. 250 ml of mixture was poured into four separate 5×7 inch (0.02 $m^2$) trays and covered with Saran® wrap. The trays were cultivated for 7 days at 23°+1 C before harvesting. The resulting biomass was a flexible, dense filamentous fungi biomat free of the remaining broccoli or carrot feedstock. That is, a filamentous fungi biomat was produced that did not contain feedstock residue and was comprised of essentially pure MK7 biomass. The mean pH value of the residual liquid after harvesting was 6.2. The average thickness of the moist biomats was 3±1 mm. Filamentous fungi biomats were dried at 50° C. for 72 h and the average dry weights standard deviations were 1.7±0.2 g for broccoli and 1.7±0.2 g for carrots. The average conversion of broccoli to dry weight was 52±5 g strain MK7 dray weight/100 g dry weight broccoli. The average conversion of carrots to dry weight is 55±7 g strain MK7 dry weight/100 g dry weight carrots.

Example 21: Strain MK7 Cultivation on Municipal Organic Waste Surrogate (Grass Clippings and Leaves as a Function of Pretreatment)

The impact of acid and base pretreatments on municipal organic waste was evaluated as a function of the percentage conversion of feedstock to filamentous fungi biomat. Kentucky bluegrass clippings and ash tree leaves were separately dried at 60° C. until water content was less than 8%. Each feedstock was ground in a commercial blender into a fine powder.

HCl Acid Pretreatments 3 replicates of 10 g of grass/leaves (50:50 by dry weight) in 100 ml tap water at pH 2.5 (adjusted with 33% HCl) were pretreated by boiling 10 minutes.

3 replicates of 10 g of grass/leaves (50:50 by dry weight) in 100 ml tap water at pH 2.5 (adjusted with 33% HCl) with 10 mM $MnSO_4$ were pretreated by boiling 10 minutes.

3 replicates of 10 g of grass/leaves (50:50 by dry weight) in 100 ml MK7-1 medium at pH 2.5 (adjusted with 33% HCl) were pretreated by boiling 10 minutes.

3 replicates of 10 g of grass/leaves (50:50 by dry weight) in 100 ml MK7-1 medium at pH 2.5 (adjusted with 33% HCl) with 10 mM $MnSO_4$ were pretreated by boiling 10 minutes.

NaOH Base Pretreatments 3 replicates of 10 g of grass/leaves (50:50 by dry weight) in 100 ml tap water at pH 10.75 (adjusted with 1% NaOH) were pretreated by boiling 10 minutes. Final pH 2.5 was adjusted with HCl.

3 replicates of 10 g of grass/leaves (50:50 by dry weight) in 100 ml tap water at pH 10.75 (adjusted with 1% NaOH) with 10 mM $MnSO_4$ were pretreated by boiling 10 minutes. Final pH 2.5 was adjusted with HCl.

3 replicates of 10 g of grass/leaves (50:50 by dry weight) in 100 ml MK7-1 medium at pH 10.75 (adjusted with 1% NaOH) were pretreated by boiling 10 minutes. Final pH 2.5 was adjusted with HCl.

3 replicates of 10 g of grass/leaves (50:50 by dry weight) in 100 ml MK7-1 medium at pH 10.75 (adjusted with 1% NaOH) with 10 mM $MnSO_4$ were pretreated by boiling 10 minutes. Final pH 2.5 was adjusted with HCl.

Control Pretreatments 3 replicates of 10 g of grass/leaves (50:50 by dry weight) in 100 ml tap water. Final pH 5.5.

3 replicates of 10 g of grass/leaves (50:50 by dry weight) in 100 ml tap water, 10 mM $MnSO_4$. Final pH 5.5.

3 replicates of 10 g of grass/leaves (50:50 by dry weight) in 100 ml MK7-1 medium. Final pH 5.5.

3 replicates of 10 g of grass/leaves (50:50 by dry weight) in 100 ml MK7-1 medium, 10 mM $MnSO_4$. Final pH 5.5.

Figure 15:
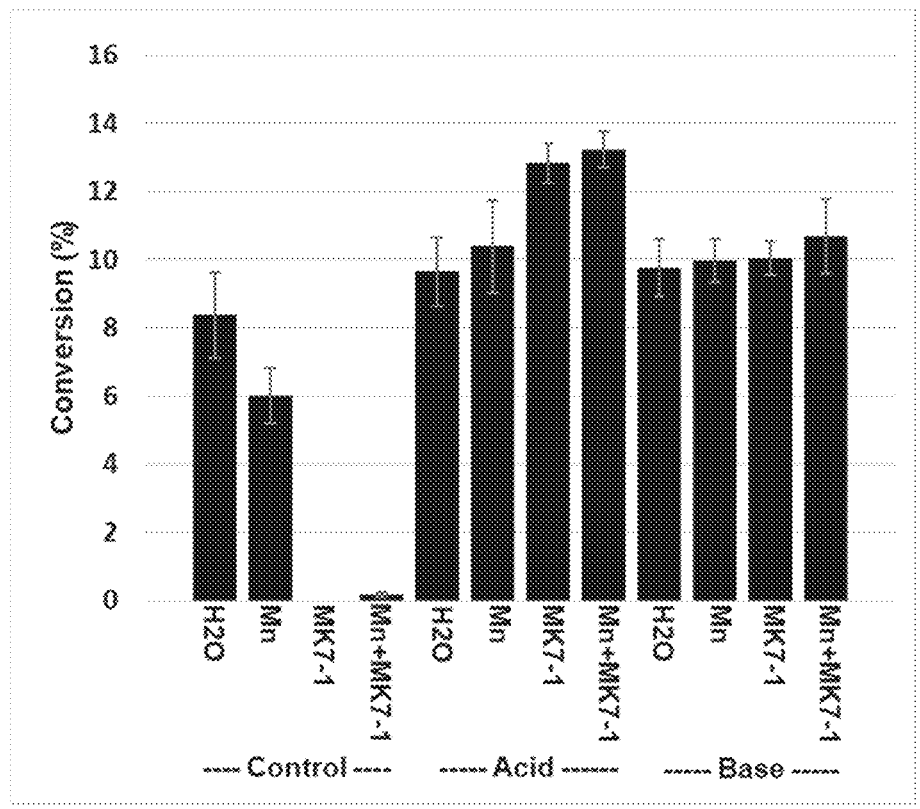
FIG. 15. Cultivation of strain MK7 with various treatments in 12.7×12.7 cm trays for 7 days. Error bars are standard deviations of three trays.

The samples were placed in 12.7×12.7 cm trays, covered, and then incubated for 7 days. Results are shown in FIG. 15. In each case, the application of a pretreatment increased the resulting conversion percentage. That is, a greater amount of conversion of the feedstock to resulting filamentous fungi biomat was achieved by the application of an acid or base pretreatment and by the addition of manganese.

Example 22: Growth of Strain MK7 Biomats on Starch

Dense strain MK& filamentous fungi biomats were produced in as little as 4 days using starch as a carbon and nutrient source (feedstock). The starch used in these specific experiments was 100% Argo Corn Starch manufactured by Argo Food Companies, Inc (Memphis, Tenn.) and purchased from Albertson's supermarket in Bozeman, MH.

Three batches of starch media were prepared by adding 6%, 8%, and 10% dry starch powder to 6 L volumes of drinking quality tap water in steel 10 L pots. This mixture was supplemented with MK7-1 salts and boiled for 10 minutes followed by cooling to room temperature (~23° C.). Heating the mixture resulted in coalesced clumps of starch that were then physically broken into smaller clumps. The pH of the mixture was adjusted to 2.7 and inoculated with 7.5% (volume:volume) of MK7 inoculum prepared as described in Example 3.

Aliquots of 1.5 L inoculated media were added to four sanitized polypropylene 0.25 m² trays, placed in a tray rack system, and incubated at 23°±1° C. Dense filamentous fungi biomats were observed after just 2 days of growth and the biomats harvested after 6 days. The mean pH value of the residual liquid remaining in the trays after harvesting was 6.05, 6.11, and 5.88 for the 6%, 8%, and 10% treatments, respectively. The mean thickness of the biomats were 2.9, 3.1, and 3.3 mm for the three treatments, respectively. Filamentous fungi biomats were dried at 50° C. for 72 h and the average dry weights±standard deviations were 29.0±1.3, 34.4±1.5, and 38.2 =1.9 g for the four replicate trays containing the 6%, 8%, and 10% starch, respectively. This is equivalent to a conversion percentage of 32, 29, and 25% starch to filamentous fungi biomats dry weight. Average densities on a dry weight basis for the moist filamentous fungi biomats were 0.04, 0.04, and 0.05 g/cm² for the three treatments, respectively.

Example 23: Growth of Strain MK7 Filamentous Fungi Biomats on Potato Processing Waste Streams Dense strain MK7 filamentous fungi biomats were produced in 7 days using potato processing waste as carbon and nutrient source (feedstock). Potato processing waste is commonly produced during the processing of potatoes and includes waste streams from washing, peeling, and cutting operations (i.e. French fries, potato cubes, flakes, and the like). Potato processing waste streams also include discharge piles comprised of multiple potato processing waste streams pilin in a heap and exposed to the natural environment with no coverings. In this example, potato processing waste stream comprised of processing waste of multiple varieties of potatoes was obtained from Bauch Farms in Whitehall, Mont. on Sep. 21, 2016, and used within 48 hours as a carbon and nutrient source to grow strain MK7 biomats.

Potato shorts are those pieces of potato that remain after French fries are cut from a full potato. Potato shorts vary in size and dimensions spanning, as a non-limiting example, from thin slivers to pieces that are 6 inches long by 0.5 inches thick or more. Fresh discards, in the majority of cases, describes those pieces of potato that are removed from a potato due to damage, bruising, or the like. In some cases, whole potatoes are included as discard samples. Peels are predominantly skins removed from potatoes.

Potato shorts, discards and skins were processed by a food processor to a homogenous consistency (Farbarware Model 103742 food processor set on high) in approximately 500 ml volume batches for 1 minute. Food processed samples are termed blendate for the purposes of description in this example.

Blended potato shorts and fresh discards were added to two 15 L epoxy-coated steel cooking pots at a ratio of 10% wet weight blendate to a volume of MK7-1 medium at a ratio of 500 g blendate to 4.5 L liquid MK7-1 medium, producing a mixture. The pH of the mixture was adjusted to 2.45 with concentrated HCl. Strain MK7 inoculum, prepared as described in Example 3, was added at a ratio of 7.5% volume:volume (i.e. 375 ml inoculum to 4625 ml mixture. Aliquots of 1.5 L inoculated suspension were added to individual 0.25 m² sterilized polypropylene trays in triplicate and placed in a tray rack system. The cultures were incubated at 23°±1° C., resulting n flexible, dense biomats harvested after 7 days. The mean pH value of the residual liquid remaining in the trays after harvest was 7.1 for the shorts and 6.9 for fresh discards treatments. Harvested biomats were rinsed in 7 L tap water with gentle agitation for 10 minutes and dried at 50° C. for 72 h.

The average thickness of the moist biomats was 3.8±0.9 mm for the shorts and 3.9±1.0 mm for the discards. The average dry weights±standard deviations of the biomass in each tray were 33.6±0.6 g from the shorts and 40.2±2.7 g for the fresh discards. The average density of the biomats based on dry weight was 0.035 g/cm$^3$ for the shorts and 0.041 g/cm$^3$ for the discards. The average conversion of total solids in the original potato by-products to dry biomat was 36% for the shorts and 43% for the fresh discards. Near 50% conversion would be considered 100% conversion efficiency of the carbon given the fact that about 50% of the carbon used by strain MK7 is released to the atmosphere as carbon dioxide.

Blended potato peels were pretreated prior to growth experiments to increase access of potato peel nutrients to strain MK7. Blended potato peels (175 g) were added to each of nine 12.7×17.8 cm (0.023 cm$^2$) Pyrex® glass trays to create an experimental matrix of three treatments with three replicates each. Treatment 1 received 50 ml drinking quality tap water. Treatment 2 received a 45 ml aliquot of strain MK7 hydrolysate containing a suite of strain MK7 hydrolytic enzymes excreted by strain MK7 when grown on corn stover. Treatment 3 received 50 ml tap water and a suite of commercial enzymes comprised of 0.05 g cellulase Y—C (MP Biomedicals, Cat #320951, Lot #M4156), 2.5 ml glucoamylase (Distillate VHP, Dupont), 2.5 ml alpha-amylase (APEZYME ALPHA, 13,775 AAU/g, Dupont) and 2.5 ml beta-gluconase (Optimash TBG, Dupont). Treatment 3 trays were incubated at 50° C. for 30 minutes to stimulate enzymatic hydrolysis followed by boiling for 5 minutes to inactivate the enzymes. The pH of the treatments was adjusted to 3.0 using concentrated HCl and all trays were inoculated with 10 ml of strain MK7 prepared as described in Example 2. After 7 days, the biomats were removed from the surface of the liquid, rinsed in tap water for 10 seconds and dried at 60° C. for 48 h. Conversion of potato peel dry weight to dry biomats were: Control (H2O only) mean=5.9% (5.5%, 6.5%, and 5.8%); Strain MK7 enzymes=9.0% (7.2%, 10.1%, and 9.8%); and Commercial enzymes=9.9% (10.2%, 8.4%, and 11%).

Example 24: Nutritional Analysis Biomass Produced by SSF Versus Biomats Produced by SSSF Nutritional analysis was performed by Eurofins comparing the biomats resulting from SSF versus SSSF methodologies. SSF samples were obtained from strain MK7 cultivated on corn stover pretreated with ammonia fiber expansion (AFEX) by Michigan Biotechnology Institute. 150 g of AFEX were added to 500 ml of tap water and autoclaved at 121° C. after adjusting the pH to 3.5 with concentrated HCL. Resulting mixture was inoculated with 25 ml of strain MK7 inoculum according to Example 18. Slurry was transferred to a 23×23 cm Pyrex® glass tray and incubated at room temperature for 11 days. Integrated strain MK7 biomass and corn stover was harvested and dried at 60° C. for 48 hours. Samples were analyzed for total protein, total fiber, total carbohydrates, ash, and total fats by Eurofins USA (Des Moines, Iowa).

SSSF samples were obtained from mats produced on 5% AFEX corn stover. 50 g of AFEX corn stover was added to 1 L of tap water and autoclaved at 121° C. after adjusting the pH to 3.5 with concentrated HCl. The resulting mixture was inoculated with 50 ml of strain MK7 inoculum prepared as described in Example 3. Slurry was transferred to two 23×23 cm Pyrex® glass tray and incubated at room temperature for 11 days. Mats were harvested and rinsed in tap water for 30 seconds followed by drying at 60° C. for 24 hours. Samples were analyzed for total protein, total fiber, total carbohydrates, ash and total fats by Eurofins USA (Des Moines Iowa).

TABLE 7

| Eurofins Analysis | SSF (%) | SSSF (%) |
|---|---|---|
| Total protein | 2.56 | 51.10 |
| Total fat | 0.60 | 12.00 |
| Total fiber | 80.30 | 23.30 |
| Total sugars | 2.10 | <0.35 |
| Total ash | 15 | 12.40 |

Example 25: Amino Acid Profile of the Filamentous Acidophilic MK7 Fungal Strain The filamentous acidophilic MK7 fungal strain biomat was produced in tray reactors using the method described in Examples 2 and 3 in the MK7-1 medium. The filamentous biomass from 6 trays was combined prior to drying at 60° C. for 45 minutes and 50° C. for 72 hours. 400 g of this filamentous biomass was sent to Eurofins Scientific Inc. Nutritional Analysis Center in Des Moines, Iowa, for nutritional analysis. Amino acids were analyzed using the internationally recognized methods published in the Association of Official Agricultural Chemists (AOAC) Official Methods of Analysis as follows: AOAC 988.15 for Tryptophan, AOAC 994.12 mod. for Cystine and Methionine, AOAC 982.30 mod. for Alanine, Arginine, Aspartic Acid, Glutamic Acid, Glycine, Histidine, Isoleucine, Leucine, Phenylalanine, Proline, Serine, Threonine, Total Lysine, Tyrosine and Valine. The amino acid composition of the filamentous acidophilic MK7 fungal strain sample reported by Eurofins is compared with the amino acid composition of *Fusarium venenatum* used for fish food (Alriksson, B. et al. (2014) Fish feed from wood. *Cellulose Chemistry and Technology* 48:9-10 (2014), Quorn (Nutritional Profile of Quorn Mycoprotein, 2009), egg albumin (Food and Agriculture Organization of the United Nations. The Amino Acid Content of Foods and Biological Data on Proteins, Nutritional Study #24. Rome (1970). UNIPUB, Inc., 4611-F Assembly Drive, Lanham, MD 20706) and *Rhizopus oligosporus* (Graham, D. C., Steinkraus, K. H. & Hackler, L. R. (1976) Factors affecting production of mold mycelium and protein in synthetic media. *Appl Environ Microbiol* 32:381-387) in Table 8. The total protein content was measured as 41.5% of a 4.5% moisture content biomass. Notably, the filamentous acidophilic MK7 fungal strain was shown to have a higher concentration of essential amino acids compared to all of the four other protein sources, making the filamentous acidophilic MK7 fungal strain a highly desirable source of protein for food and feeds.

TABLE 8

Amino acid concentration as a percent of total amino acids are provided for the filamentous acidophilic MK7 fungal strain and four high protein food/feed sources. Essential amino acids are denoted with an asterisk.

|  | Strain MK7 | Fusarium venenatum for fish food | Quorn | Egg albumin | Rhizopus oligosporus (Tempeh) |
|---|---|---|---|---|---|
| *Tryptophan | 1.48% | 0.94% | 1.24% | 1.18% | 0.75% |
| Cystine | 1.04% |  |  | 1.88% |  |
| *Methionine | 1.65% | 1.51% | 1.59% | 3.01% | 0.58% |
| Alanine | 16.38% |  |  | 5.49% |  |
| Arginine | 5.39% | 4.72% |  | 4.54% |  |
| Aspartic | 9.17% |  |  | 6.09% |  |
| Glutamic | 10.72% |  |  | 10.89% |  |
| Glycine | 5.06% |  |  | 2.89% |  |
| *Histidine | 2.12% |  | 2.69% | 1.67% |  |
| *Isoleucine | 4.48% | 3.96% | 3.93% | 5.00% |  |
| *Leucine | 6.84% | 5.85% | 6.55% | 6.80% |  |
| *Phenylalanine | 3.57% |  | 3.72% | 4.94% |  |
| Proline | 4.35% |  |  | 2.92% |  |
| Serine | 4.45% |  |  | 6.07% |  |
| *Threonine | 5.49% | 3.77% | 4.21% | 3.41% | 3.05% |
| *Lysine | 7.25% | 5.66% | 6.28% | 4.64% | 4.28% |
| Tyrosine | 2.70% |  |  | 3.21% |  |
| *Valine | 7.85% | 4.72% | 4.14% | 6.02% |  |

Example 26: Production of C18-Rich Lipids by the Filamentous Acidophilic MK7 Fungal Strain from Food Grade Glycerol Medium Preparation: 4.5 liters of MK7-1 medium was prepared with 125 g/L glycerol (The Chemistry Store—Kosher Food Grade Glycerol>99.7%, ASIN: B00KN1LRWQ, available on the internet) (562.5 grams) with NH$_4$NO$_3$ and Urea nitrogen concentrations altered to a C:N ratio of 40:1 (mols carbon in C source:mols N in nitrogen compounds).

TABLE 9

Composition of MK7-1 medium modified to provide a C:N ratio of 40:1 and 12.5% glycerol concentration. Micronutrients were supplied by adding 2 mL/L of a 500x stock solution described in Table 1 (Example 1).

| Total Volume | 4.5 |
|---|---|
| NH$_4$NO$_3$ (g) | 10.8 |
| Urea (g) | 3.7 |
| CaCl$_2$ (g) | 9.0 |
| MgSO$_4$—7H$_2$O (g) | 9.0 |
| KH$_2$PO$_4$ (g) | 45.0 |
| Micronutrients (mL) | 9.0 |
| Glycerol (g) | 563 |
| Glycerol (L) | 0.446 |
| C:N ratio | 40:1 |
| pH | 2.7 |
| Deionized H2O (L) | 4.05 |
| HCl (mL) | 5.85 |

The mixture pH was adjusted to 2.7 and heat sterilized by boiling for 30 minutes in a 2 liter Erlenmeyer flask with top of flask covered with aluminum foil. The mixture was cooled for 2 hours to 25° C.

Inoculation: Inoculum (15 g/L planktonic cells as dry weight in exponential growth phase (see Example 3) was added to the cooled flask at a final dry weigh concentration of 1 g/L. The flask was thoroughly mixed for even distribution of inoculum. Planktonic state cells are critical for mat formation and it is desired that cell clustering (i.e. biofilm greater than 1 mm) be minimized. Ideally, cell clusters greater than 2.5 mm should be filtered from the inoculant prior to distribution.

Incubation and harvesting: The mixture with inoculum was evenly distributed in three 0.25 m$^2$ trays at a volume of 1.5 liters/tray or 6 liters per square meter and incubated at 25 C, 90-100% humidity for 8 days. A consolidated biomat biomass is produced at cell densities above 30 g/L and biomass is able to be harvested as one cohesive mat. In one embodiment the mat is simply rolled off the tray (FIG. 6). The mat is rinsed for 30 seconds using running water and allowed to drip dry for 5-10 minutes. Squeezing of the mat was avoided as protein and other fungal nutrients are lost through excessive water removal. The filamentous biomass after drip drying had a wet weight of 410 grams (or 1,620 grams/m$^2$). Moisture content was measured at 82% (i.e. dry weight of 18%) corresponding to dry weight of 73.8 g/tray or 295 g/m$^2$. Dry weight filamentous biomass of 18% compares favorably to processing of other fungal biomass grown in submerged cultures with typical dry weight of 1.5%. In contrast, state of the art processes utilize centrifuges (an energy and capital intensive process) to achieve desired fungal biomass density. The process described herein requires far less processing, equipment and energy input compared to these more expensive methods.

Figure 16:
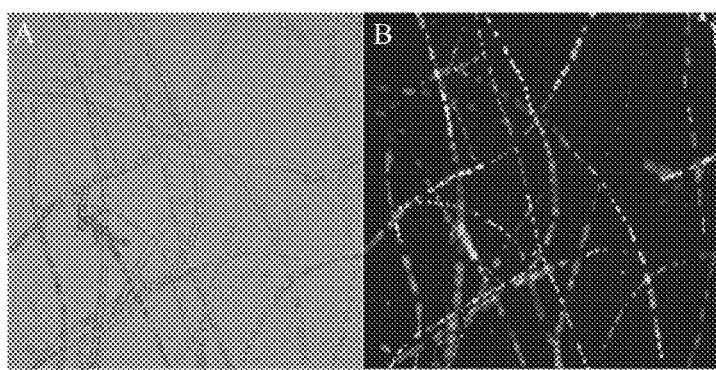
FIG. 16. Left: optical microscopic image of strain MK7 cultured with 12.5% glycerol at pH 2.7 after 8 days. Right: fluorescent image after Nile Red staining indicating a high percentage of lipid estimated at between 40-60% of cell area.

Lipid analyses: Estimates of total lipids were done by the UV-Vis microscopy with Nile Red staining (Cooksey et al., 1987; FIG. 16), which estimated total lipids at 40-50%. Quantification of total intracellular lipids was determined using direct transesterification coupled with GC-MS analysis as described in Lohman et al. (2013) and was found to be 39%. This corresponds to lipid production of 115 g lipid/m$^2$ in 8 days (14 g/m$^2$/day) or 0.39 g/liter/hour average production rate. These rates are much faster than those found in submerged cultures with the filamentous acidophilic MK7 fungal strain with 8% glycerol (0.245 g/L/hr) and very competitive to other organisms found in the literature including yeast and algae. Furthermore, the filamentous acidophilic MK7 fungal strain produces lipids at these competitive rates at very high glycerol concentrations not tolerable by most organisms and is the only organism (to our knowledge) that can do this at acidic pH ranges, which has significant advantages for limiting contamination. Furthermore, the lipid coefficient (g lipid/g substrate) is highly competitive to other strains at 0.21 g lipid/g glycerol (see attached table). Increased lipid production rates and cell densities of 180 g/L have direct implications to transform the production of microbial oils by a wide variety of microorganism currently being developed or in commercial use.

Figure 17:
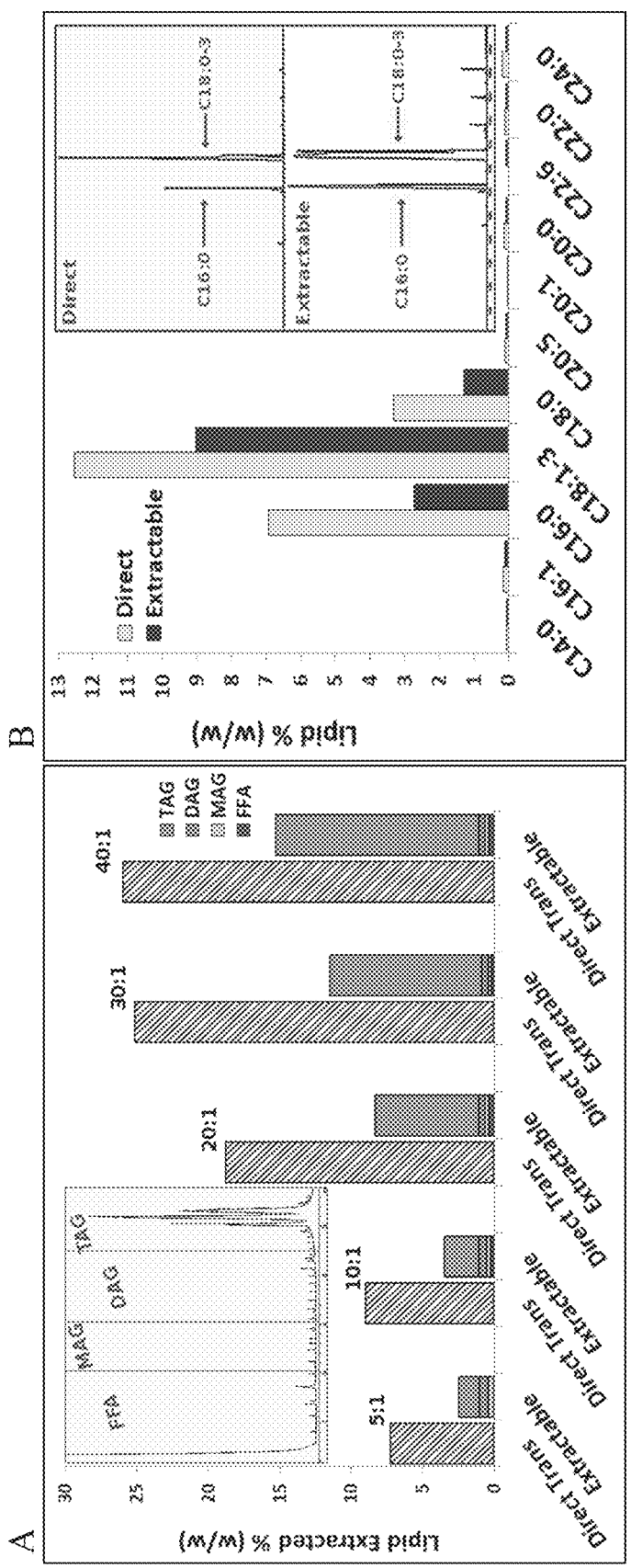
FIG. 17. Lipid profiles produced by strain MK7. (Left Panel) Average of total fatty acid methyl esters (FAME) in direct transesterification (total fuel potential) and extractable lipid fractions as a function of media C:N ratio (n=3). Bars within the extractable lipid fraction bar represent tri-, di- and mono-acyl glycerides (TAG, DAG, MAG) and free fatty acids (FFA) components. Inset shows a GC-FID chromatogram with TAG molecules dominating the lipid fraction. (Right Panel) FAME profile of lipids generated from direct transesterification of all fatty acids (Direct) to FAME, and FAME derived from only extractable lipid precursors (Extractable). Inset shows GC-MS chromatograms for the Direct and Extractable fractions.

The filamentous acidophilic MIK7 fungal strain lipid profiles are remarkably consistent among different types of treatments (i.e. pH, temperature, growth substrate, cultivation duration, moisture content) and are dominated by C16:0 and C18:0, C18:1 and C18:2 triacylglycerides (>95% of total lipids; Table 10 below; FIG. 17). Fatty acid profiles also show a number of high value products including the omega-7 vaccenic acid (Methyl 11-octadecenoate), omega-7 palmitoleic acid (methyl hexadec-9-enoate; trade name Provinal™) and tetracosanoic acid, methyl ester. These are rare fatty acids not typically found in vegetable oils and may produce significantly more revenue per ton of feedstock than biodiesel alone.

TABLE 10

Identities, concentrations of fatty acids found in strain MK7 biomass cultivated with 12.5% glycerol for 8 days 30° C.; and C:N ratio of 40:1

|  | EuroFin % of FAME Profile | SB (n = 3) | |
|---|---|---|---|
|  |  | % of FAME Profile | STD |
| C10:0 (Capric acid) | 0.3% | 0.1% | 0.01% |
| C11:0 (Undecanoic acid) | 0.3% | 0.0% | 0.01% |
| C12:0 (Lauric Acid) | 0.3% | 0.0% | 0.00% |
| C14:0 (Myristic acid) | 0.5% | 0.4% | 0.00% |
| C14:1 (Myristoleic acid) | 0.3% | 0.0% | 0.00% |
| C15:0 (Pentadecanoic acid) | 0.3% | 0.3% | 0.03% |
| C16:0 (Palmitic Acid) | 15.8% | 21.2% | 0.45% |
| C16:1 Omega 7 | 1.0% | 0.8% | 0.05% |
| C17:0 (Margaric Acid) | 0.3% | 0.1% | 0.00% |
| C18:0 (Stearic Acid) | 4.8% | 14.7% | 0.39% |
| C18:1 (Oleic Acid/Isomers) | 23.0% | 31.9% | 0.14% |
| C18:2 Omega 6 (Linoleic Acid) | 42.8% | 26.8% | 0.60% |
| C18:2 (Isomers) | 1.0% | 0.2% | 0.00% |
| C18:3 (Linolenic Acid/Isomers) | 2.3% | 0.9% | 0.07% |
| C20:0 (Arachidic Acid) | 0.3% | 0.7% | 0.02% |
| C20:1 (Gadoleic Acid/Isomers) | 0.3% | 0.1% | 0.01% |
| C21:5 Omega 3 (Heneicosapentaenoic Acid) | 0.3% | 0.0% | 0.01% |
| C22:0 (Behenic Acid) | 0.3% | 0.5% | 0.03% |
| C22:1 (Erucic Acid/Isomers) | 0.3% | 0.0% | 0.00% |
| C24:0 (Lignoceric Acid) | 0.7% | 0.7% | 0.00% |
| C24:1 (Nervonic Acid/Isomers) | 0.3% | 0.0% | 0.00% |
| Total %: | 94.7% | 99.4% |  |

Example 27: Toxicity Analyses of Strain MK7

Five samples of strain MK7 grown under different conditions were assayed for the presence of mycotoxins. Sample 1 biomass was produced in a 10 L bioreactor under the same conditions used to generate inoculum as described in Example 1, with exception that the C:N ratio was 30:1. The biomass sample was collected by filtering through a 0.2 um filter using a vacuum filtration apparatus as described in Example 1.

Sample 2 biomat was produced in a sterilized 12.7×17.8 cm (0.02 $m^2$) Pyrex® glass tray using 50 mL of pH 2.8 MK7-1 medium prepared as described in Example 1, with exception that the media was supplemented with 12% glycerol and 0.2% peptone (weight/volume; Peptone granulated, Fisher Scientific, Lot #143241, Somerville, N.J.). Sample 2 used the same procedure for sterilization as used for 0.25 $m^2$ trays related in Example 3.

Sample 3 was grown in conditions identical to Sample 2, with exception that the pH was adjusted to 4.5 and the media was not supplemented with peptone.

Sample 4 was grown in conditions identical to Sample 2, with exception that the medium was supplemented with 4% glycerol.

Sample 5 was grown in conditions identical to Sample 2, with exception that the pH was adjusted to pH 2.2 and the media was not supplement with peptone. Samples 2 through 5 media were inoculated with 7.5% (vol/vol) of the liquid culture used for Sample 1. Wet biomass samples were collected after 8 days of growth and stored at −20 C prior to extraction of mycotoxins.

Mycotoxins were extracted from wet biomass using a Myco6in1+mycotoxin assay kit supplied by Vicam (Lot #100000176: Nixa, MO) following the standard protocol described in the Myco6in1+assay kit manual. Twelve different mycotoxins were analyzed by LC-Q-TOF using the protocol described in the Myco6in1+LC/MS/MS Instruction Manual. An Agilent 6538 Q-TOF coupled to an Agilent 1290 IPLC housed at the Mass Spectrometer Core Facility at Montana State University was used for identification and quantification of the toxins. Fumonisin B1 and Fumonisin B2 were used as authentic standards.

Measured values for all toxins tested were below the regulatory levels for human consumption set by the U.S. Food and Drug Administration (Table 11). Measured levels were at least one order of magnitude lower than regulatory levels, with exception to Total Aflatoxins found in Sample 4, which were 8.76 ng/g compared to the regulatory level of 20 ng/g. However, the genes for aflatoxin production are not present in strain MK7, therefor it is expected that the source of this toxin was contamination from peptone and other ingredients used in the medium and not a product of MK7.

TABLE 11

Quantification of mycotoxins in biomass of strain MK7.

|  | Sample # | | | | | Regulatory Limit |
|---|---|---|---|---|---|---|
|  | 1 | 2 | 3 | 4 | 5 | ng/g |
|  | Quantitation (ng/g) (wet weight) | | | | | |
| Aflatoxin B1 | 0.03 | 0.04 | 0.02 | 0.49 | 0.02 | 20 * |
| Aflatoxin B2 | 0.33 | 3.13 | 0.12 | 0.80 | 0.10 | 20 * |
| Aflatoxin G1 | 0.02 | 0.02 | 0.04 | 1.91 | 0.04 | 20 * |
| Aflatoxin G2 | 0.20 | 0.03 | 0.56 | 5.56 | 0.49 | 20 * |
| Ochratoxin A | 0.01 | 0.00 | 0.00 | 0.00 | 0.00 | Not Established |
| Deoxynivalenol | 0.24 | 0.10 | 0.02 | 0.13 | 0.02 | 1,000 |
| Fumonisin B1 | 0.00 | 0.91 | 0.00 | 4.41 | 0.00 | 2,000 ⱡ |
| Fumonisin B2 | 0.00 | 17.40 | 0.04 | 89.58 | 0.02 | 2,000 ⱡ |
| Nivalenol | 0.12 | 0.08 | 0.04 | 0.37 | 0.04 | Not Established |
| T-2 toxin | 0.07 | 0.00 | 0.02 | 0.00 | 0.03 | Not Established |
| HT-2 Toxin | 0.13 | 0.11 | 0.04 | 0.14 | 0.05 | Not Established |
| Zearalenone | 0.00 | 0.00 | 0.04 | 0.37 | 0.04 | Not Established |

\* Total Aflatoxins
ⱡ Total Fumonisins

The non-toxic character of MK7 culture medium and biomass was further verified by bioassays with *Daphnia magna*, a highly sensitive macroinvertebrate commonly used for toxicity assays (EPA Publication, 1987; Guilhermino et al., 2000). Live *D. magna* was purchased from Carolina Biological Supply (Burlington, N.C.) and grown under the conditions described in the manual provided by the supplier. After 24 hours of growth and observation, the *Daphnia* were used for the toxicity experiment. Three Petri dishes were filled with 30 mL of a 30% of MK7 culture (MK7 and MK7-1 medium) grown in the inoculum reactor for 6 days as described in Example 3, and 70% water in which the *D. magna* were shipped. For an experimental control, three additional Petri dishes were filled with 30 mL of shipping water. Seven *D. magna* that appeared lively were added to each of the six Petri dishes and observed daily for three days. Death of the *D. magna* was defined as no visible movement after 1 minute. No significant differences in survival rates were observed between *D. magna* treated with MK7 culture medium and biomass, and the experimental controls over 3 days (average 1.2 deaths per Petri dish after 3 days for each treatment).

The toxicity of strain MK7 biomass was also tested on Goldfish (*Carassius auratus*). Two identical 5.7 L fish tank, pump and filters were purchased from Petco in Bozeman, Mont. (Aqueon model #E414W, Franklin, Wis.). The tanks were filled with 5.7 L of Poland Spring water purchased from the Albertson's supermarket, Bozeman Mont. Six goldfish (~3 cm in length) were purchased from Petco (Bozeman, Mont.) and three were placed in each one of the tanks. One of the tanks received about 0.05 g of dry TetraFin Goldfish Flakes Plus (Blacksberg, Va.) fishfeed daily (purchased from Petco, Bozeman, Mont.). The other tank received about 0.0.05 g of dried strain MK7 biomass daily. The wet MK7 biomass was obtained from one of the tray reactors produced according to the protocol described in Example 3. MK7 biomass was prepared by removing 40 g of MK7 from a tray (see Example 3) and placing the biomass in a 250 mL beaker. The wet biomass was then microwaved using a GE microwave (Model WES1452SS1SS) for 30 seconds. The dried biomass had a moisture content of less than 0.5%. The biomass was then crushed with a stainless steel spatula to from small flakes that were similar in size to the TetraFin Goldfish Flakes. All fish survived and appeared to be healthy (vigorously swimming) after 60 days of feeding and showed marked enthusiasm for eating the MK7 produced biomass matt. The experiment was terminated after 60 days.

```
18S rRNA and ITS region DNA sequence of the
acidophilic filamentous fungal species
designated as strain MK7
                                      SEQ ID NO: 1
[263] CCGCGGGGAATACTACCTGATCCGAGGTCACATTCAGAGTTG

GGGGTTTACGGCTTGGCCGCGCCGCGTACCAGTTGCGAGGGTTTTACT

ACTACGCAATGGAAGCTGCAGCGAGACCGCCACTAGATTTCGGGGCCG

GCTTGCCGCAAGGGCTCGCCGATCCCCAACACCAAACCCGGGGGCTTG

AGGGTTGAAATGACGCTCGAACAGGCATGCCCGCCAGAATACTGGCGG

GCGCAATGTGCGTTCAAAGATTCGATGATTCACTGAATTCTGCAATTC

ACATTACTTATCGCATTTTGCTGCGTTCTTCATCGATGCCAGAACCAA

GAGATCCGTTGTTGAAAGTTTTGATTTATTTATGGTTTTACTCAGAAG

TTACATATAGAAACAGAGTTTAGGGGTCCTCTGGCGGGCCGTCCCGTT

TTACCGGGAGCGGGCTGATCCGCCGAGGCAACAATTGGTATGTTCACA

GGGGTTTGGGAGTTGTAAACTCGGTAATGATCCCTCCGCAGTTCTCAC

CTACGGATAGGATCATTACCGAGTTTACAACTCCCAAACCCCTGTGAA

CATACCCATTGTTGCCTCGGCCGGATCAGCCCGCTCCCGGTTAAAACG

GGACGGCCCGCCAGAGTACCCCTAAACTCTGTTTCTATATGTAACTTC
```

```
TGAGTAAAACCATAAATAAATCAAAACTTTCAACACGCATCTCTTGCT

TCTGTCATCGATGAAGAACGCAGCAAAATGCGATAGTCATGTGATTGC

ACATTCAGTGAATCATCGATCTTGACGCACATTGCGCCTGCAGTATTC

TGGCGGTCATGCCTGTTCGAGCGTCATTCAGCCCTCAGCCCTCGGTTG

TGTTCGGGATCGGCGAGTCCTGCGCCAGCGACCGGATCAGTGGCGTCT

GCCTGCGCCTCCATTGCGGTTAGAGTTAAGCCCTCGCCCACTTGTTTT

ACGCTAAC

Translation elongation factor 1 alpha (Tef1)
                                      SEQ ID NO: 2
[264] ATGATCACTGGTACTTCCCAGGCCGATTGCGCCATTCTCATC

ATTGCCGCCGGTACTGGTGAGTTCGAGGCTGGTATCTCCAAGGATGGC

CAGACCCGTGAGCACGCTCTTCTTGCCTACACCCTTGGTGTCAAGAAC

CTCATCGTCGCCATCAACAAGATGGACACCACCAAGTGGTCTGAGGCC

CGTTACCAGGAGATCATCAAGGAGACCTCCTCCTTCATCAAGAAGGTC

GGCTACAACCCCAAGGCTGTCGCTTTCGTCCCCATCTCCGGTTTCAAC

GGTGACAACATGCTTACCCCCTCCACCAACTGCCCCTGGTACAAGGGT

TGGGAGCGTGAGATCAAGTCCGGCAAGCTCACCGGCAAGACCCTCCTC

GAGGCCATTGACTCCATCGAGCCTCCCAAGCGTCCCGTTGACAAGCCC

CTCCGTCTTCCCCTCCAGGATGTCTACAAGATCGGTGGTATTGGAACG

GTTCCCGTCGGCCGTATTGAGACTGGTGTCATCAAGCCCGGTATGGTC

GTTACCTTCGCTCCCTCCAACGTCACCACTGAAGTCAAGTCCGTCGAG

ATGCACCACGAGCAGCTCAGTGAGGGCCAGCCCGGTGACAACGTTGGT

TTCAACGTGAAGAACGTCTCCGTCAAGGACATCCGACGTGGTAACGTC

GCTGGTGACTCCAAGAACGACCCCCCCCAGGGTGCCGCTTCTTTCACC

GCCCAGGTCATCGTCCTCAACCACCCCGGCCAGGTCGGTGCTGGTTAC

GCTCCCGTCCTCGATTGCCACACTGCCCACATTGCCTGCAAGTTCGCC

GAGATCCAGGAGAAGATCGACCGCCGAACCGGTAAGGCTACTGAGGCC

GCTCCCAAGTTCATCAAGTCTGGTGACTCCGCCATCGTCAAGATGGTT

CCCTCCAAGCCCATGTGTGTCGAGGCTTTCACTGACTACCCTCCTCTG

GGTCGTTTCGCCGTCCGTGACATGCGACAGACTGTCGCCGTCGGTGTC

ATCAAGGCCGTCGAGAAGTCCACCGGTGCTGCTGGCAAGGTCACCAAG

TCCGCTGCCAAGGCCGCCAAGAAATAA

Tubulin beta chain (Tub1): partial sequence
                                      SEQ ID NO: 3
[265] GTGGATCTTGAGCCCGGTCCTCAGGATGCCATCCGCGCCGGG

CCCCTAGGCCAGCTTTTCCGCCCCGACAACTTCGTCGCCGGAAATGCC

AGCGCCGGTAACAACTGGGCCAAGGGTCATTACACCGAAGGTGCTGAG

CTCGTTGAGGAGGCCATCGATGTTGTGCGACACGAGGTTGAGAACTGT

GACCATCTTCAGGGTTTCCAGCTCACCCACTCTCTCGGCGGTGGTACC

GGTTCTGGTATGGGAACGCTTCTTCTGTCGAAAATCCGTGAGGAGTTT

CCCGATCGCATGATGGCTACTTTTTCCGTTATGCCTTCGCCTAAGGTT

TCTGATACCGTTGTCGAACCTTACAACGCCACTTTGTCATTGAACCAG
```

```
-continued
CTTGTCGAGAACTCCGATGAGACCTTCTGTATCGATAACGAGGCTTTG

TACGACATTTACGAGAAGACCCTGAAGATTGCTGATCCTTCTTACGCC

GATCTC
```

REFERENCES

Abe T., Hoshino T., Nakamura A., and N. Takaya. 2007. Anaerobic elemental sulfur reduction by fungus *Fusarium oxysporum*. Biosci Biotechnol Biochem. 71:2402-7.

Bligh, E. G. and Dyer, W. J. 1959. A rapid method for total lipid extraction and purification. *Can. J. Biochem. Physiol.* 37:911-917.

Bhatia, LS, Arneja J. S. Lipid metabolism in *Fusarium oxysporum*, Journal of the Science of Food and Agriculture, 2006, 29(7):619-626.

Boominathan, K., Reddy, C. A. 1992. cAMP-mediated di-erential regulation oflignin peroxidase and manganese-dependent peroxi-dase production in the white-rot basidiomycete *Phanerochaete chrysosporium*. Proc. Natl. Acad. Sci. 89:5586-5590.

Briggs, Michael. UNH Biodiesel Group. 2004. "Wide scale Biodiesel Production from Algae". http://www.unh.edu/p2/biodiesel/article_alge.html.

Brimble M. A., Letecia J. Duncalfband Michael R. Nairn. 1999. Pyranonaphthoquinone antibiotics-isolation, structure and biological activity. Nat. Prod. Rep. 16:267-281

Chisti, Y. 2007. Biodiesel from microalgae. Biotechnology Advances. 25: 294-306

Christakopoulos P, Macris B J, Kekos D. 1989. Direct fermentation of cellulose to ethanol by *Fusarium oxysporum*. Enzyme Microb Tech. 11:236-239.

Christakopoulos P., D. P. Koullas, D. Kekos, E. G. Koukios and B. J. Macris. 1991. Direct Ethanol Conversion of Pretreated Straw by *Fusarium oxysporum*. Bioresource Technology. 35: 297-300

Christakopoulos P., LIAN-WU L., KEKOS D., MACRIS B. J. 1993. Direct conversion of sorghum carbohydrates to ethanol by a mixed microbial culture. Bioresource Technology, 45: 89-92, Cooksey, K. E., J. B. Guckert, S. A. Williams, and P. R. Calli. 1987. Fluorometric determination of the neutral lipid content of microalgal cells using Nile Red". Journal of Microbiological Methods, 6: 333-345.

Daviere J. M., Langin T., and M. J. Daboussi. 2001. Potential role of transposable elements in the rapid reorganization of the *Fusarium oxysporum* genome. Fungal Genet Biol. 34:177-92.

Dey, P., Banerjee, J. & Maiti, M. K. Comparative lipid profiling of two endophytic fungal isolates—*Colletotrichum* sp. and *Alternaria* sp. having potential utilities as biodiesel feedstock. *Bioresource Technology* 102, 5815-5823 (2011).

Gong, Z. et al. Efficient conversion of biomass into lipids by using the simultaneous saccharification and enhanced lipid production process. *Biotechnology for Biofuels* 6, 36 (2013).

Gong, Z. et al. Lipid production from corn stover by the oleaginous yeast *Cryptococcus curvatus*. *Biotechnology for Biofuels* 7, 158 (2014).

Griffin, M. A., Spakowicz, D. J., Gianoulis, T. A., Strobel, S. A. 2010. Volatile organic compound production by organisms in the genus Ascocoryne and a re-evaluation of mycodiesel production by NRRL 50072. *Microbiology*, 156(Pt 12), 3814-29. 10.1099/mic.0.041327-0

Gross S., and E. I. Robbins. 2000, Chemistry and Ecology of Highly Acidic Environments. Acidophilic and acid-tolerant fungi and yeasts Hydrobiologia 433:91-109.

Hua-Van A., Daviere J. M., Kaper F., Langin T., and M. J. Daboussi. 2000. Genome organization in *Fusarium oxysporum*: clusters of class II transposons. Curr Genet. 37:339-47.

Hui, L. et al. Direct microbial conversion of wheat straw into lipid by a cellulolytic fungus of *Aspergillus oryzae* A-4 in solid-state fermentation. *Bioresource Technology* 101, 7556-7562 (2010).

Inskeep W. P., G. G. Ackerman, W. P. Taylor, M. Kozubal, S. Korf, and R. E. Macur. 2005. On the energetics of chemolithotrophy in nonequilibrium systems: case studies of geothermal springs in Yellowstone National Park. Geobiology. 3: 297-320.

Kerstetter J. D. and J. K. Lyons. 2001. Wheat straw for ethanol production in Washington: a resource, technical and economic assessment, Washington State University, Cooperative Extension Energy Program.

Kozubal M., Macur R. E., Korf S., Taylor W. P., Ackerman G. G., Nagy A., and W. P. Inskeep. 2008.Isolation and Distribution of a Novel Iron-Oxidizing Crenarchaeon from Acidic Geothermal Springs in Yellowstone National Park. Appl. Environ. Microbiol. 74: 942-949.

Lezinou V., Christakopoulos P., Kekos D., Macris B. J. 1994. Simultaneous saccharification and fermentation of sweet sorghum carbohydrates to ethanol in a fed-batch process. Biotechnology Letters. 16:983-988.

Li Q., Du W, Liu D. 2008. Perspectives of microbial oils for biodiesel production. Appl Microbiol Biotechnol. 80:749-56.

Liang, Y., Perez, I., Goetzelmann, K. & Trupia, S. Microbial lipid production from pretreated and hydrolyzed corn fiber. *Biotechnol Progress* 30, 945-951 (2014).

Liu, C.-Z., Wang, F., Stiles, A. R. & Guo, C. Ionic liquids for biofuel production: Opportunities and challenges. *Applied Energy* 92, 406-414 (2012).

Kerem Z. and Y. Hadar. 1995. Effect of manganese on preferential degradation oflignin by *Pleurotus* ostreatus during solid-state fermentation. Appl Environ Microbiol. 61(8): 3057-3062.

Mallette, N. D., Knighton, W. B., Strobel, G. A., Carlson, R. P., Peyton, B. M. 2012. Resolution of volatile fuel compound profiles from Ascocoryne sarcoides: a comparison by proton transfer reaction-mass spectrometry and solid phase microextraction gas chromatography-mass spectrometry. *Applied Microbiology and Biotechnology Express*, 2(1), 23. 10.1186/2191-0855-2-23

Meng X., Yang J., Xu X., Zhang L., Nie Q., and M. Xian. 2009. Biodiesel production from oleaginous microorganisms. Renewable Energy. 34: 1-5.

Nairn N. Saad R. R., Nairn M., 1985, Production of lipids and sterols by *Fusarium oxysporum* (Schlecht). Utilization of some agro-industrial by-products as additives and basal medium, Agricultural Wastes 14(3):207-220

Naqvi B. S., Hashmi K., Farooq A. K., Dilnawaz S., and A. M. Zafar. 1997. Production of Lipids by fermentation Preliminary Report. Journal of Islamic Academy of Sciences. 10:13-18.

Palmqvist E., and Barbel Hahn-Hagerdal. 2000. Fermentation oflignocellulosic hydrolysates. II: inhibitors and mechanisms of inhibition. Bioresource Technology 74: 25-33

Panagiotoua G., P. Christakopoulosb, L. Olssona. 2005. Simultaneous saccharification and fermentation of cellulose by *Fusarium oxysporum* F3-growth characteristics and metaboliteprofiling. Enzyme and Microbial Technology 36: 693-699

Patrick, C., Hallenbeck and Dipankar Ghosh. 2009. Advances in fermentative biohydrogen production: the way forward? Trends in Biotechnology. In Press.

Pinzi S., I. L. Garcia, F. J. Lopez-Gimenez, M. D. Luque de Castro, G. Dorado and M. P. Dorado. 2009. The Ideal Vegetable il-based Biodiesel Composition: A Review of Social, Economical and Technical Implications. Energy Fuels Ruan, Z. et al. Co-hydrolysis of lignocellulosic biomass for microbial lipid accumulation. *Biotechnol. Bioeng.* 110, 1039-1049 (2013).

Ruiz E., I. Romero M. Moya S. Sanchez V. Bravo E. Castro. 2007. Sugar fermentation by *Fusarium oxysporum* to produce ethanol. World J Microbiol Biotechnol. 23:259-267

Seo H., Kim H., Lee O, Ha J., Lee H., and K. Jung. 2009. Measurement of ethanol concentration using solvent extraction and dichromate oxidation and its application to bioethanol production process. Journal of Industrial Microbiology and Biotechnology. 36: 285-292.

Seraphim P., Michael K., A. George. 2004. Single cell oil (SCO) production by *Mortierella* isabellina grown on high-sugar content media. Bioresour Technol. 95:287-91.

Smith S. N. 2007. An Overview of Ecological and Habitat Aspects in the Genus *Fusarium* with Special Emphasis on the Soil-Borne Pathogenic Forms Plant Pathology Bulletin. 16: 97-120, Starkey, R. L. 1973. Effect of pH on tocicity of copper to *Scytalidium* sp., a copper-tolerant fungus, and some other fungi. J. gen. Microbiol. 78: 217-225.

Sung, M., Seo, Y. H., Han, S. & Han, J.-I. Biodiesel production from yeast *Cryptococcus* sp. using Jerusalem artichoke. *Bioresource Technology* 155, 77-83 (2014).

Tebo, B. M., W. C. Ghiorse, L. G. van Waasbergen, P. L. Siering, and R. Caspi. 1997. Bacterially-mediated mineral formation: Insights into manganese(II) oxidation from molecular geneticandbiochemical studies. In: J. F. Banfield and K. H. Nealson (Eds.) Geomicrobiology: Interactions Between Microbes and Minerals. Reviews in Mineralogy. 35:225-266.

Tsakali E., Petrotos K., D'Alessandro A. G., Goulas P. 2010. A review on whey composition and the method used for its utilization for food and pharmaceutical products. Proc. 6th International Conference on Simulation and Modelling in the Food and Bio-Industry (FOODSIM'2010), Braganca, Portugal, June 24-26. V. Cadavez and D. Thiel eds, EUROSIS-ETI Publication, pp. 195-201.

White J. S., Yohannan B. K., Walker G. M. 2008. Bioconversion of brewer's spent grains to bioethanol. FEMS Yeast Res. 8(7):1175-84. Epub 2008 Jun. 10.

Xie, H. et al. Enzymatic hydrolysates of corn stover pretreated by a N-methylpyrrolidone-ionic liquid solution for microbial lipid production. *Green Chem.* 14, 1202-1210 (2012).

Xiros, C., and P. Christakopoulos. 2009. Enhanced ethanol production from brewer's spent grain by *Fusarium oxysporum* consolidated system. Biotechnol Biofuels. 10:4.

Xiros C., Topakas E, Katapodis P, Christakopoulos P. 2008. Evaluation of *Fusarium oxysporum* as an enzyme factory for the hydrolysis of brewer's spent grain with improved biodegradability for ethanol production. Ind Crops Prod. 28:213-224.

Ya. E. Sergeeva, L. A. Galanina, D. A. Andrianova, and E. P. Feofilova. 2008. Lipids of Filamentous Fungi as a Material for Producing Biodiesel Fuel. Applied Biochemistry and Microbiology. 44:523-527.

The invention claimed is:

1. A fungal mycelial biomass, comprising:
   aerial hyphae; and
   three layers;
   wherein:
   the fungal mycelial biomass is in the form of a mat, is an essentially pure fungal biomass of a single fungal strain or species, is suitable for use as a food product, and is not viable.

2. The fungal mycelial biomass of claim 1, wherein the fungal mycelial biomass has a tensile strength of at least 0.05 kg/cm of mat width.

3. The fungal mycelial biomass of claim 1, wherein the fungal mycelial biomass has a protein content of at least 40%.

4. The fungal mycelial biomass of claim 1, wherein the three layers comprise:
   a bottom layer;
   a transition zone layer; and
   an aerial hyphae layer; wherein:
   the bottom layer is more dense than the aerial hyphae layer, the bottom layer comprises filaments aligned in a first direction and the aerial hyphae are predominantly oriented perpendicular to the first direction.

5. The fungal mycelial biomass of claim 4, wherein the bottom layer comprises filaments which are predisposed to be aligned parallel to at least one interface selected from the group consisting of a mat/air interface and a mat/medium interface.

6. The fungal mycelial biomass of claim 5, wherein the aerial hyphae are predominantly oriented perpendicular to the at least one interface.

7. The fungal mycelial biomass of claim 1, wherein the fungal mycelial biomas has a cell density of at least 25 g dry weight/l media.

8. The fungal mycelial biomass of claim 1, wherein the mat is 1 mm to 30 mm thick.

9. The fungal mycelial biomass of claim 1, wherein the mat has a lipid content of at least 39%.

10. The fungal mycelial biomass of claim 1, wherein the tensile strength of the mat is at least 0.2 kg/cm of mat width.

11. The fungal mycelial biomass of claim 1, wherein the fungal mycelial biomass further comprises extracellular polysaccharides.

12. The fungal mycelial biomass of claim 1, wherein the fungal mycelial biomass contains no residual feedstock.

* * * * *